(12) United States Patent
Nagtegaal

(10) Patent No.: US 10,881,450 B2
(45) Date of Patent: Jan. 5, 2021

(54) ELECTROSURGICAL DEVICE

(71) Applicant: GYRUS MEDICAL LIMITED, Cardiff (GB)

(72) Inventor: Marno Nagtegaal, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 532 days.

(21) Appl. No.: 15/404,270

(22) Filed: Jan. 12, 2017

(65) Prior Publication Data

US 2017/0196622 A1    Jul. 13, 2017

(30) Foreign Application Priority Data

Jan. 12, 2016  (GB) .................................. 1600546.4
Jan. 12, 2016  (GB) .................................. 1600567.0

(51) Int. Cl.
*A61B 18/14*     (2006.01)
*A61B 17/29*     (2006.01)
(Continued)

(52) U.S. Cl.
CPC .......... *A61B 18/1445* (2013.01); *A61B 17/29* (2013.01); *A61B 17/2909* (2013.01);
(Continued)

(58) Field of Classification Search
CPC ............ A61B 18/1442; A61B 18/1445; A61B 18/1447; A61B 18/085; A61B 2018/1452;
(Continued)

(56) References Cited

U.S. PATENT DOCUMENTS

| 4,800,880 A | 1/1989 | Catalano |
| 5,104,397 A | 4/1992 | Vasconcelos et al. |

(Continued)

FOREIGN PATENT DOCUMENTS

| CN | 103381106 A | 11/2013 |
| DE | 202010005263 U1 | 6/2010 |

(Continued)

OTHER PUBLICATIONS

Jul. 5, 2016 Search Report issued in Britrish Patent Application No. GB1600546.4.

(Continued)

*Primary Examiner* — Thomas A Giuliani
(74) *Attorney, Agent, or Firm* — Oliff PLC

(57) ABSTRACT

A surgical instrument having a handle, elongate shaft protruding from handle and end-effector located at end of shaft is described. To allow for rotation of the end-effector the shaft is connected to a rotation wheel mounted on handle, towards rearward end of handle proximal to the user. The rotation wheel is in the form of a thumbwheel, having an ergonomically designed shape that tapers from distal direction to proximal direction, with angle of the taper matching angle of the outer surface of the handle. The outer tapered surface of the thumbwheel has a number of shaped cut-out or scalloped portions arranged around the outer circumference of the wheel, and arranged in use to receive the tip of a user's thumb to allow the user to rotate the wheel in order to set the rotational orientation of the end-effector. Such an arrangement provides a comfortable and easy to use instrument.

19 Claims, 40 Drawing Sheets

(51) Int. Cl.
  *A61B 18/00* (2006.01)
  *A61B 17/00* (2006.01)
  *A61B 90/00* (2016.01)

(52) U.S. Cl.
  CPC .......... *A61B 2017/00367* (2013.01); *A61B 2017/00371* (2013.01); *A61B 2017/292* (2013.01); *A61B 2017/293* (2013.01); *A61B 2017/2913* (2013.01); *A61B 2017/2929* (2013.01); *A61B 2017/2945* (2013.01); *A61B 2017/2946* (2013.01); *A61B 2018/0063* (2013.01); *A61B 2018/00083* (2013.01); *A61B 2018/0091* (2013.01); *A61B 2018/0094* (2013.01); *A61B 2018/00142* (2013.01); *A61B 2018/00178* (2013.01); *A61B 2018/00184* (2013.01); *A61B 2018/00202* (2013.01); *A61B 2018/00589* (2013.01); *A61B 2018/00601* (2013.01); *A61B 2018/00607* (2013.01); *A61B 2018/00952* (2013.01); *A61B 2018/1455* (2013.01); *A61B 2090/032* (2016.02); *A61B 2090/035* (2016.02)

(58) Field of Classification Search
  CPC .... A61B 2018/1455; A61B 2018/0091; A61B 2018/00607; A61B 2018/00601; A61B 2018/00952; A61B 2018/0063; A61B 2018/00589; A61B 2018/00202; A61B 2018/00595; A61B 17/29; A61B 2017/2913; A61B 2017/2946; A61B 2017/2916; A61B 2017/2903; A61B 2017/2929; A61B 2017/00371; A61B 2017/00389
  USPC .............. 606/41, 48–52, 203, 205, 208, 171
  See application file for complete search history.

(56) References Cited

U.S. PATENT DOCUMENTS

| | | | |
|---|---|---|---|
| 5,352,235 A | 10/1994 | Koros et al. | |
| 5,730,740 A | 3/1998 | Wales et al. | |
| 5,776,130 A | 7/1998 | Buysse et al. | |
| 5,797,938 A | 8/1998 | Paraschac et al. | |
| 6,039,733 A | 3/2000 | Buysse et al. | |
| 6,179,834 B1 | 1/2001 | Buysse et al. | |
| 7,083,618 B2 | 8/2006 | Couture et al. | |
| 7,101,373 B2 | 9/2006 | Dycus et al. | |
| 7,131,971 B2 | 11/2006 | Dycus et al. | |
| 7,766,910 B2 | 8/2010 | Hixson et al. | |
| 7,846,161 B2 | 12/2010 | Dumbauld et al. | |
| 8,197,479 B2 * | 6/2012 | Olson ................ | A61B 18/1445 606/50 |
| 2002/0188294 A1 | 12/2002 | Couture et al. | |
| 2009/0171147 A1 | 7/2009 | Lee et al. | |
| 2009/0248020 A1 | 10/2009 | Falkenstein et al. | |
| 2010/0152757 A1 | 6/2010 | Slater | |
| 2011/0155784 A1 | 6/2011 | Shelton, IV et al. | |
| 2012/0109186 A1 | 5/2012 | Parrott et al. | |
| 2013/0296922 A1 * | 11/2013 | Allen, IV ........... | A61B 18/1445 606/205 |
| 2014/0135805 A1 | 5/2014 | Windgassen et al. | |
| 2014/0221999 A1 | 8/2014 | Cunningham et al. | |
| 2014/0277046 A1 | 9/2014 | Mark et al. | |
| 2015/0209103 A1 | 7/2015 | Artale et al. | |
| 2015/0223870 A1 | 8/2015 | Olson et al. | |

FOREIGN PATENT DOCUMENTS

| | | |
|---|---|---|
| EP | 1870043 A2 | 12/2007 |
| EP | 2532315 A1 | 12/2012 |
| EP | 2628459 A2 | 8/2013 |
| EP | 2853220 A1 | 4/2015 |
| EP | 2853221 A1 | 4/2015 |
| WO | 98/14124 A1 | 4/1998 |
| WO | 2008008178 A2 | 1/2008 |
| WO | 2008/024911 A2 | 2/2008 |
| WO | 2008020964 A2 | 2/2008 |
| WO | 2014/074807 A1 | 5/2014 |
| WO | 2015175298 A2 | 11/2015 |

OTHER PUBLICATIONS

Jul. 5, 2016 Search Report issued in Britrish Patent Application No. GB1600550.6.
Nov. 16, 2016 Search Report issued in Britrish Patent Application No. GB1600550.6.
Jul. 12, 2016 Search and Examination Report issued in British Patent Application No. 1600567.0.
May 17, 2017 Search and Examination Report issued in British Patent Application No. 1700328.6.
Jun. 2, 2020 Office Action issued in Chinese Patent Application No. 201710020802.2.

* cited by examiner

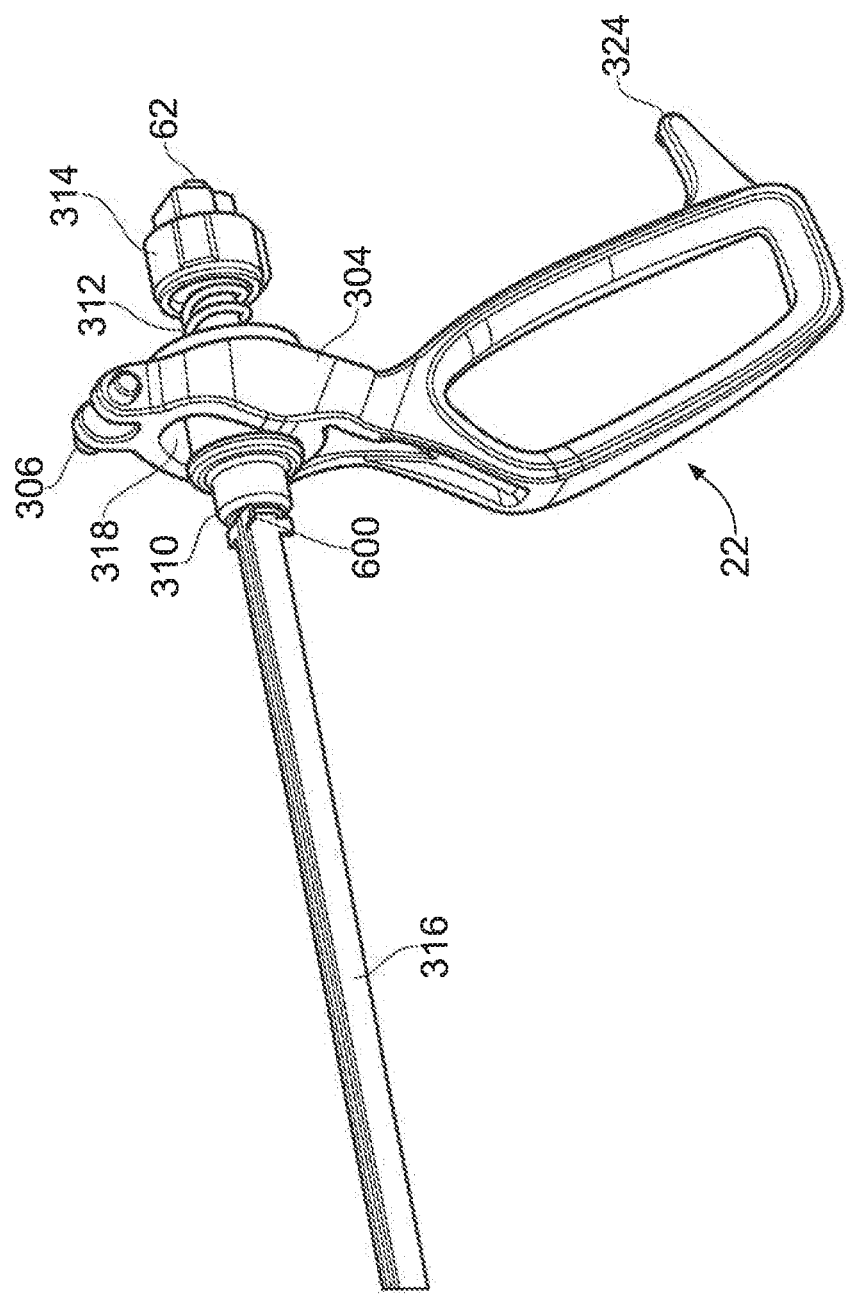

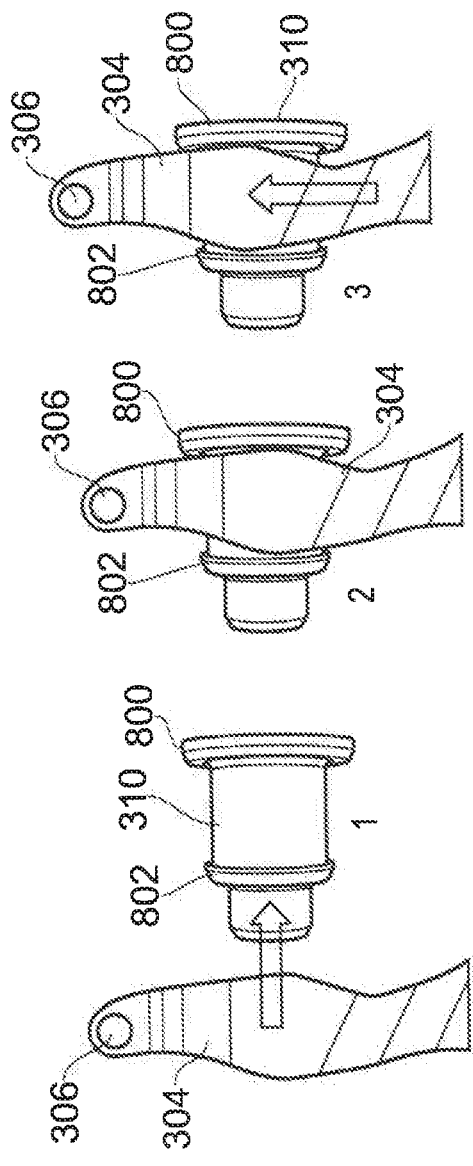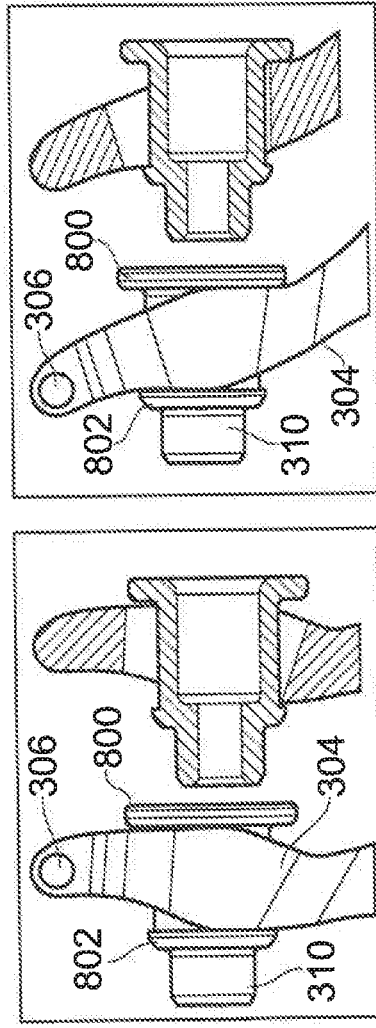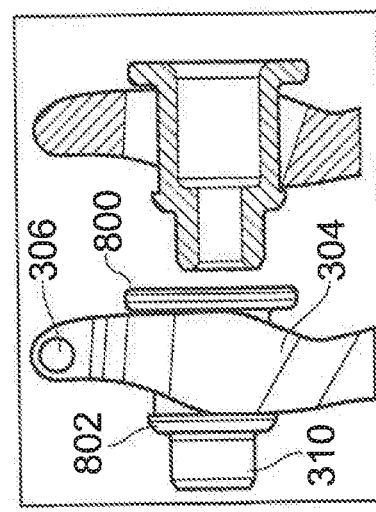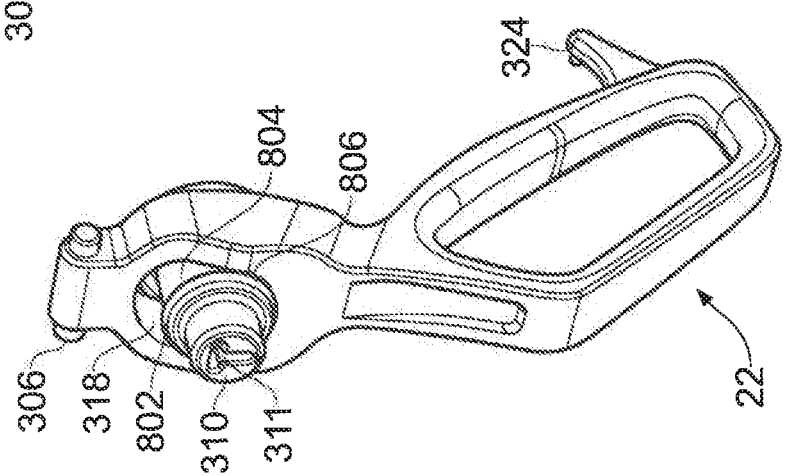

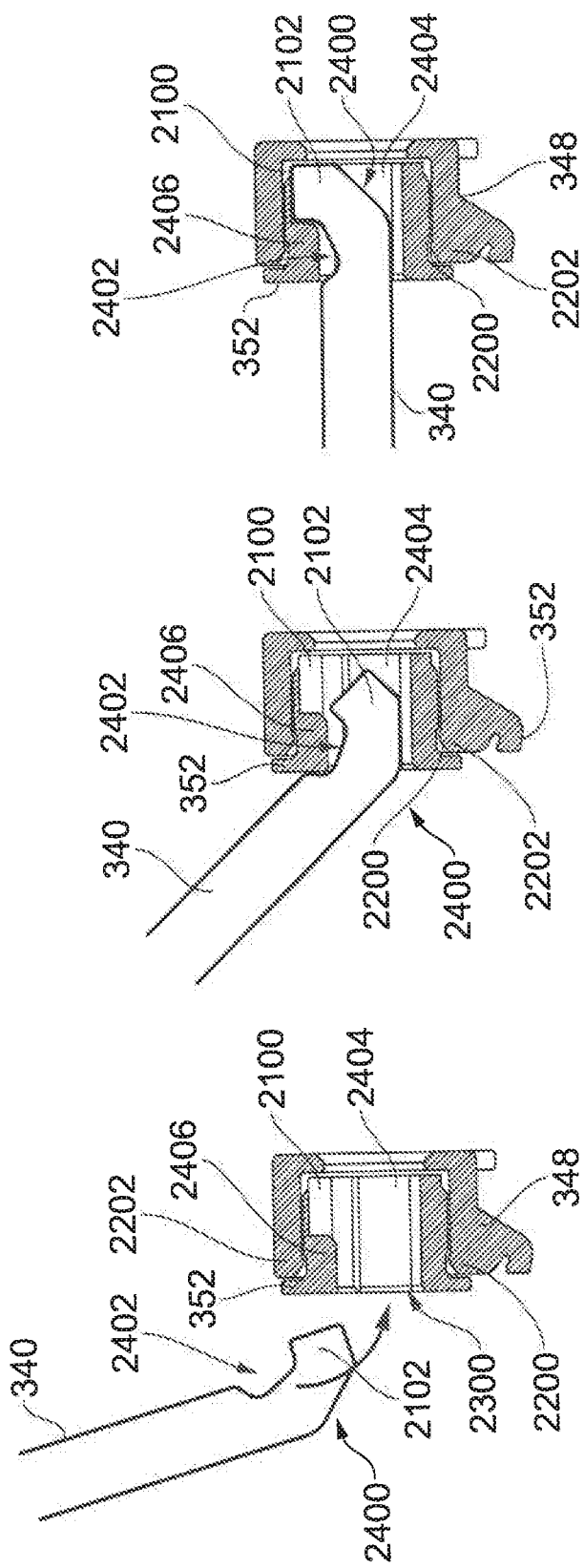

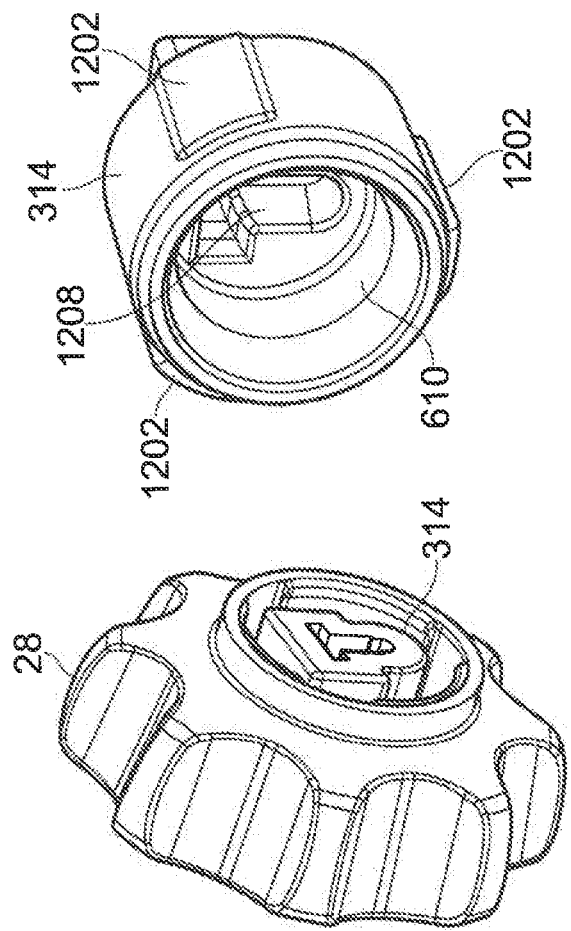
FIG. 30
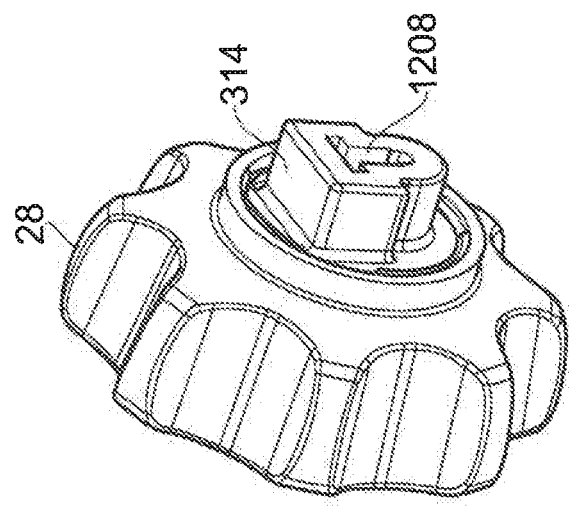
FIG. 29b
FIG. 29a

ELECTROSURGICAL DEVICE

This application claims priority to GB 1600546.4 filed Jan. 12, 2016, and GB 1600567.0 filed Jan. 12, 2016. The disclosure of the prior applications is hereby incorporated by reference herein in its entirety.

TECHNICAL FIELD

Embodiments of the present invention described herein relate to an electrosurgical device, and in particular an electrosurgical forceps device wherein a mechanical blade provides a tissue cutting action in combination with electrosurgical electrodes providing a tissue coagulation or sealing effect.

BACKGROUND TO THE INVENTION AND PRIOR ART

Electrosurgical instruments provide advantages over traditional surgical instruments in that they can be used for coagulation and tissue sealing purposes. One such prior art arrangement is known from US2015/223870A1, which describes an endoscopic bipolar forceps including a housing and a shaft, the shaft having an electrosurgical end effector assembly at a distal end thereof, which includes two jaw members for grasping tissue therebetween. Each jaw member is adapted to connect to an electrosurgical energy source, enabling them to affect a tissue seal to tissue held therebetween. A drive assembly is included within the housing for moving the jaw members. A movable handle is also included, such that movement of the handle actuates the drive assembly to move the jaw members relative to each other. A knife channel is included within the end effector configured to allow reciprocation of a knife blade within the knife channel, to allow cutting of tissue.

Other prior art arrangements include U.S. Pat. Nos. 5,730,740, 5,104,397, 4,800,880, WO98/14124, US2012/0109186, U.S. Pat. No. 5,352,235, WO2014/074807, U.S. Pat. No. 7,846,161, WO2008/024911, U.S. Pat. Nos. 5,776,130, 6,039,733, 6,179,834, 7,131,971, 7,766,910, EP2628459, US2014/0221999, U.S. Pat. No. 7,083,618, US2009/0248020, US2015/0209103, U.S. Pat. Nos. 5,797,938 and 7,101,373.

SUMMARY OF THE INVENTION

Embodiments of the invention provide a surgical instrument having a handle, an elongate shaft protruding from the handle and an end-effector located at the end of the shaft. In order to allow for rotation of the end-effector the shaft is connected to a rotation wheel mounted on the handle, towards the rearward end of the handle proximal to the user. The rotation wheel is in the form of a thumbwheel, having an ergonomically designed shape that tapers from the distal direction to the proximal direction, with the angle of the taper matching the angle of the outer surface of the handle. The outer tapered surface of the thumbwheel has a number of shaped cut-out or scalloped portions arranged around the outer circumference of the wheel, and arranged in use to receive the tip of a user's thumb to allow the user to rotate the wheel in order to set the rotational orientation of the end-effector. Such an arrangement provides a comfortable and easy to use instrument.

In view of the above, from one aspect there is provided a surgical instrument including a handle, having a longitudinal axis defining a generally forward and a rearward direction, the handle having an external casing, an elongate shaft extending from the forward end of the handle, an end effector positioned at the distal end of the elongate shaft, a rotatable thumb-wheel located on the handle, rotation of the thumb-wheel causing a corresponding rotation of the elongate shaft, characterised in that the thumb-wheel is located towards the rearward end of the handle, and that the thumb-wheel has a generally tapered external shape such that at least part of the external surface of the thumb-Wheel slopes from a relatively narrow diameter at the rearward end of the thumb-wheel, to a relatively broader diameter towards the forward end of the thumb-wheel, the angle of the sloping part of the external surface of the thumbwheel being substantially equal to the angle of the external casing in the region of the thumbwheel. With such an arrangement a comfortable and easy to use arrangement of thumbwheel to provide for rotation of the end-effector is obtained.

In one embodiment the external surface of the thumb-wheel is provided with a scalloped surface including a plurality of indents adapted to receive the fingers and thumb of a user operating the thumb-wheel. The plurality of indents may be tapered such that they form a relatively narrow diameter at the rearward end of the thumb-wheel, and a relatively broader diameter towards the forward end of the thumb-wheel.

With respect to the precise shape of the indents, the plurality of indents may taper at an angle of between 5 and 35 degrees, or alternatively at an angle of between 10 and 25 degrees. Such a taper angle provides a comfortable and ergonomic design.

Regarding the number of indents, the thumb-wheel may include between 6 and 10 indents, but in one embodiment the thumb-wheel includes 8 indents. The number of indents may be selected depending on the size of the thumbwheel, with the size of the indents being selected to allow different user thumb sizes to be accommodated.

In some embodiments the external surface of the handle is tapered in the region of the thumb-Wheel at an angle similar to that of the external surface of the thumb-wheel. This also provides a comfortable and ergonomic arrangement for the user.

In some embodiments the thumbwheel protrudes through one or more apertures in the external casing of the handle. For example, in one example the external casing includes two apertures, opposite one another on each side of the handle, and in a further example the one or more apertures may be trapezoidal in shape, for example having parallel sides orthogonal to the longitudinal axis of the handle. In particular, in a particular example, one of the parallel sides is longer than the other, the longer side being at the forward end of the aperture and the shorter side being at the rearward end of the aperture. Such arrangements provide for ergonomic design of the thumbwheel to allow for ease of use.

The surgical instrument may include an actuating mechanism movable between a first position and a second position, movement of the actuating mechanism from its first position to its second position causing the end effector to move from a first condition to a second condition. In this respect, in some embodiments the end effector comprises a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween.

The surgical instrument may be an electrosurgical instrument. In such a case the end effector includes one or more electrodes, and the instrument includes electrical connections capable of connecting the instrument to an electrosurgical generator.

BRIEF DESCRIPTION OF THE DRAWINGS

Embodiments of the invention will now be further described by way of example only and with reference to the accompanying drawings, wherein like reference numerals refer to like parts, and wherein:

FIG. 7 is a perspective view of the clamping mechanism of the electrosurgical instrument of FIG. 3;

FIGS. 8a-8f illustrate the assembly of a part of the electrosurgical instrument of FIG. 3;

FIGS. 24a-24e illustrate the assembly of one part of the cutting mechanism of the electrosurgical instrument of FIG. 3;

FIGS. 29a-b show a blade angle adjustment part of the electrosurgical instrument of FIG. 3;

FIG. 30 is a perspective view of part of the clamping mechanism of the electrosurgical instrument of FIG. 3

DESCRIPTION OF THE EMBODIMENTS

An embodiment of the invention will now be described. A brief overview of the whole embodiment will first be given, followed by detailed descriptions of particular aspects thereof.

1. OVERVIEW OF THE CONFIGURATION OF THE INSTRUMENT

Figure 1:
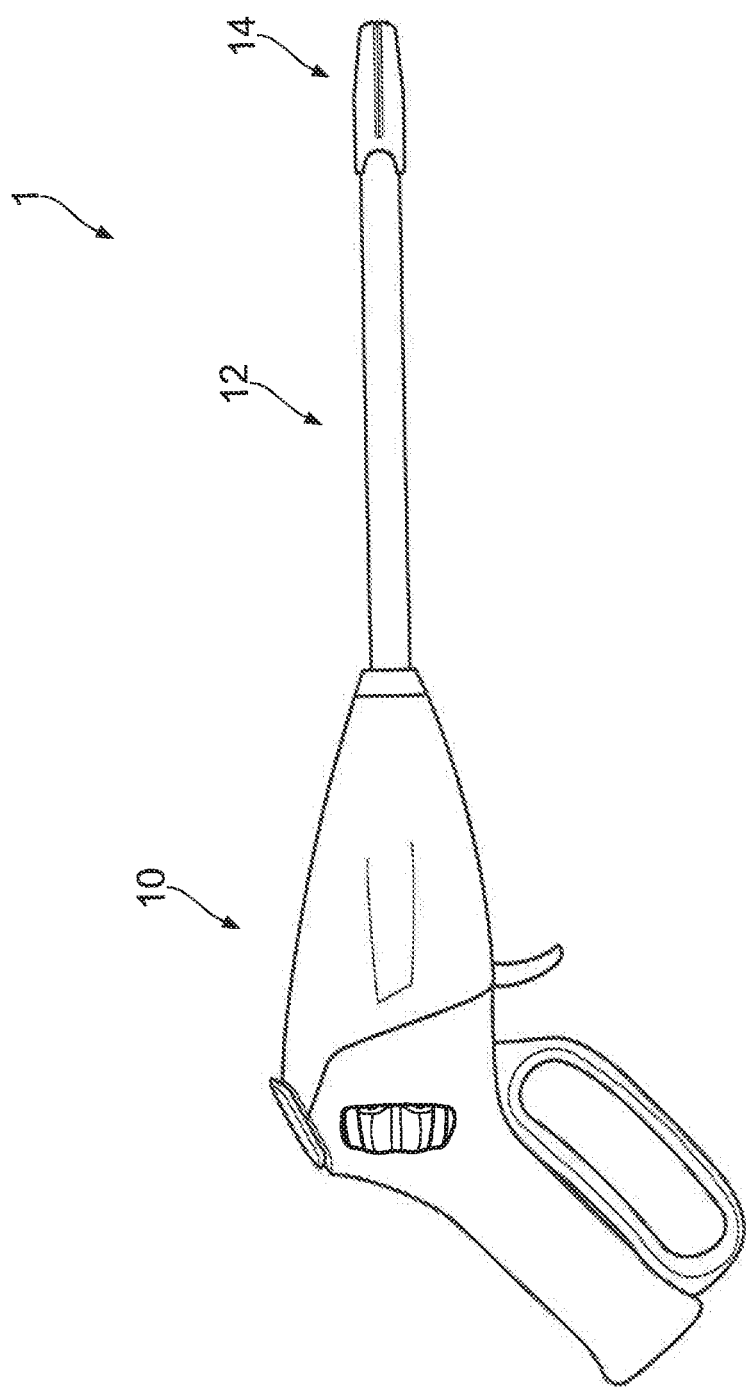
FIG. 1 is a side view of an electrosurgical instrument according to an embodiment of the present invention.

FIG. 1 illustrates an electrosurgical instrument 1 according to an example of the present invention. The instrument 1 includes a proximal handle portion 10, an outer shaft 12 extending in a distal direction away from the proximal handle portion, and a distal end effector assembly 14 mounted on a distal end of the outer shaft. The end effector assembly 14 may by way of example be a set of opposed jaws arranged to open and close, and comprising one or more electrodes arranged on or as the inner opposed surfaces of the jaws and which in use have connections to receive an electrosurgical radio frequency (RF) signal for the sealing or coagulation of tissue. The jaws are further provided with a slot or other opening within the inner opposed surfaces through which a mechanical cutting blade or the like may protrude, when activated by the user. In use, the handle 10 is activated by the user in a first manner to clamp tissue between the jaws 14, and in a second manner to supply the RF current to the electrodes in order to coagulate the tissue. The jaws 14 may be curved so that the active elements of the instrument 1 are always in view. This is important in vessel sealing devices that are used to operate on regions of the body that obscure the user's vision of the device during use. The handle 10 may be activated by the user in a third manner to cause the blade to protrude between the jaws 14, thereby cutting the tissue clamped between. Once the required cutting and sealing has been completed, the user can release the tissue from the jaws 14.

Figure 2:
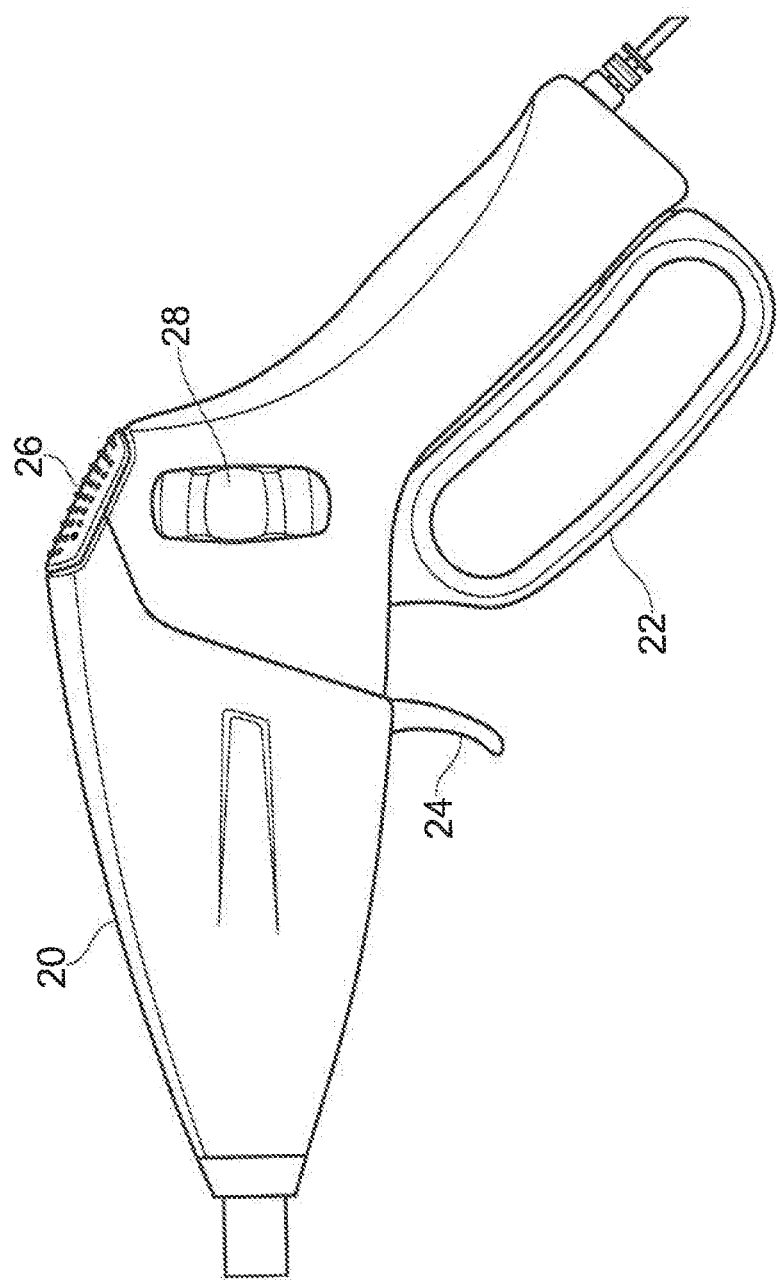
FIG. 2 is a side view of the handle of the electrosurgical instrument according to the embodiment of the present invention.

The handle 10, as shown by FIG. 2, comprises a easing 20 formed of two clamshell mouldings 300, 302 which houses all of the components required to operate and rotate the jaws 14, coagulate and cut tissue. The clamshell mouldings in the assembled device are ultrasonically welded together, once the internal components have been assembled inside. The handle 10 includes a clamping handle 22 for clamping tissue between the jaws 14, a trigger 24 for cutting the tissue, switch 26 for activating and deactivating the RF supply to the electrodes in the jaws 14 in order to coagulate tissue, and a rotation wheel 28 for rotating the jaws 14 in order to reach tissue from different angles. As such, the configuration of handle 10 is such that the instrument 1 and all its functions can be operated using a single hand, with all of the operational mechanisms being easily accessible.

Figure 3:
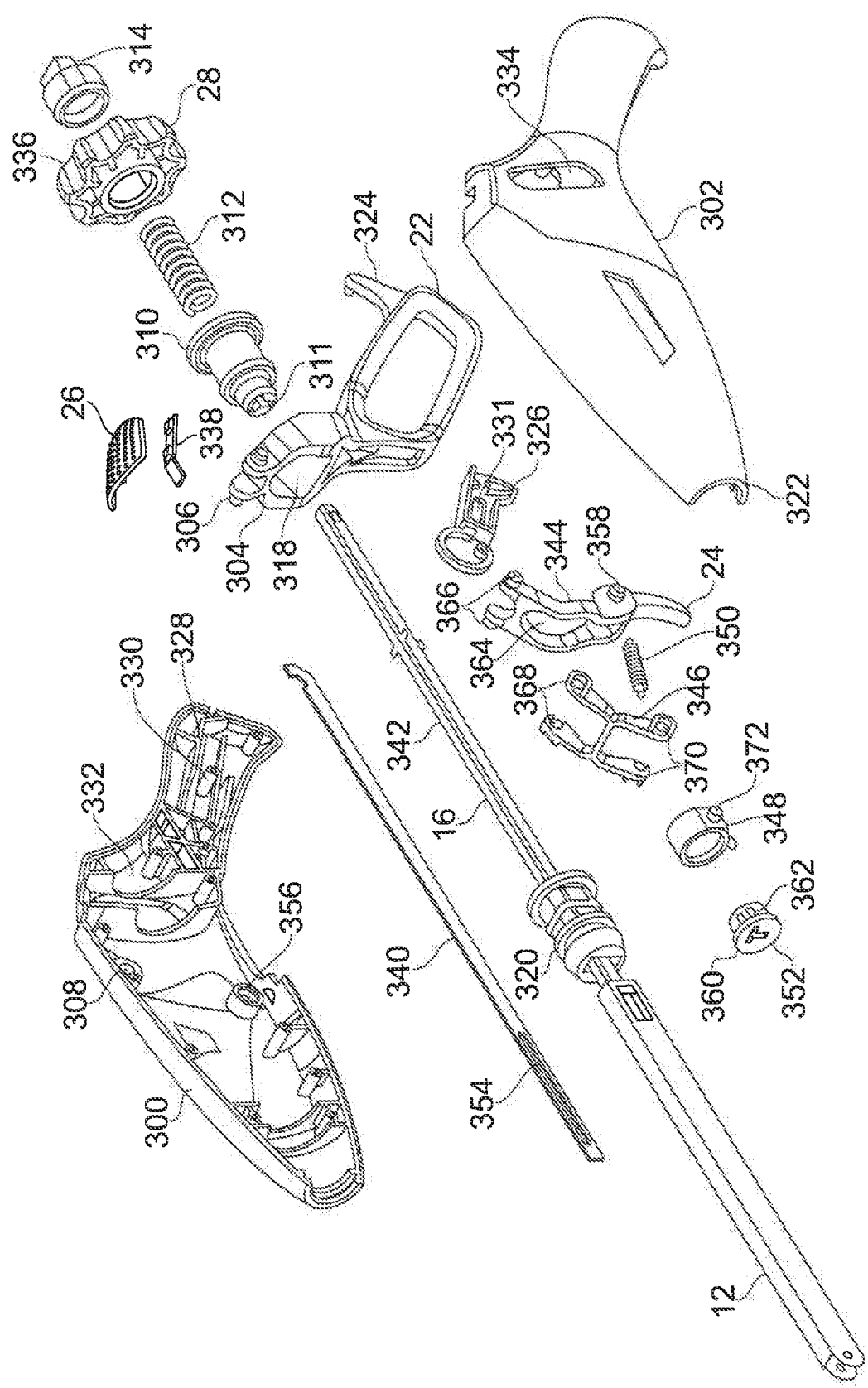
FIG. 3 is an exploded view of an electrosurgical instrument according to the embodiment the present invention.

FIG. 3 shows all of the features of instrument 1 required to perform its functions, including those housed within the two clamshell mouldings 300, 302 of the casing 20. To clamp tissue between the jaws 14, a clamping mechanism is actuated using the clamping handle 22. The clamp handle 22 further comprises a collar 304, the collar 304 comprising a hinge 306 that functions as a fulcrum around which the clamping handle 22 rotates. For example, the hinge 306 may be two outward facing pins that click in to corresponding mouldings 308 integral to the clamshell mouldings 300, 302 to thereby provide an anchor point around which the clamping handle 22 rotates. The clamping mechanism further comprises a collar moulding 310, a spring 312, and an inner moulding 314, as further illustrated by FIGS. 4 to 7, all of which are threaded along a drive shaft 316.

The collar 304 comprises a keyhole aperture 318 in which the collar moulding 310 sits. The aperture 318 has a larger diameter at the top than that at the bottom, wherein the collar moulding 310 is arranged to sit within the lower part of the aperture 318, as illustrated by FIG. 8a. In assembly, the collar moulding 310 easily fits through the larger part of the aperture 318 such that the collar 304 sits between two flanges 800, 802, as shown by FIGS. 8b-8c. As shown by FIG. 8d, the collar 304 is then pushed upwards to engage the smaller part of the keyhole aperture 318 with the collar moulding 310. Once, the hinge 306 is connected to the hinge mouldings 308 within the casing 20, the collar moulding 310 is retained within the lower part of the aperture 318 where it is free to move rotationally within the aperture 318.

Figure 6:
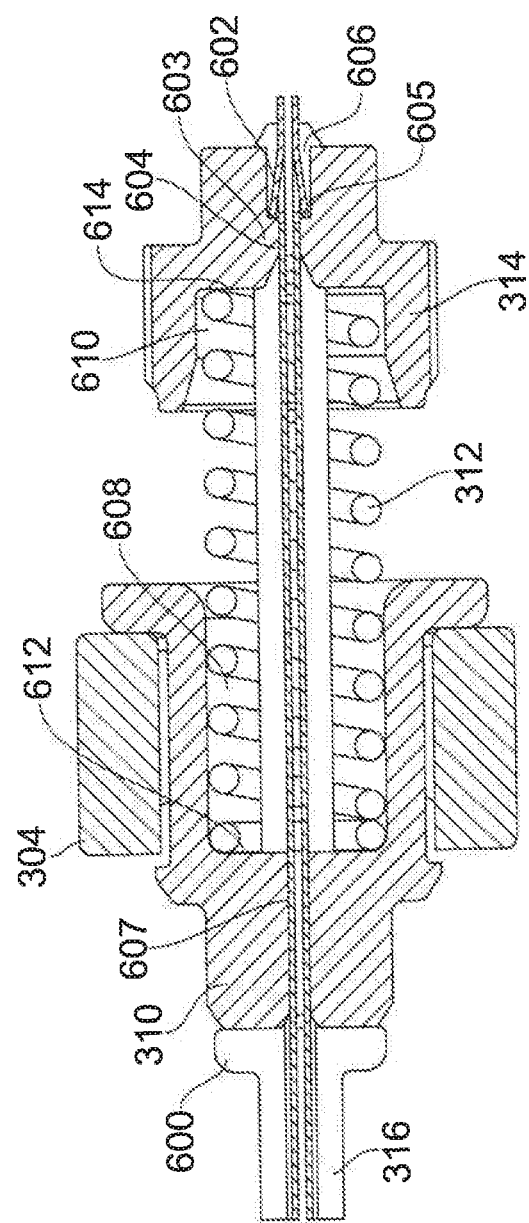
FIG. 6 is a sectional view of part of the clamping mechanism of the electrosurgical instrument of FIG. 3.

As shown in FIG. 6, the collar moulding 310, spring 312 and inner moulding 314 are retained between protruding members 600, 602 such that they cannot travel axially beyond these protruding members 600, 602. In this respect, the protruding members 602 at the proximal end of the drive shaft 316 are compressible so as to allow the drive shaft 316 to be passed through a channel 604 in the proximal end of the inner moulding 314. The drive shaft 316 is pushed through the channel 604 until it reaches an opening 606, wherein the protruding members 602 are no longer compressed such that they lie flush against the walls of the drive shaft 316. Instead, the protruding members 602 fan out and push against the walls of the opening 606 such that the span of the protruding members 602 extends beyond the diameter of the channel 604. Consequently, the drive shaft 316 cannot be pulled back through the channel 604 and is thus locked in place.

The distance between the protruding members 600, 602 is such that the spring 312 is at least partially compressed between the collar moulding 310 and the inner moulding 314. This pre-compression is important for ensuring that the correct clamping load is applied when the clamping mechanism is activated, as will be described in more detail below. Both the collar moulding 310 and the inner moulding 314 comprise cavities 608, 610 into which the spring 312 extends. In particular, a substantial proportion of the length of the collar moulding 310 houses the spring 312. This arrangement allows for a longer spring 312 which is important for ensuring that the spring 312 does not ever reach its solid length during use.

The main body of the drive shaft 316 lies within the outer shaft 12, the distal end of the drive shaft 316 being coupled to both the distal end of the outer shaft 12 and the jaws 14. The drive shaft 316 moves axially within the outer shaft 12 and it is this axial movement that moves the jaws 14 from an open to a closed position, as can be seen from FIGS. 4 and 5a. For example, the drive shaft 316 is coupled to the jaws 14 by means of a drive pin 400 in a cam slot 402, whereby movement of the drive pin 400 within the cam slot 402 moves the jaws 14 between the open and closed position. The coupling between the drive shaft 316, the outer shaft 12 and the jaws 14 is such that rotational movement of the drive shaft 316 is transferred to the outer shaft 12 and jaws 14.

Figure 9A:
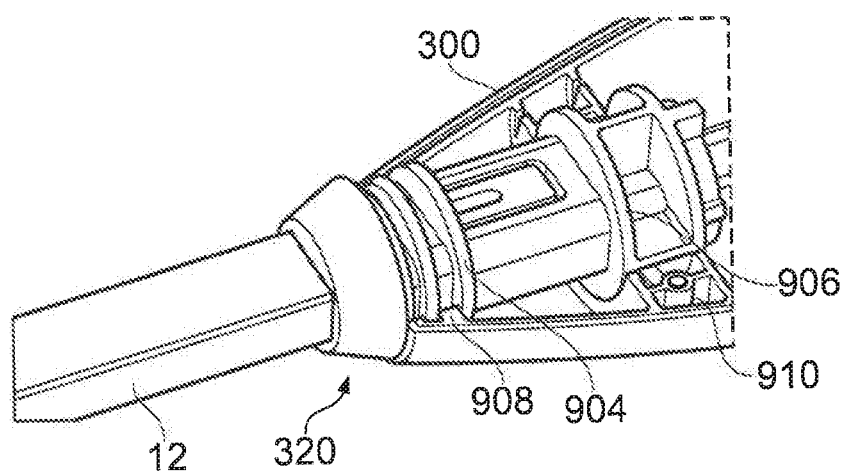
FIGS. 9a-9b are sectional views of a part of the electrosurgical instrument of FIG. 3.
Figure 9B:
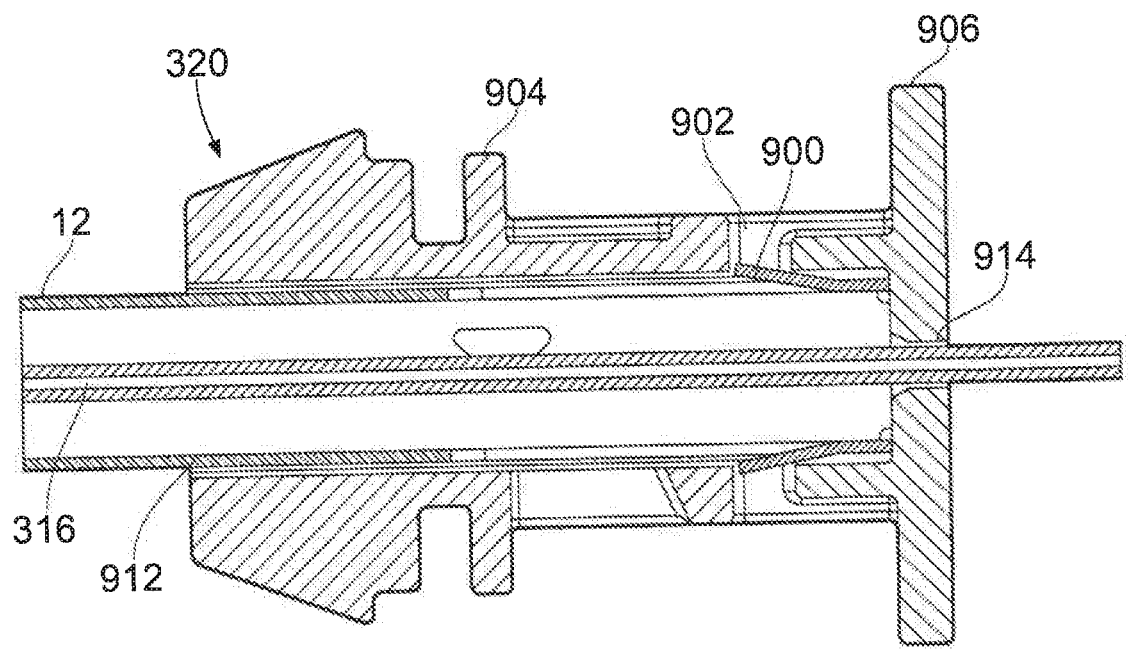
Figure 10A:
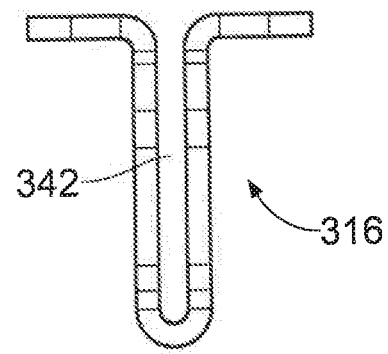
FIGS. 10a-10c show a blade guide part of the electrosurgical instrument of FIG. 3.

The outer shaft 12 and drive shaft 316 are coupled at a further point by means of a shaft moulding 320. The shaft moulding 320 sits within a socket 322 of the casing 20, and thus couples the outer shaft 12 to the casing 20. The outer shaft 12 is attached to the shaft moulding 320 by any suitable means, for example, snap-fit tabs 900 that cooperate with corresponding notches 902 within the shaft moulding 320, as shown in FIG. 9b. The drive shaft 316 is threaded through the body of the shaft moulding 320 via an aperture (not shown) that matches the cross-sectional "T" shape of the drive shaft 316, as illustrated by FIG. 10*a*. The shaft moulding 320 is arranged such that it is free to rotate within the socket 322. For example, the shaft moulding 320 may comprise cylindrical flange features 904, 906 that rotate within concentric mating faces 908, 910 provided within the clamshell mouldings 300, 302. Therefore, the shaft moulding 320 rotates with the drive shaft 316, which in turn translates this rotational movement to the outer shaft 12 and the jaws 4. The shaft moulding 320 thus acts as a rotational and axial guide for the drive shaft 316.

Figure 11:
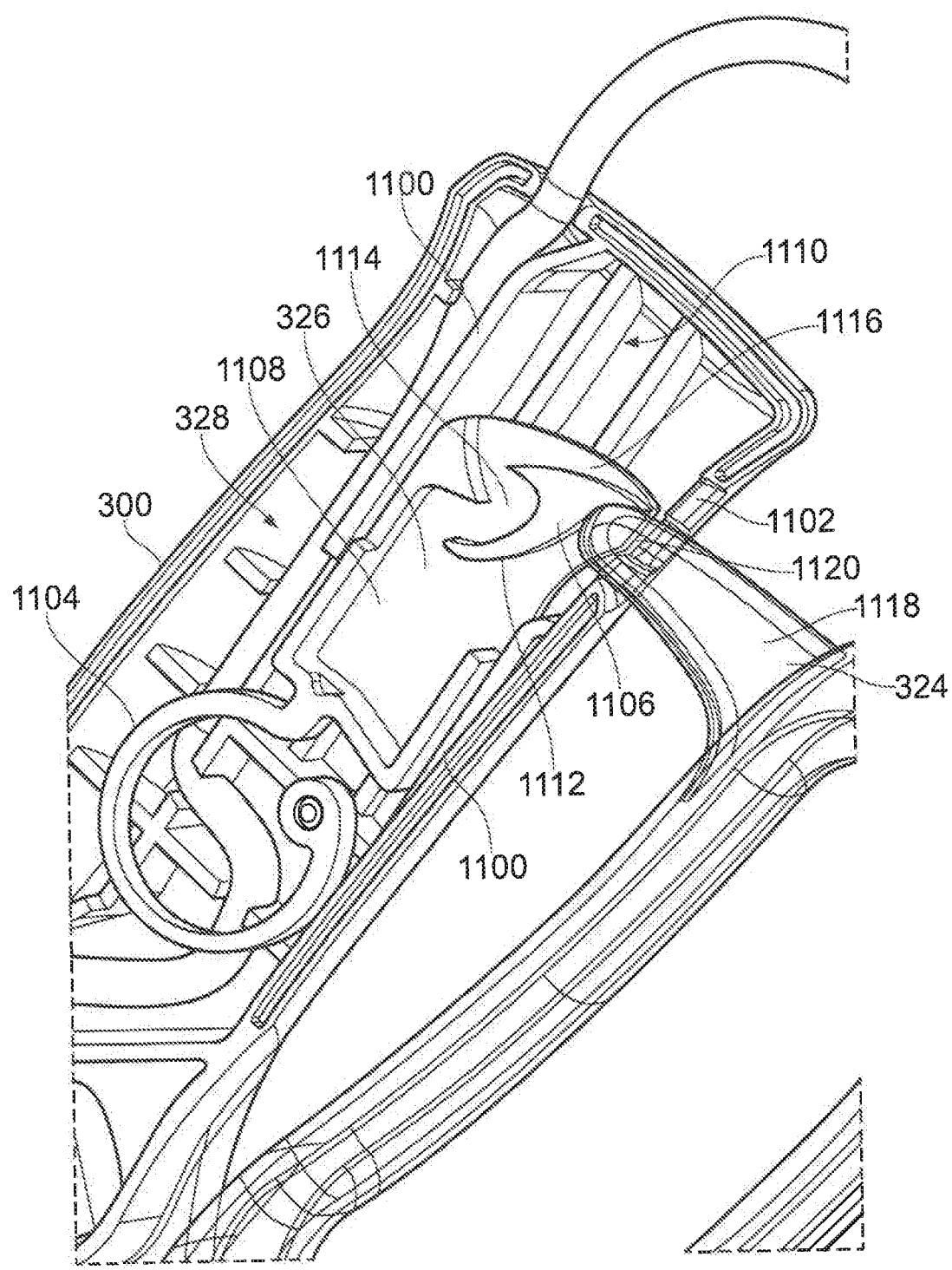
FIG. 11 shows a latch part of the electrosurgical instrument of FIG. 3.
Figure 46:
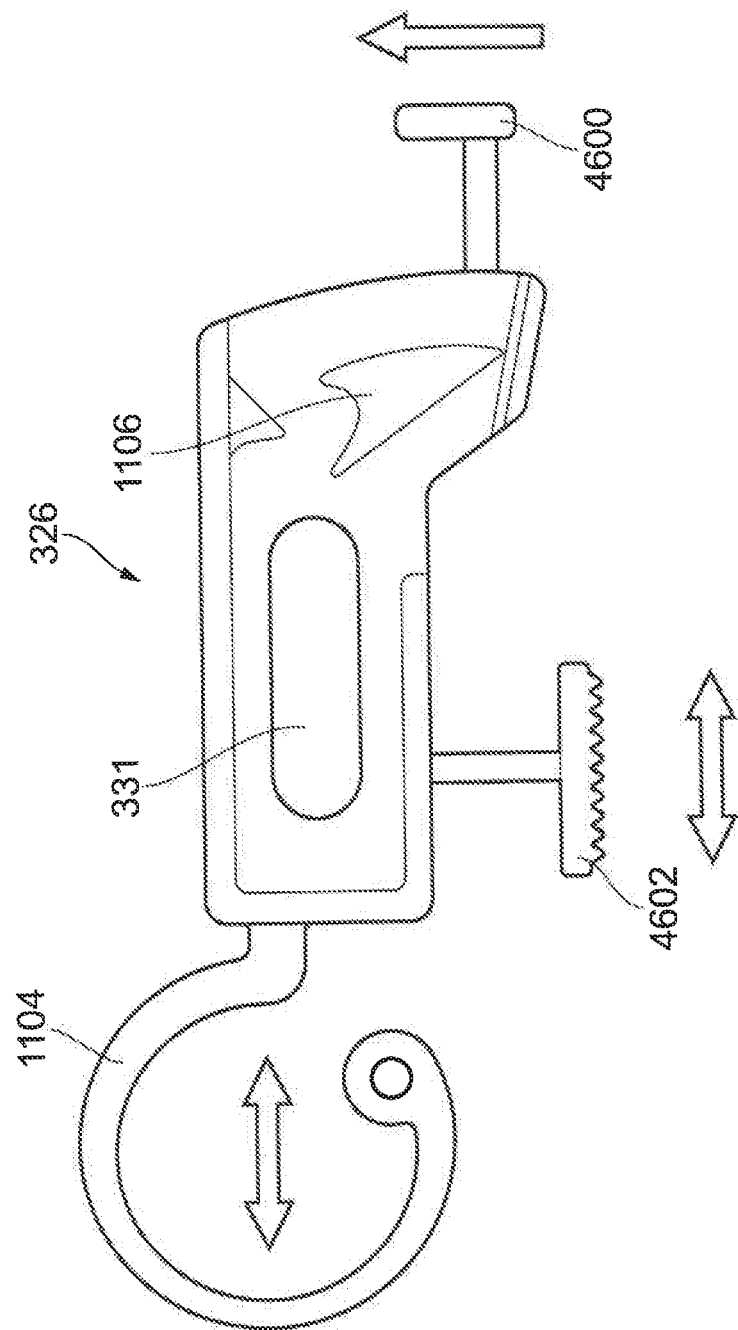
FIG. 46 further illustrates a latch part of the electrosurgical instrument of FIG. 3.

The clamping handle 22 comprises a latch 324 arranged to cooperate with a latch moulding 326 which sits within the proximal end 328 of the casing 20. The latch moulding 326 may be held in place by any suitable means, for example, by means of a moulded pin 330 integral to one of the clamshell mouldings 300, 302, as shown by FIG. 3, or by simply by the moulded walls 1100 integral to the clamshell moulding 300, as shown by FIG. 11. When the clamping handle 22 is driven towards the casing 20 so as to close the jaws 14, the latch 324 enters the casing 20 via an opening 1102 and engages with the latch moulding 326 so as to retain the clamping handle 22 in this position. As is shown in FIGS. 26*a* to 26*f*, the latch moulding 326 comprises a two way spring 1104 and a cam path 1106 along which the latch 324 traverses. As shown in FIG. 46, the latch mechanism may also include an override component 4600 to allow the user to manually release the latch 324 if it gets stuck, and a lock-out component 4602 to disable the latch mechanism altogether. The override component 4600 and lock-out component 4602 may be provided on the latch moulding 326 or may be integral to the inside of the casing 20.

Figure 12:
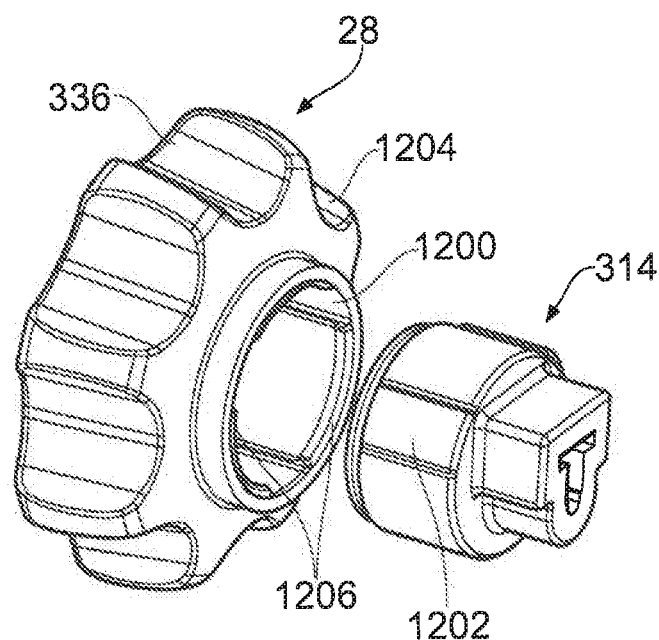
FIG. 12 shows a blade angle adjustment part of the electrosurgical instrument of FIG. 3.

As described above, the handle 10 further comprises a rotation wheel 28, wherein the rotation wheel 28 is arranged to encase the inner moulding 314, in this respect, the rotation wheel 28 and inner moulding 314 have interlocking members 1200, 1202, as shown by FIG. 12. These interlocking members 1200, 1202 couple together such that the rotation Wheel 28 and inner moulding 314 rotate together, whilst still allowing axial movement of the inner moulding 314 within the rotation wheel 28, as can be seen from FIGS. 13*a*-13*b*. Therefore, rotation of the rotation wheel 28 causes rotation of the inner moulding 314, which subsequently rotates the drive shaft 316 and the collar moulding 310. For stability, the rotation wheel 28 comprises cylindrical faces 1204 that rotationally slide on internal mating faces (not shown) integral to the clamshell mouldings 300, 302.

Figure 14A:
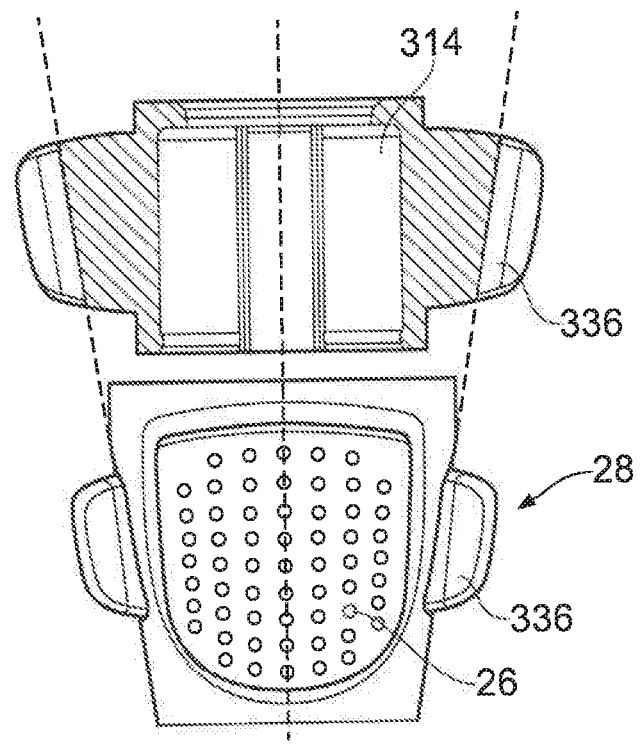
FIGS. 14a-14b show a blade angle control wheel part of the electrosurgical instrument of FIG. 3.
Figure 14B:
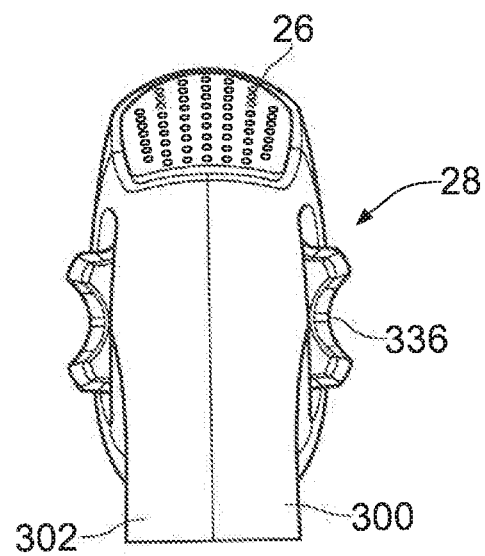

To enable the user to rotate the jaws 14, the casing 20 has two openings 332, 334 through which scalloped portions 336 of the rotation wheel 28 protrude. The two openings 332, 334 are opposite one another on each side of the handle, and are trapezoidal in shape. In particular, the trapezoidal apertures have parallel sides orthogonal to the longitudinal axis of the handle, and one of the parallel sides may be longer than the other, the longer side being at the forward end of the aperture, and the shorter side being at the rearward end. The scalloped portions 336 are conveniently sloped so as to comfortably fit the thumb or fingers of the user. In this respect, the scalloped portions 336 are cut at an angle to the plane of rotation, as shown in FIGS. 14*a*-14*b*. In particular, the angle of the sloping part of the scalloped portions should be substantially equal to the angle of the external casing in the region of the rotation wheel 28.

Figure 5A:
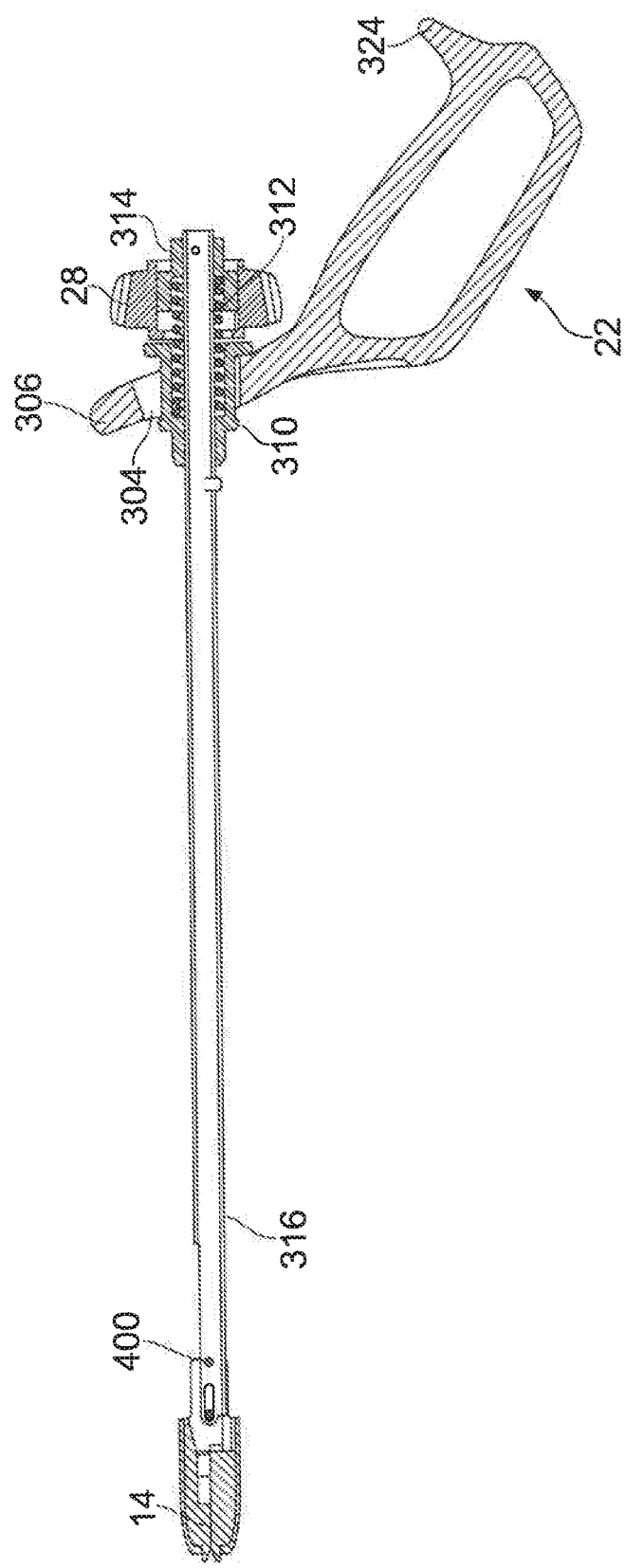
FIG. 5a is a sectional view of the clamping mechanism of the electrosurgical instrument of FIG. 3, shown in a closed configuration.
Figure 5B:
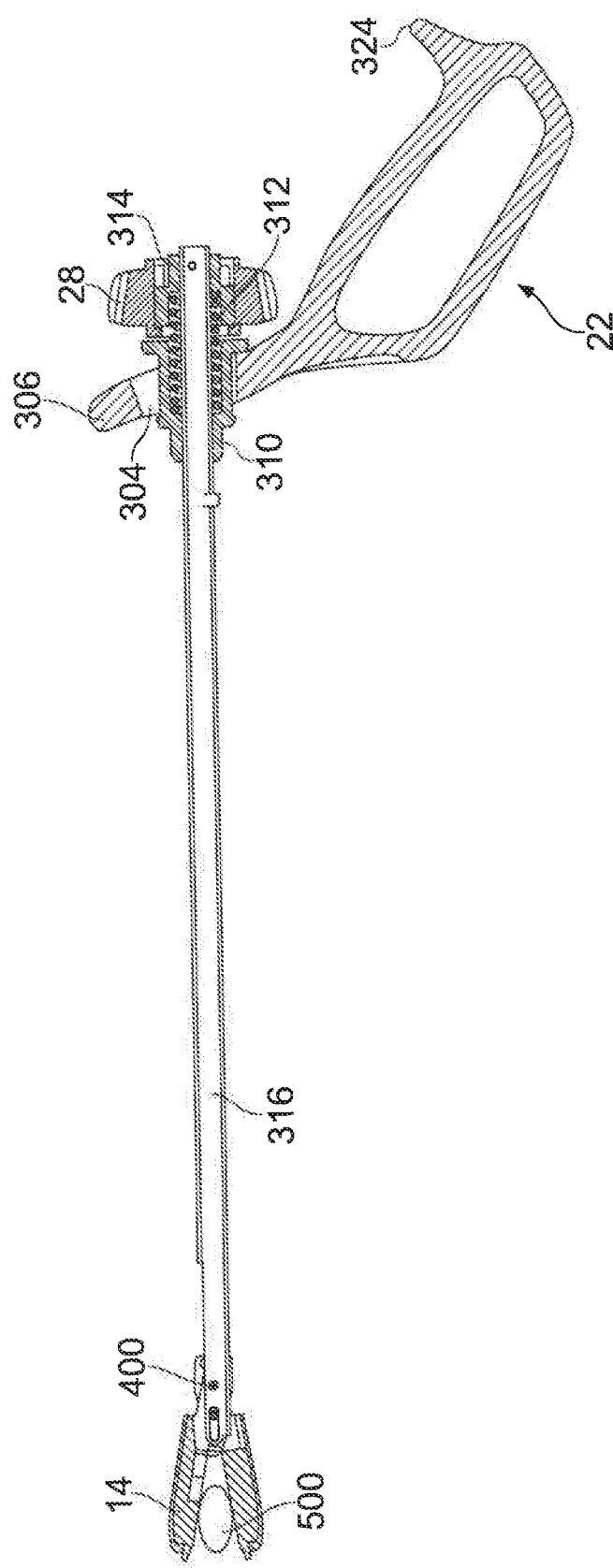
FIG. 5b is a sectional view of the clamping mechanism of the electrosurgical instrument of FIG. 3, shown in a closed configuration with tissue clamped therebetween.
Figure 15A:
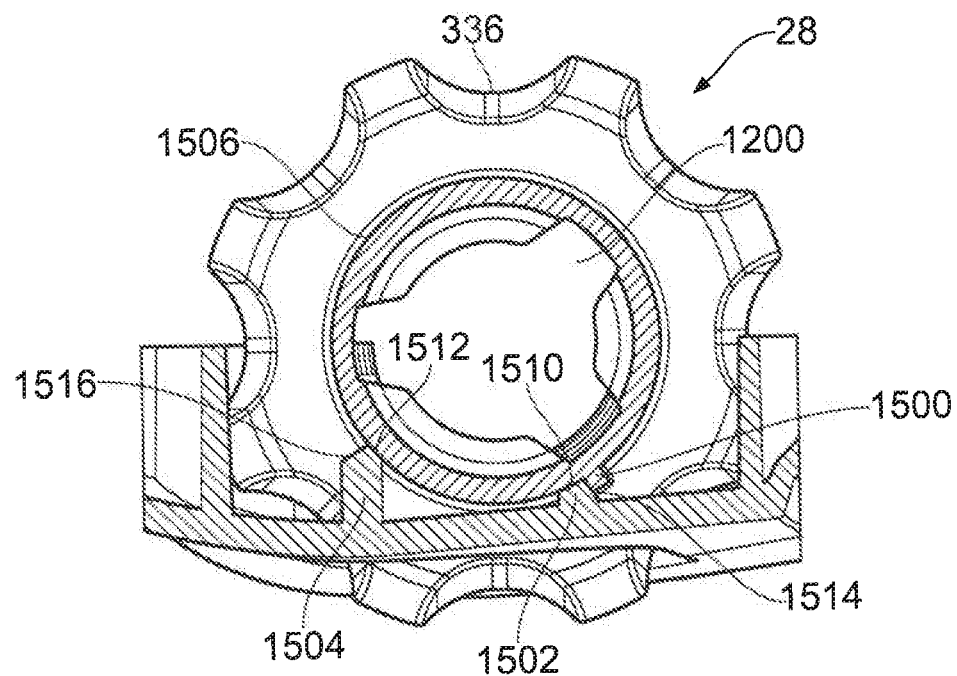
FIGS. 15a-15b illustrate the rotational movement of the blade angle control wheel of the electrosurgical instrument of FIG. 3.
Figure 15B:
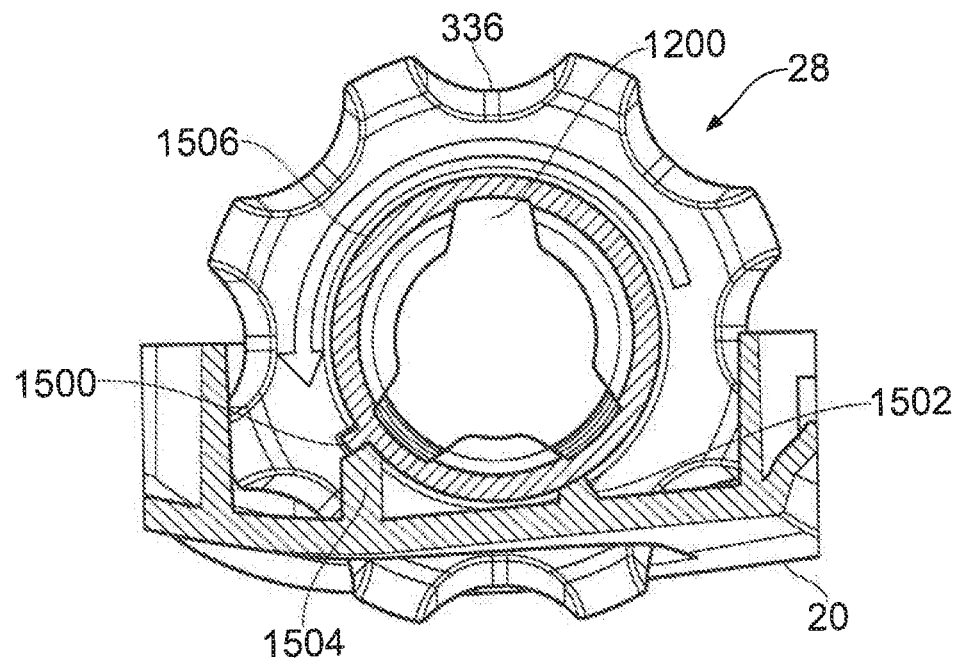
Figure 16A:
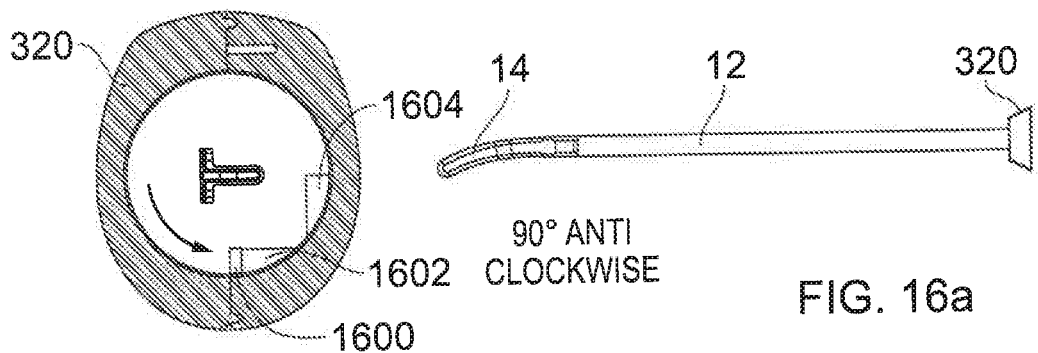
FIGS. 16a-16d illustrate the rotational movement of the end effector of the electrosurgical instrument of FIG. 3.
Figure 16B:
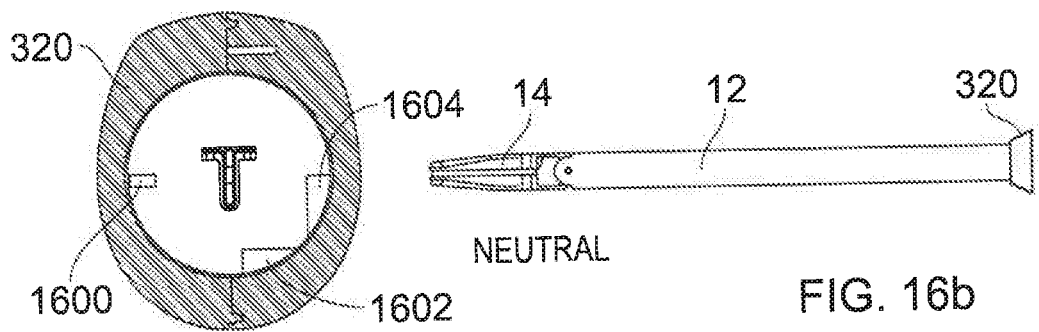
Figure 16C:
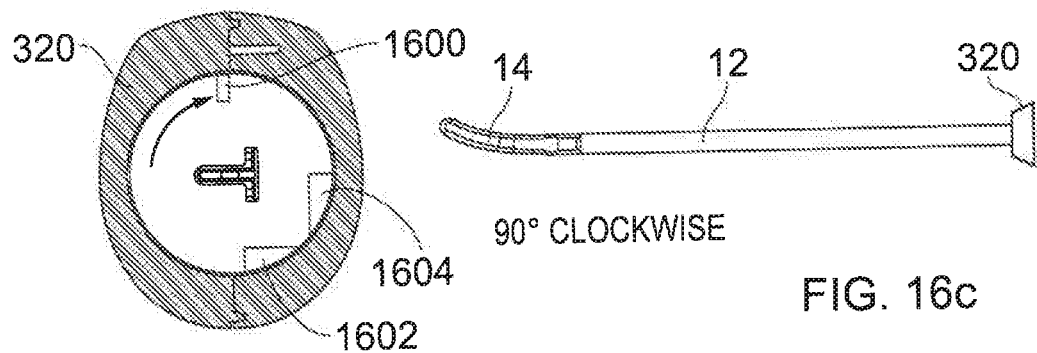
Figure 16D:
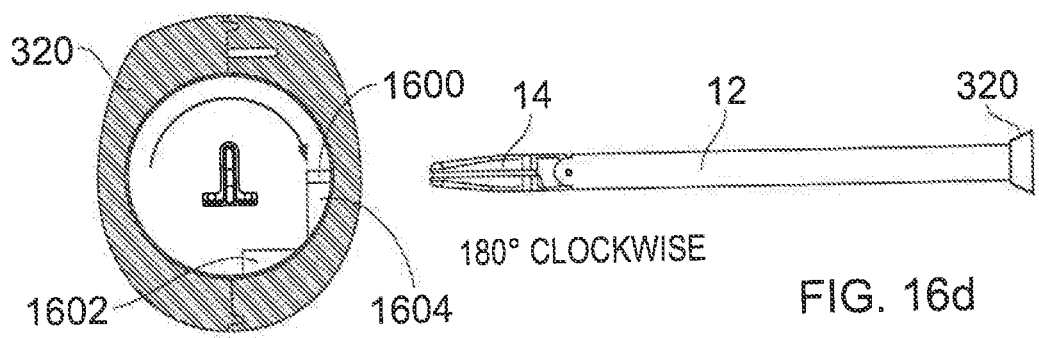

The rotation wheel 28 also comprises at least one stop member 1500 for limiting the degree of rotation, as illustrated in FIGS. 5*a*-5*b*. The stop member 1500 interacts with stop features 1502, 1504 integral to the casing 20. As the rotation wheel 28 is rotated, the stop member 1500 is obstructed by the stop features 1502, 1504, thereby preventing further rotation. For example, the stop features 1502, 1504 may limit the rotation wheel to 270° of rotation. Similarly, the shaft moulding 320 also comprises a stop member 1600 that interacts with stop features 1602, 1604 integral to the casing 20, as shown by FIGS. 16*a*-16*d*. The stop member 1600 of the shall moulding 320 and its respective stop feature 1602, 1604 are radially aligned with the stop member 1500 of the rotation wheel 28 and its respective stop features 1502, 1504 such that rotation is limited to the same extent. That is, as the rotation wheel 28 is turned, the radial point at which stop member 1500 on the rotation wheel 28 is obstructed will be the same as the radial point at which stop member 1600 on the shaft moulding 320 will be obstructed. For example, in FIGS. 15*b* and 16*a*, the jaws 14 have been rotated 90° anticlockwise from a neutral orientation (shown in FIG. 16*b*). This rotational freedom means that the user can grasp at tissue from different angles without needing to rotate the whole instrument 1.

Figure 17:
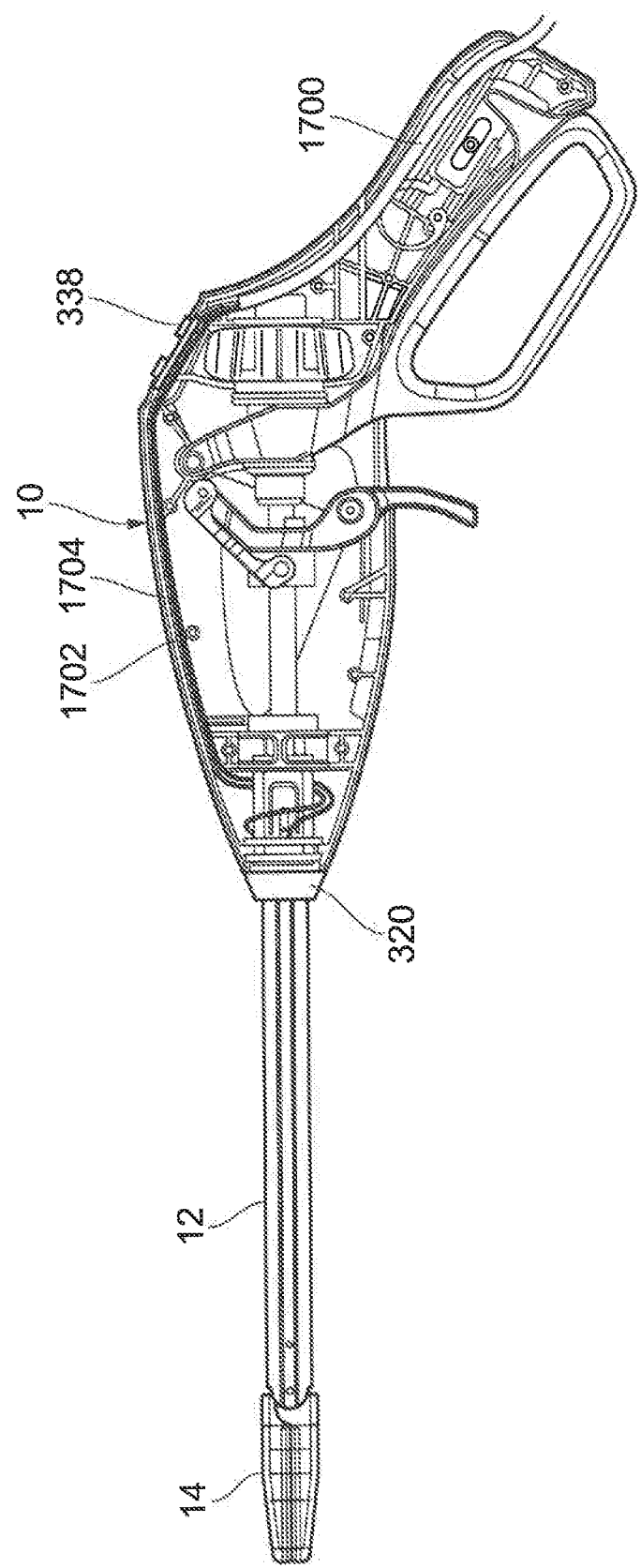
FIG. 17 is a sectional view of the electrosurgical instrument of FIG. 3 illustrating a wiring path.
Figure 18A:
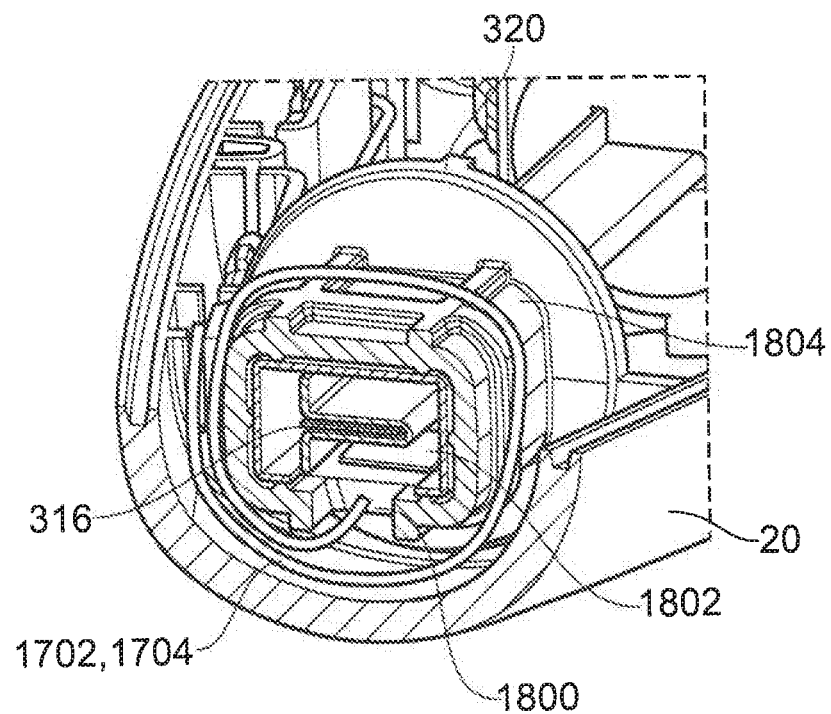
FIGS. 18a-18b show further details of an electrical wiring path used in the electrosurgical instrument of FIG. 3.
Figure 18B:
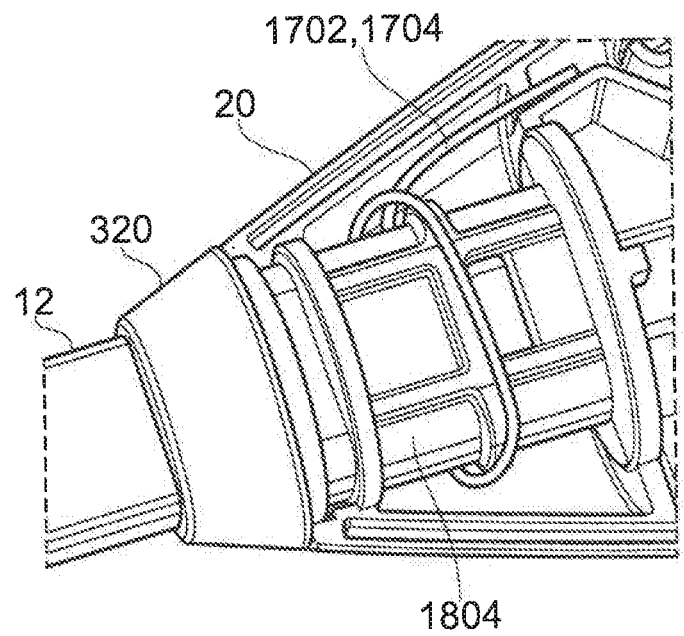
Figure 19:
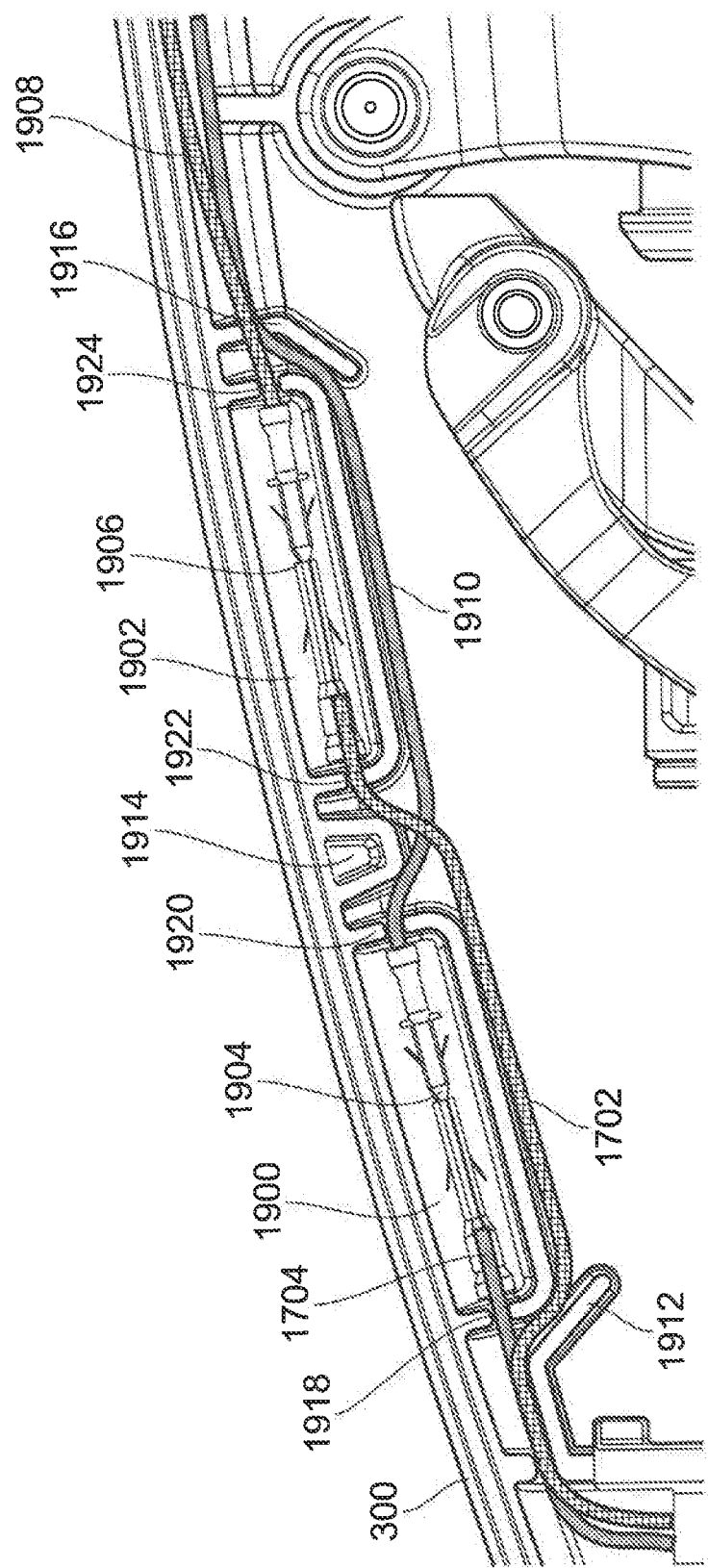
FIG. 19 shows further details of an electrical wiring path used in the electrosurgical instrument of FIG. 3.

As described above, the switch button 26 is provided for activating and de-activating the RF signal delivered to the electrodes in the jaws 14 via some appropriate circuitry, for example, two ingress-protected switches on a small printed circuit board (PCB) 338. As shown in FIG. 17, the PCB 338 is connected to a connection cord 1700 for receiving the RF output from a generator (not shown) and electrical wiring 1702, 1704 for supplying the RF current to the electrodes in the jaws 14, for example, one wire for the active electrode and one for the return electrode. As shown in FIG. 17 and FIGS. 18*a*-18*b* the wires 1702, 1704 are wrapped underneath and around the shaft moulding 320 before entering a guide slot 1800 into the internal cavity 1802 of the shaft moulding 320 and down the outer shaft 12. Wrapping the wires 1702, 1704 around the shaft moulding 320 in this way keeps the wires 1702, 1704 in a compact arrangement, so as to enable easy assembly, whilst allowing for the rotation of the drive shaft 316. In this respect, the wires 1702, 1704 un-wind and re-wind with the rotation of the drive shaft 316. Additionally, one of the clamshell mouldings 300 also comprises two moulded pockets 1900, 1902 located in series for housing the wire contacts 1904, 1906 that connect the active and return wires 1702, 1704 to the wiring 1908, 1910 of the ingress-protected switches 338. The opposite clamshell moulding 302 comprises corresponding rib features (not shown) to retain the contacts 1904, 1906 within the pockets 1900, 1902. As a result, the two wire contacts 1904, 1906 are longitudinally separated such that only one contact can pass through each pocket 1900, 1902, thereby providing a physical barrier between each contact 1904, 1906 and any wiring. This prevents the risk of insulation damage to any of the wiring caused by the contacts 1904, 1906, whilst also protecting the contacts 1904, 1906 themselves from any fluid that may make its way down the outer shaft 12 and into the casing 20.

Figure 20:
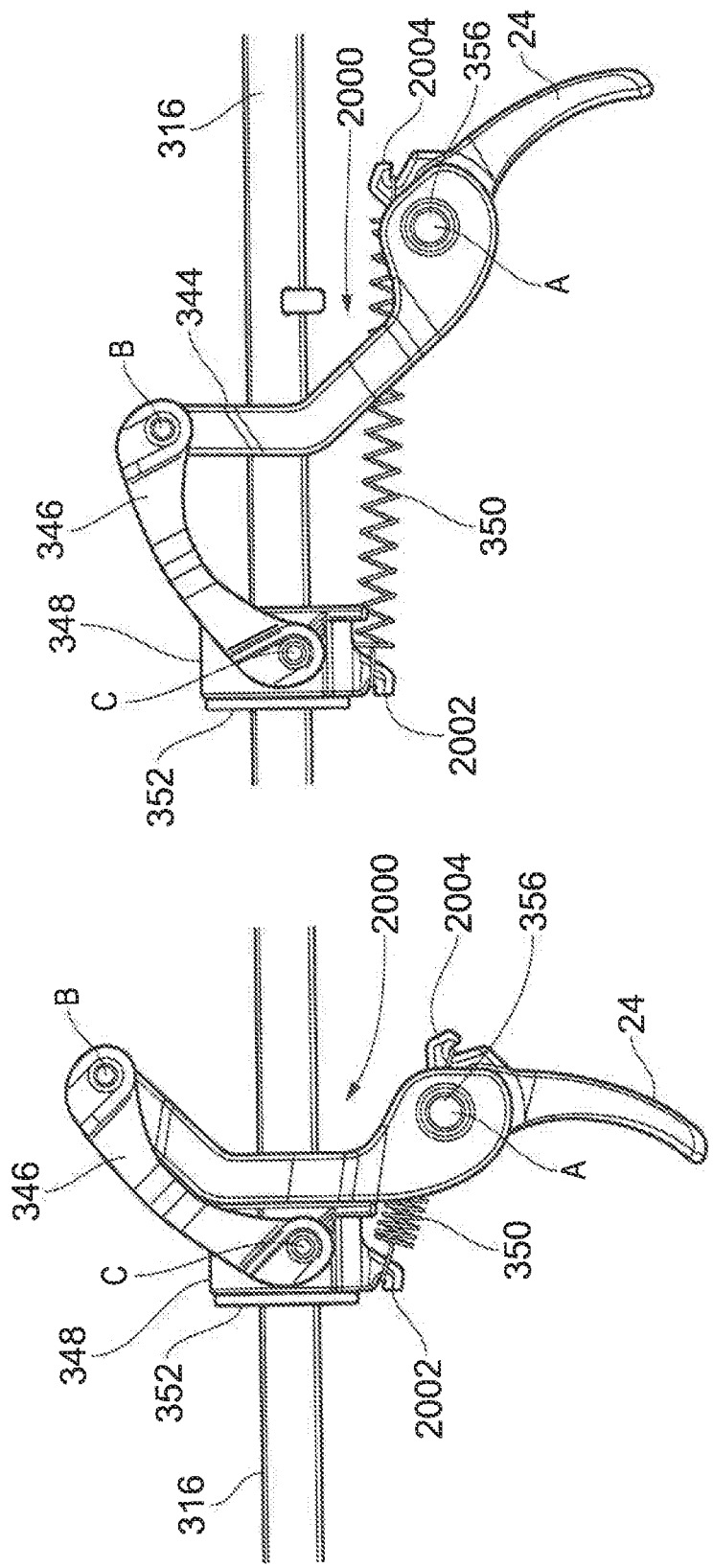
FIGS. 20a-20b are side views of part of the cutting mechanism of the electrosurgical instrument of FIG. 3.

Turning to the cutting mechanism, a blade 340 for cutting tissue clamped between the jaws 14 is provided within a central track 342 along the length of the drive shaft 316. The mechanism for actuating the blade 340 along the track 342 and between the jaws 14, is operated via the trigger 24. The trigger 24 actuates a drive assembly formed of a trigger moulding 344, a blade drive moulding 346, a blade collar moulding 348, an extension spring 350 and a blade moulding 352. The drive assembly is positioned between the shaft moulding 320 and the handle collar 304 of the clamping mechanism. As shown in FIGS. 20*a*-20*b*, the drive assembly functions as an offset slider-crank mechanism whereby the force exerted by the user on the trigger 24 is transferred into axial movement of the blade moulding 352 along the drive shaft 316, which in turn drives the attached blade 340.

Figure 21:
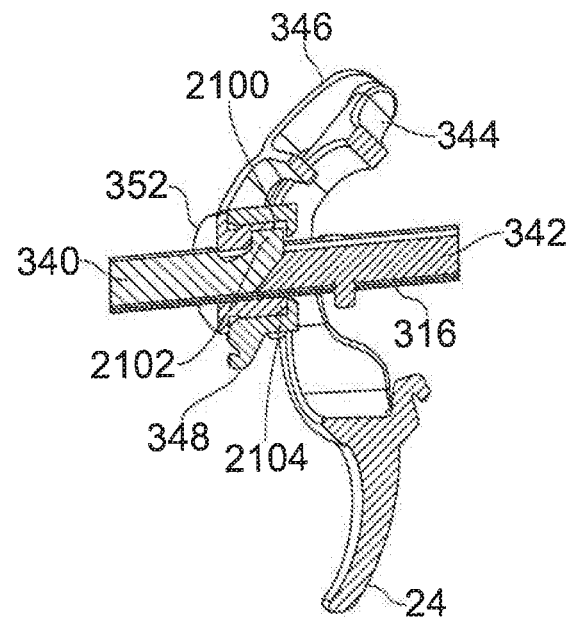
FIG. 21 is a sectional view of part of the cutting mechanism of the electrosurgical instrument of FIG. 3.
Figure 22:
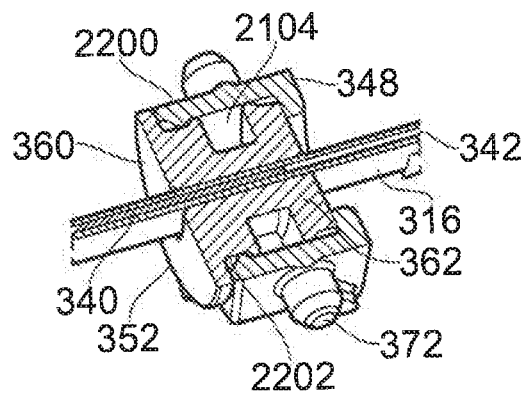
FIG. 22 is a sectional view of another part of the cutting mechanism of the electrosurgical instrument of FIG. 3.
Figure 23:
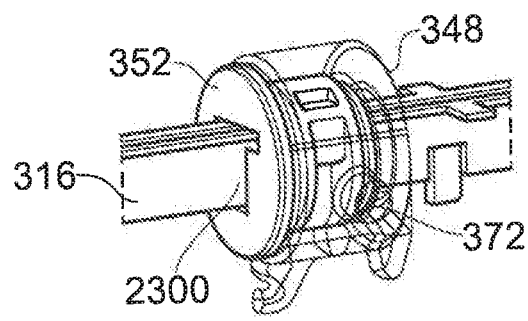
FIG. 23 is a partially transparent perspective view of part of the cutting mechanism of the electrosurgical instrument of FIG. 3.

As shown in FIGS. 21, 22 and 23, the blade moulding 352 is arranged to sit within the blade collar moulding 348. As shown in FIG. 22, the blade collar moulding 348 comprises a lip 2200 the interlocks with a groove 2202 around the circumference of the blade moulding 352. As shown on FIG. 23, the blade moulding 352 has a "T" shaped aperture 2300 for receiving the drive shaft 316 and blade 340. The blade moulding 352 further comprises an internal cut-out 2100, as shown by FIG. 21, for the proximal end of the blade 340, wherein the end of the blade 2102 is shaped to match the internal cut-out 2100 of the blade moulding 352 so as to allow ease of assembly, as demonstrated by FIGS. 24a-24c. The blade moulding 352 is isolated rotationally from the blade collar moulding 348 such that the two mouldings can rotate concentrically. Consequently, the blade moulding 352 is able to rotate with the drive shaft 316.

Figure 47A:
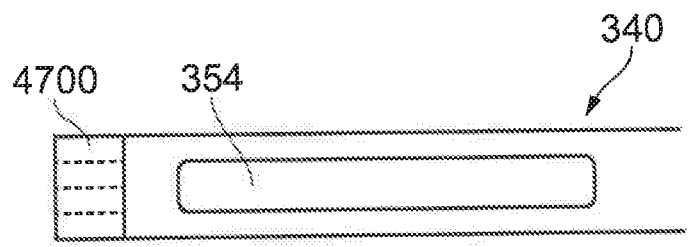
FIGS. 47a-47e illustrate the distal end of the cutting blade used in the electrosurgical instrument of FIG. 3.
Figure 47B:
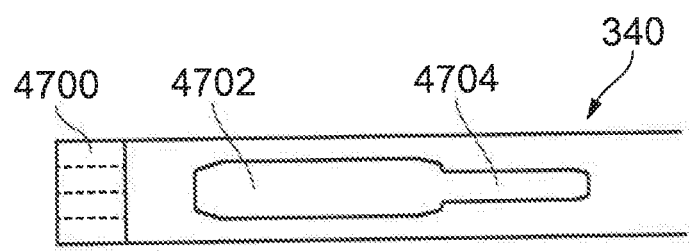
Figure 47C:
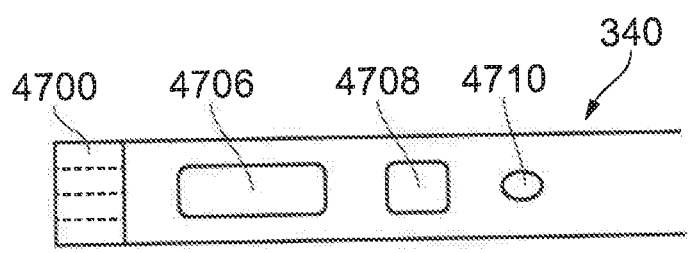
Figure 47D:
Figure 47E:
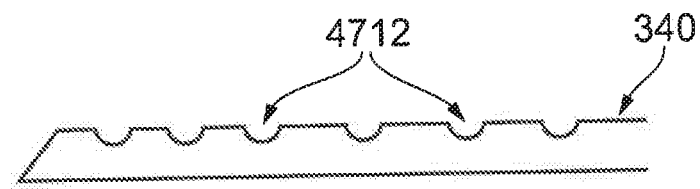

As described above, the jaws 14 may be curved. To enable the blade 340 to be pushed around the curve, whilst maintaining sufficient cutting ability, the frictional force of the cutting blade 340 through the curved track must be minimised. The frictional force is a product of the frictional coefficient of the blade 340 within the track 342, and the force due to bending that the blade 340 exerts on the walls of the track 342. This frictional force may be reduced, for example, by adding a low friction coating to the sides of the blade, and/or preferentially weakening the blade 340 to graduate the flexibility of the blade's distal end such that it is able to bend along the track 342 whilst remaining rigid in the direction of the cutting force. Preferential weakening may be provided, for example, by the provision of one or more apertures 354 in the distal end, as shown in FIG. 3 and FIGS. 47a-47c, or by graduating the blade 340 thickness, as illustrated in FIG. 47d. Alternatively, as illustrated by FIG. 47e, patterned laser cuts 4712 or chemical etches in the distal end could be used to control the bending stiffness over a length of the blade, whereby the spacing between such cuts may be constant or gradually increase from the distal to proximal end.

Figure 10B:
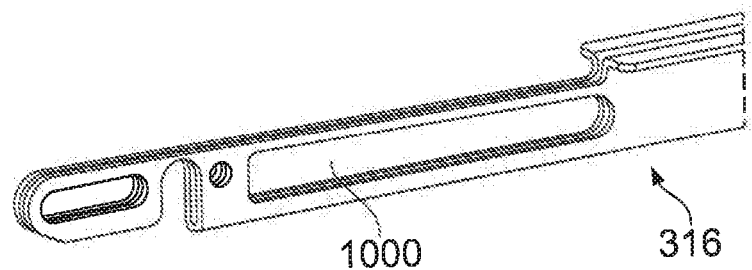
Figure 10C:
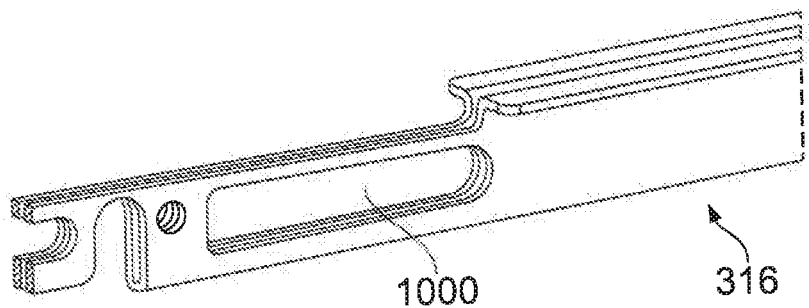

In use, blood and tissue can build up within the distal end of the instrument particular, blood and tissue can cause the blade 340 to stick within the drive shaft 316. Therefore, the distal end of the drive shaft 316 may include cut-out portions 1000, 1002 in order to reduce the surface area of the drive shaft 316 to which blood and tissue build stick, as shown in FIGS. 10b-10c. For example, the cut-out portions may be such that the distal end comprises two side walls with no base support, or the distal end comprises a base support with bifurcated side walls.

2. OPERATION OF THE INSTRUMENT

Having described the overall configuration of the device, the overall operation of the electrosurgical instrument 1 in use will now be discussed. Following this, further detailed description of the configuration and operation of particular aspects of the device will be undertaken.

As discussed above, the handle 10 of the electrosurgical instrument is arranged to i) clamp tissue between a set of jaws 14, ii) latch the jaws in place (if desired by the user), iii) deliver an RF signal to electrodes in the jaws 14 so as to coagulate the tissue clamped between, and iv) launch a blade 340 between the jaws 14 so as to cut the tissue clamped between. The handle 10 can also rotate the jaws 14 so as to allow the user to clamp tissue at different angles without needing to rotate the entire handle 10. The result is that the tissue between the jaws can be sealed prior to or at the same time as being cut by the same electrosurgical instrument. Moreover, these effects can be achieved by the instrument via a one handed operation thereof by the surgeon.

2.1 Clamping Mechanism

Figure 4:
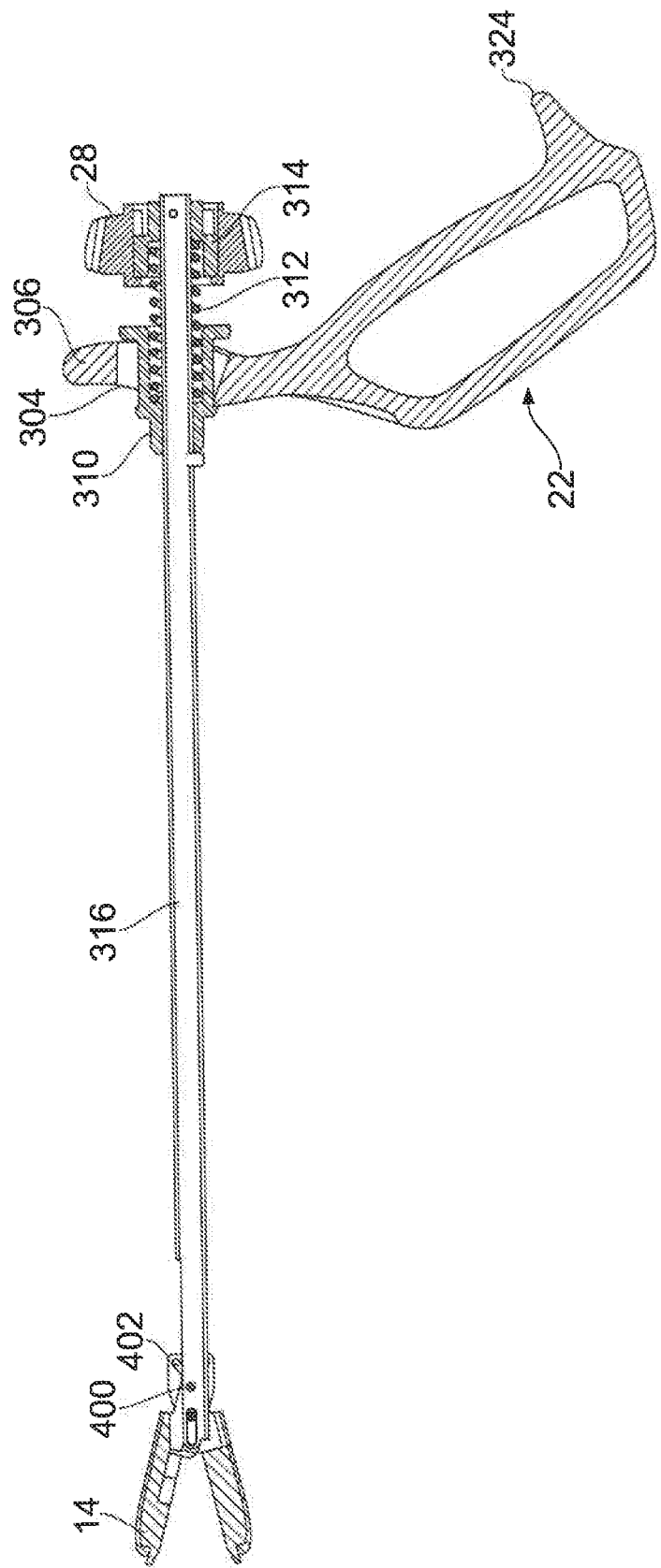
FIG. 4 is a sectional view of the clamping mechanism of the electrosurgical instrument of FIG. 3, shown in an open configuration.

To clamp tissue between the jaws 14, the user squeezes the clamping handle 22 towards the proximal end 328 of the casing 20 until the latch 324 engages with the latch moulding 326 within the casing 20. This movement pivots the drive handle 22 about its hinge 306, as shown by FIGS. 8e-8f, and pushes the edge of the collar 304 against the flange 800 to drive the collar moulding 310, the spring and the inner moulding 314 along the drive shaft 316 in the proximal direction, as illustrated by FIGS. 4 and 5a. As described above, the inner moulding 314 is attached to the drive shaft 316 via protruding members 602. Therefore, as the inner moulding 314 is pushed back axially, the drive shaft 316 is also moved axially which drives the pin 400 in the cam slot 402 of the jaws 14, thereby closing the jaws 14. As such, the load from the drive handle 22 is transferred to the drive shaft 316 via the spring mechanism of the collar moulding 310, spring 312 and inner moulding 314.

Once tissue is clamped between the jaws 14, as shown by FIG. 5b, the spring 312 acts to limit the force loaded onto the tissue. Once the collar moulding 310, spring 312 and inner moulding 314 have stopped moving axially, and as the collar 304 continues to drive against the flange 800, the threshold compression force on the spring 312 is eventually reached such that the spring 312 begins to compress between the collar moulding 310 and inner moulding 314. As the spring 312 compresses further, the drive handle 22 can be driven all the way into the latched position without exerting any more force on the clamped tissue. That is, the load of the drive handle 22 is no longer transferred to the drive shaft 316, but is effectively absorbed by the spring 312. As such, the spring 312 ensures that the correct amount of load is transferred onto the jaws 14. Without the spring 312, actuation of the drive handle 22 will continue to increase the load transferred to the drive shaft 316 and subsequently the jaws 14 and tissue. This could result in mechanical damage to the tissue as the user continues to squeeze the drive handle 22 in order to engage the latch 324.

As discussed above, the cavities 608, 610 in the collar moulding 310 and inner moulding 314 act together to allow for a larger spring 312. This allows for greater spring travel so that the spring 312 does not completely compress to its solid length during use. If the spring 312 was to reach its solid length, the spring would no longer absorb the load exerted by the drive handle 22 and the force would once again be transferred to the jaws 14.

2.2 Latch Mechanism

Figure 26A:
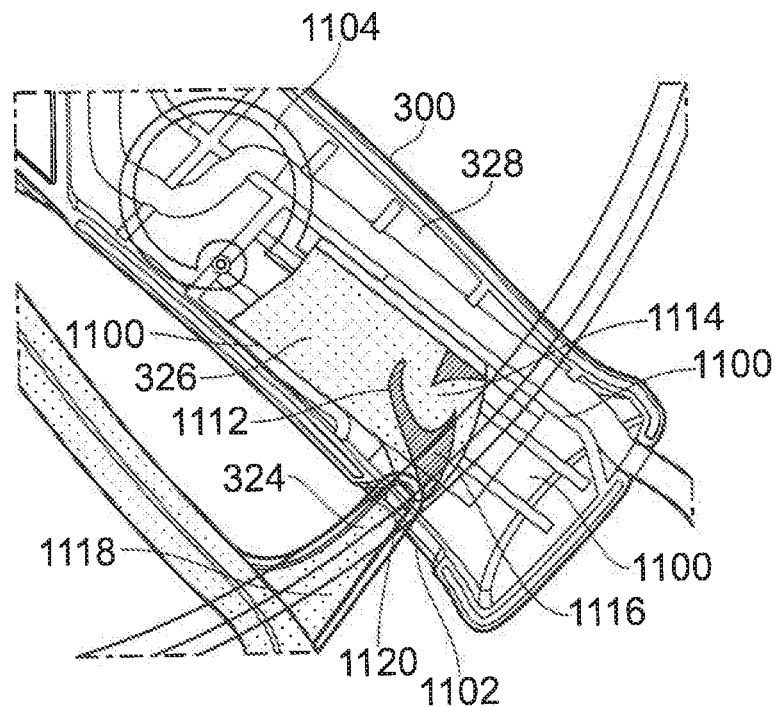
FIGS. 26a-26f are sectional views illustrating the operation of the latching mechanism of the electrosurgical instrument of FIG. 3.
Figure 26B:
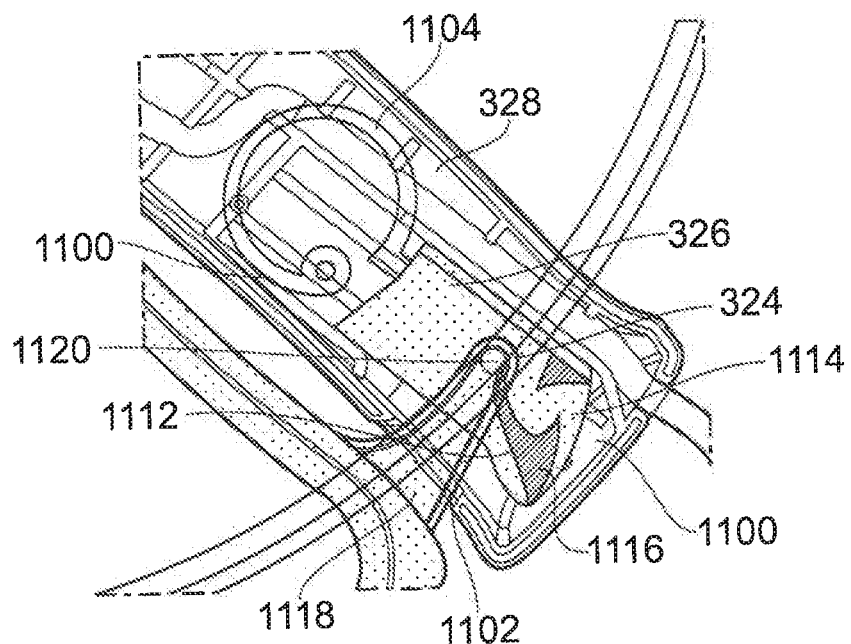
Figure 26C:
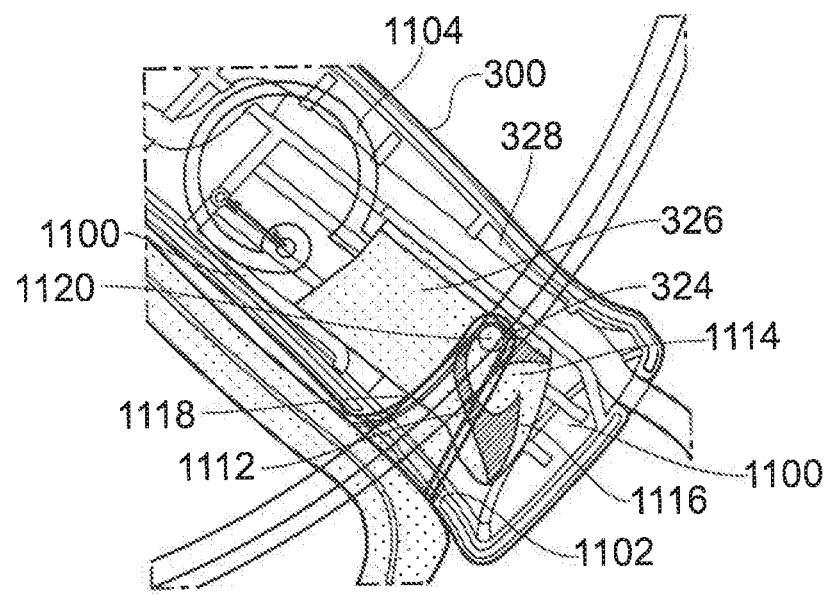
Figure 26D:
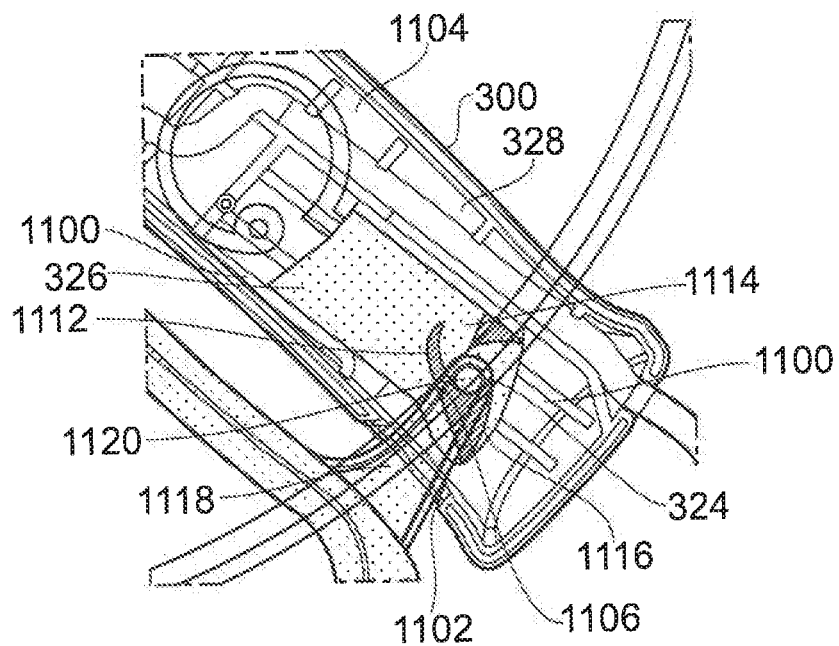

Once tissue has been clamped between the jaws 14, the jaws 14 can be locked into a closed position by engaging the latch 324 on the drive handle with the latch moulding 326 inside the casing 20 as shown by FIGS. 26a-26f. As the latch 324 enters the casing 20 via the opening 1102, the latch 324 engages the latch moulding 326, pushing the moulding 326 down within the casing 20 and thereby extending the spring 1104. As shown in FIGS. 26b-26c, the latch 324 runs up the side of the cam path 1106 until it reaches its maximum position. At this point, the drive handle 22 cannot be compressed any further, and the spring 1104 pulls the latch moulding 326 back up inside the casing 20 such that the latch 324 slots into the "V" shaped pocket of the cam path 1106 to retain the drive handle 22 in the compressed position and the jaws 14 in the closed position, as shown in FIG. 26d.

In this latched position, the user's hand is free for operating the other functions of the instrument 1, as will be discussed below.

Figure 26E:
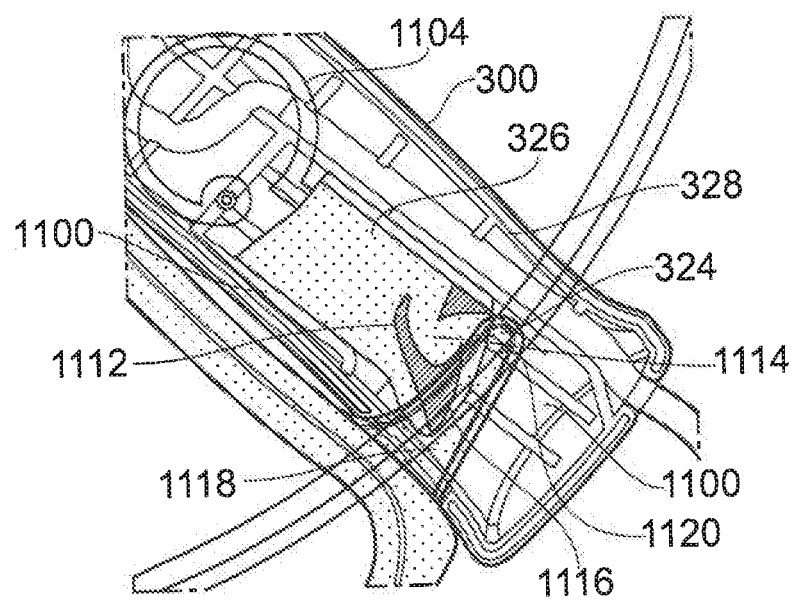
Figure 26F:
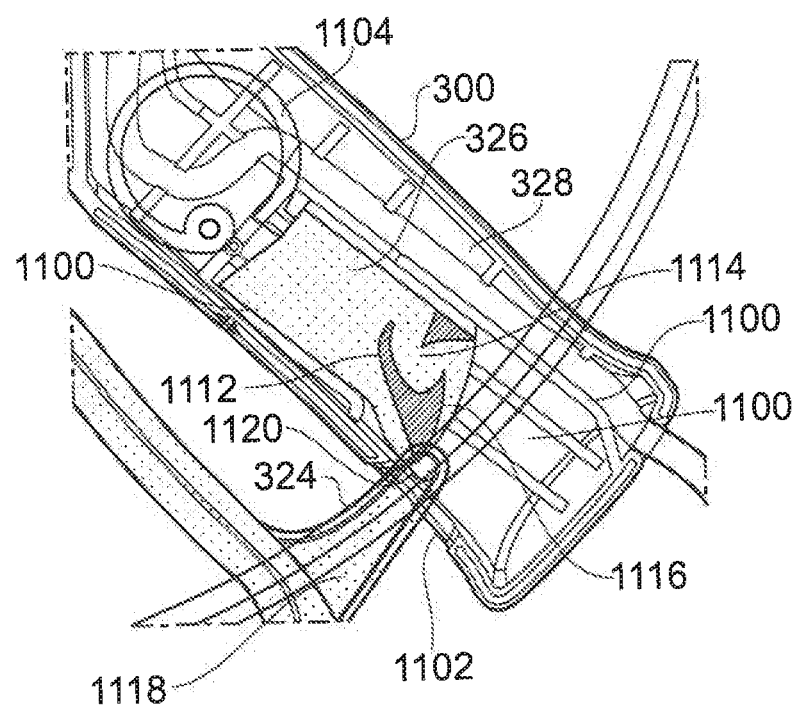

To release the latch 324 from the casing 20 and open the jaws 14, the user must squeeze drive handle 22 towards the casing 20 to release the latch 324 from the pocket of the cam path 1106, as shown by FIG. 26e. The force of the spring 1104 pulls the latch moulding 326 further up into the casing 20, such that the latch 324 travels in the opposite direction down the side of the cam path 1106, as shown by FIGS. 26e-26f, and back out of the opening 1102. The latch moulding 326 will then return back to its original position within the casing 20.

2.3 Cutting Mechanism

Whilst the jaws 14 are in a closed position, the user may need to cut the tissue clamped between. To cut the tissue, a blade 340 is driven between the jaws 14 by actuation of the drive assembly.

Figure 25C:
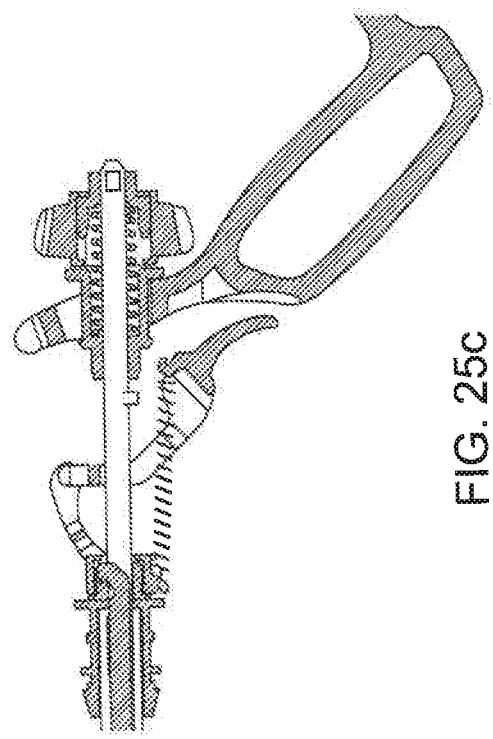
FIGS. 25a-25c are sectional views of the cutting mechanism and clamping mechanism of the electrosurgical instrument of FIG. 3.
Figure 25B:
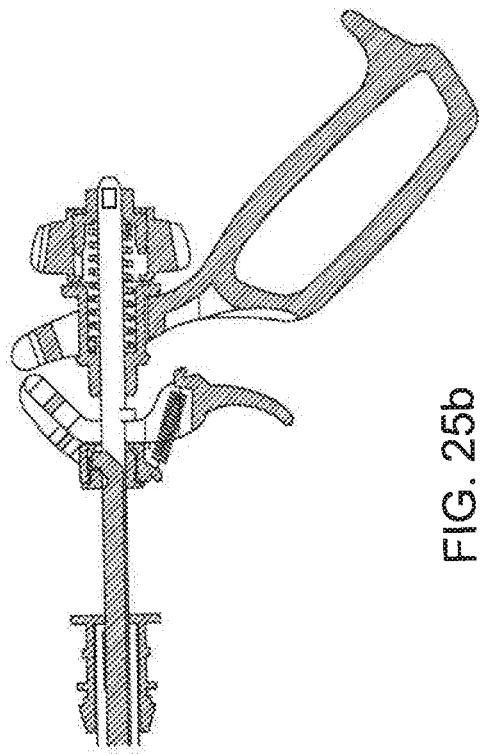
Figure 25A:
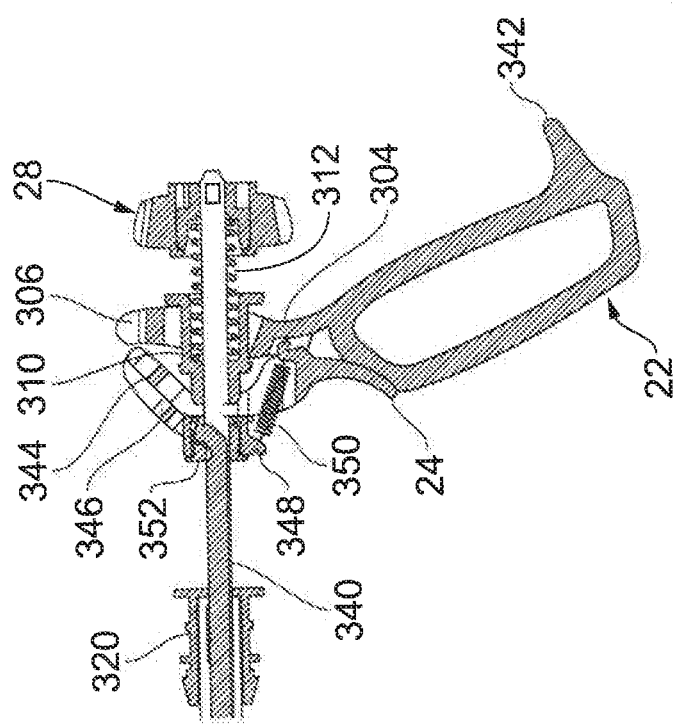

The drive assembly is a three pivot arrangement that acts as a slider-crank mechanism. As the user pulls the trigger 24 back towards the casing 20, as shown by FIGS. 25b-25c, it levers the trigger moulding 344 around a pivot point A which is anchored to the casing 20, for example, by means of outward facing pins 358 that connect with corresponding mouldings 356 integral to the clamshell mouldings 300, 302 shown in FIG. 3. This urges the pivot point B connecting the trigger moulding 344 and drive moulding 346 over its centre position, thereby driving the blade collar 348, blade moulding 352 and blade 340 along the drive shaft 316 at a force sufficiently high that the blade 340 is able to cut the clamped tissue. In this respect, the load exerted on the trigger 24 is transferred to the blade collar 348 and blade moulding 352 via the trigger moulding 344 and drive moulding 346. As the pivot point B moves over centre into its protracted position, the speed at which the blade collar 348 and blade moulding 352 are driven along the drive shaft 316 accelerates, thus increasing the force of the blade 340. As such, the force at which the blade 340 cuts into the tissue increases without the user exerting any additional force on the trigger 24.

The shaft moulding 320 acts as a stopping point for the blade collar 348 and blade moulding 352. Consequently, the pivot point B always remains above the two other pivot points A, C with respect to the drive shaft 316.

During actuation of the trigger 24, the force exerted on the trigger 24 is big enough to overcome the compression force of the extension spring 350 such that it extends along the same plane as the drive shaft 316 to allow for the axial movement of the blade collar 348 and blade moulding 352. On release of the trigger 24, the extension spring 350 re-compresses to retract the drive assembly to its original position. In this respect, the tension of the extension spring 350 is strong enough to retract the blade 340 through thick tissue without the need for user intervention.

2.4 Shaft Rotation

During use, the user may need to reach tissue from different angles without needing to move the entire instrument 1. Therefore, the jaws 14 are advantageously rotatable relative to the handle 10 by means of the rotation wheel 28. This is particularly beneficial where the jaws 14 are on a curved track, such as those shown in FIGS. 16a-16d. As described above, the rotation wheel 28 is coupled to the inner moulding 314 via interlocking members 1200, 1202 such that the inner moulding 314 rotates with the rotation wheel 28. As the end of the drive shaft 316 is connected to the inner moulding 314, the drive shaft 316 also rotates which subsequently rotates the jaws 14 at its opposite end.

To facilitate this rotational movement without interfering with the operation of the clamping mechanism, the collar moulding 310 is rotationally isolated within the handle collar 304 such that the collar moulding 310 also rotates with the drive shaft 316. Likewise, so as to allow drive shaft 316 rotation without interfering with the operation of the cutting mechanism, the blade moulding 352 is rotationally isolated within the blade collar 348.

In order to transfer the rotational movement to the outer shaft 12, the shaft moulding 320 is rotationally isolated within its socket 322. As described above, the shaft moulding 320 acts as a rotational guide so as to control the rotational movement relative to the shaft 316 along the entire length of the instrument 1. Additionally, the active and return wires 1702, 1704 are arranged within the casing 20 so as to prevent damage to these wires 1702, 1704 as a result of the rotating components. As described above, the wires 1702, 1704 are wrapped around the shaft moulding 320 so as to allow for the degree of rotation of the drive shaft 316. Consequently, the wires 1702, 1704 an and re-wind around the shaft moulding 320 as it rotates.

2.5 Electrode Activation

Whilst the jaws 14 are in a closed position, the user may wish to coagulate and seal the tissue clamped between. To do this, the user initiates electrode activation using the switch button 26 on the top of the casing 20, positioned conveniently so that the user can easily access the button 26 whilst using the device single handed. In doing this, an appropriate RF signal is delivered to the electrodes in the jaws 14 so as to coagulate and seal the tissue. The RF signal may be a pure or blended waveform, depending on the desired effect.

Having given an overview of the configuration and operation of the device as a whole, further detailed description of the configuration and operation of particular aspects thereof will now be given.

3. CLAMPING MECHANISM ASSEMBLY AND OPERATION

As described above, the proximal handle portion 10 of the electrosurgical instrument 1 includes a first mechanism for actuating one aspect of a distal end effector assembly 14 such that the end effector assembly 14 moves between a first and second condition. For example, the end effector assembly 14 may be a set of opposed jaws 14 arranged to open and close. The mechanism used to trigger movement of these jaws 14 is the so called clamping mechanism comprising a drive handle 22 and two barrel shaped mouldings 310, 314 with a spring 312 compressed therebetween, all of which are threaded along an elongate bar 316 that extends between the jaws 14 and the handle 10, as shown in FIGS. 4 and 5a-5b.

As shown in FIG. 8a, the drive handle 22 comprises a collar 304 in which the collar moulding 310 sits. The collar 304 comprises an aperture 318 shaped like a keyhole or a figure of eight. As such, the aperture 318 is formed of two contiguous apertures 804, 806, wherein the top aperture 804 has a larger diameter across it than the bottom aperture 806.

The collar moulding 310 is a cylindrical or barrel shaped component having two flange portions 800, 802 spaced apart longitudinally. The diameter of the proximal flange 800 is larger than both the upper and the lower apertures 804, 806. The diameter of the distal flange 802 is smaller than the upper aperture 804 and larger than the lower aperture 806.

During assembly, the collar moulding 310 is first inserted through the upper aperture 804, as shown by FIGS. 8b-8c. As the distal flange 802 is smaller than the upper aperture 804, it easily passes through, whereas the proximal flange 800 may be large enough to prevent the collar moulding 310 from advancing the entire way through the upper aperture 804. As shown by FIG. 8d, the collar 304 is then pushed upwards to engage the lower aperture 806 with the collar moulding 310.

Once assembled, the collar moulding 310 remains within the lower aperture 806 of the collar 304 and is positioned such that its two flanges 800, 802 lie either side of the collar 304, as shown in FIG. 8e. As lower aperture 806 has a smaller diameter than both flanges 800, 802, the collar moulding 310 cannot be removed by simply pushing the collar moulding 310 through the lower aperture 806. In contrast, the body of the collar moulding 310 between the two flanges 800, 802 has a slightly smaller diameter than the lower aperture 806. Therefore, the collar moulding 310 sits within the lower aperture 808 loosely enough to allow rotational movement.

As can be seen from FIG. 8e, the longitudinal distance between the two flanges 800, 802 is only slightly larger than the thickness of the collar 304 such that the collar 304 sits snugly between the flanges 800, 802. This ensures that movement of the drive handle 22 is transferred directly to the collar moulding 310 and subsequently to the other components of the clamping mechanism. This is particularly important for ensuring that the jaws 14 are responsive to the movement of the drive handle 22 and that there is not a delayed response between actuation of the drive handle 22 and movement of the jaws 14.

Once the collar moulding 310 and drive handle 22 have been assembled, the remaining components can be assembled.

The drive shaft 316 is an elongated bar with one or more protruding members 602 located at its proximal end, as shown in. FIG. 6. The protruding members 602 are flexible tabs that fan out from the surface of the drive shaft 316. That is to say, the protruding members 602 are deformable such that they may be pressed flush against the surface of the drive shaft 316, but will return to their original positions upon release of any resistive force. This allows the drive shaft 316 to be easily threaded through all of the components of the clamping mechanism during assembly, as will now be described.

The collar moulding 310 has an internal cavity divided into two parts. The first part is a narrow channel or slot 607 for receiving the drive shaft 316, wherein the distal end of the collar moulding 310 comprises an opening 311, as shown in FIG. 3, which matches the cross-sectional "T" shape of the drive shaft 316. The diameter of the channel 607 is only slightly wider than that of the drive shaft 316 so as to provide a snug fit for stability. On insertion of the drive shaft 316, the protruding members 602 are pressed flat to allow the drive shaft to be pushed all the way through.

The second part is a chamber 608 large enough to house one end of the spring 312. The chamber 608 can extend over any suitable proportion of the length of the collar moulding 310. For example, the length of the chamber 608 may be around 25% of the length of the collar moulding 310, or as much as 75% of the length of the collar moulding 310.

The chamber 608 is substantially larger than the collar moulding channel 607 such that as the drive shaft 316 is pushed through the collar moulding 310, the protruding members 602 span back out to their original configuration when they reach the chamber 608.

The collar moulding 310 and drive handle 22 assembly is threaded down along the drive shaft 316 until the collar moulding 310 reaches a second set of protruding members 600. These protruding members 600 have a span wider than the opening 311 on the collar moulding 310 so as to provide an obstruction that prevents the collar moulding 310 from advancing further along the drive shaft 316. As such, the protruding members 600 must be sufficiently rigid that the collar moulding 310 cannot be pushed passed the protruding members 600 by exerting some force or pressing the protruding members 600 inwards.

The drive shaft 316 is then threaded through the centre of the spring 312. Preferably, the spring 312 has a diameter that is only slightly larger than that of the drive shaft 312 to provide a close fit between the spring 312 and the drive shaft 316. The spring 312 is then pushed along the drive shaft 316 until the end of the spring 312 fills the collar moulding chamber 608.

The inner moulding 314 is a cylindrical or barrel shaped component having an internal cavity divided into two sections. The first section is a chamber 610 in which one end of the spring 312 is housed such that the spring 312 is partially encased by the collar moulding 310 and inner moulding 314. The second section is a narrow channel or slot 603 for receiving the proximal end of the drive shaft 316. The channel 603 is divided into two parts 604, 606. The first part of the channel 604 is shaped so as to allow the drive shaft 316 to be passed through, the flexible tabs 602 being pressed flat in doing so. As such, the diameter of the first channel part 604 is only slightly wider than that of the drive shaft 316 so as to provide a snug fit. The snug fit of the drive shaft 316 within both the collar moulding channel 607 and inner moulding channel 603 means that the drive shaft 316 is held firmly in place. This adds to the stability of the drive shaft 316 within the casing 20, which is particularly important for ensuring maximum control of the end effector 14.

The second part of the channel 606 provides a shoulder 605 into which the protruding members 602 can extend. Consequently, as the drive shaft 316 passes through the channel 604 and into the second channel part 606, the flattened protruding members 602 fan back out to their original decompressed positions. Once the protruding members 602 have engaged with the shoulder 605 of the second channel part 606, the drive shaft 316 cannot be pulled back through the first channel part 604 and is thus retained in the inner moulding 314. As such, the diameter of the second channel part 606 must be sufficiently wide that the protruding members 602 are able to expand beyond the diameter of the first channel part 604. To achieve this snap-fit connection, a protruding member 602 is only required on one side of the drive shaft 316.

This snap-fit connection is such that any axial movement of the inner moulding 314 will be transferred to the drive shaft 316. Similarly, any rotational movement of the inner moulding 314, for example, by means of the rotation wheel 28 formed around the inner moulding 314, is also transferred to the drive shaft 316.

Therefore, to complete the assembly of the clamping mechanism, the drive shaft 316 is simply threaded through the collar moulding 310, the spring 312 and finally the inner moulding 314, until the protruding members 602 snap into the second channel part 606.

Once assembled along the drive shaft 316, the collar moulding 310, the spring 312 and the inner moulding 314 are arranged such that the spring 312 is partially encased by the collar moulding 310 and inner moulding 314. By providing the collar moulding chamber 608 and inner moulding chamber 610 in which a substantial portion of the spring 312 can be housed, a longer spring 312 can be used without using up any additional space within the handle 10. As such, the larger the collar moulding chamber 608 and inner moulding chamber 610, the longer the spring 312. Furthermore, the distance between the protruding members 600, 602 means that the ends of the spring 312 are compressed by the end walls 612, 614 of the collar moulding chamber 608 and inner moulding chamber 610 respectively so that the spring 312 experiences an initial pre-compression upon installation. This is important for ensuring that when the handle 22 is actuated so as to activate the clamping mechanism, the correct load is applied to the jaws 14.

Figure 13A:
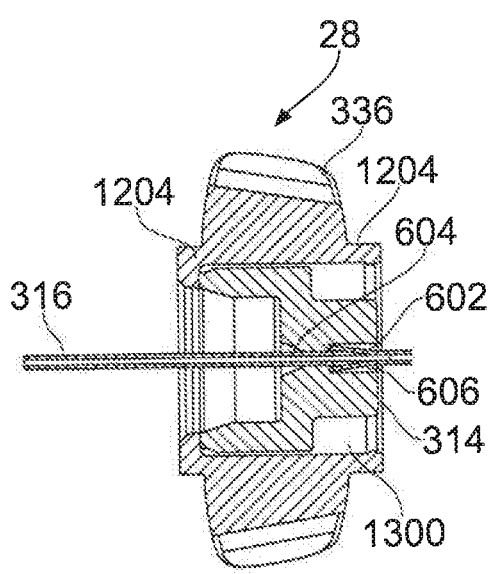
FIGS. 13a-13b are sectional views of the blade angle adjustment part of the electrosurgical instrument of FIG. 3.
Figure 13B:
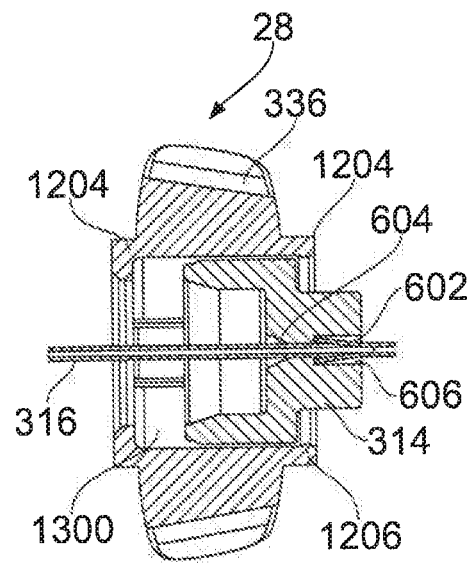

Additionally, the inner moulding 314 may be contained within a further barrel shaped moulding such as the rotation wheel 28 shown in FIGS. 13a-13b. Here, the inner moulding 314 rotates with the rotation wheel 28, but is free to move axially within the internal cavity 1300 of the rotation wheel 28, moving between a first position as shown in FIG. 13a and a second position as shown in FIG. 13b. Consequently, rotation of the wheel 28 rotates the inner moulding 314, which in turn rotates the drive shaft 316 and the jaws 14.

Once all of the components have been assembled, the drive handle 22 can be installed inside the casing 20. In this respect, the drive handle 22 is connected to the easing at its hinge 306. For example, the hinge 306 may be two outwardly extending pins that mate with corresponding hinge mouldings 308 integral to the clamshell mouldings 300, 302. This provides an anchor point around which the drive handle 22 can rotate.

Therefore, the above arrangement provides a mechanism for actuating the end effector assembly 14 which can be assembled easily and securely without the need for any additional components.

In use, the user squeezes the drive handle 22 towards the proximal end 328 of the casing 20, thereby rotating the drive handle 22 about its hinge 306. In doing this, the collar 304 pushes against the proximal flange 800, thus moving the collar moulding 310 longitudinally. This longitudinal movement drives the spring 312, inner moulding 314 and the drive shaft 316 back towards the proximal end of the handle portion 10, as shown by FIG. 5a. As the drive shaft 316 is coupled to the jaws 14, for example, by means of a pin 400 and cam slot 402 arrangement, the jaws 14 are moved from the open to the closed position. As such, the load from the drive handle 22 is transferred to the drive shaft 316 via the spring mechanism of the collar moulding 310, spring 312 and inner moulding 314. This spring mechanism is particularly important as it acts to limit the force loaded onto any tissue that is clamped between the jaws 14.

As the drive handle 22 is squeezed, the collar moulding 310, spring 312 and inner moulding 314 continue to move axially until either the inner moulding 314 reaches its furthest proximal position such that the jaws 14 are fully closed, as shown in FIG. 5a, or the jaws 14 are unable to close any further due to tissue 500 clamped between, as shown by FIG. 5b, in which case the drive handle 22 has not been fully actuated such that it is held in place by the latch 324. As the user continues to squeeze the drive handle 22 and the collar 304 continues to drive against the flange 800, the threshold compression force on the spring 312 is eventually reached such that the spring 312 begins to compress between the collar moulding 310 and inner moulding 314, as can be seen in FIG. 5b.

As the spring 312 compresses further, the drive handle 22 can be driven all the way into the latched position without exerting any more force on the clamped tissue 500. That is, the load of the drive handle 22 is no longer transferred to the drive shaft 316, but is effectively absorbed by the spring 312. As such, the spring 312 ensures that the correct amount of load is transferred onto the jaws 14. Without the spring 312, actuation of the drive handle 22 will continue to increase the load transferred to the drive shaft 316 and subsequently the jaws 14 and tissue 500. This could result in mechanical damage to the tissue 500 as the user continues to squeeze the drive handle 22 in order to engage the latch 324.

Therefore, the pre-compression of the spring 312 is important for ensuring that the spring 312 bears the load of the handle 22 as soon as the inner moulding 314 reaches its axial limit. Similarly, having a longer spring 312 allows for greater spring travel so that the spring 312 does not completely compress to its solid length during use. If the spring 312 was to reach its solid length, the spring 312 would no longer absorb the load exerted by the drive handle 22 and the three would once again be transferred to the jaws 14.

To retain the jaws 14 in the closed position, the latch 324 on the drive handle 22 must be engaged with the latch moulding 326 inside the proximal end 328 of the casing 20, as shown in FIGS. 26a-26f.

As shown in FIG. 11, the latch moulding 326 is a single integrally moulded component comprising a body portion 1108, a spring element 1104 and a cam path 1106. The proximal end 328 of the casing 20 has parallel walls 1100 that define a channel 1110 in which the body portion 1108 sits. The width of the channel 1110 is such that the body portion 1108 is retained within the channel 1110 but is still able to slide up and down the channel 1110 during use, as will be described below. In this respect, the latch moulding 326 is preferably made of a low friction material, for example, polytetrafluoroethylene (PTFE), to allow the body portion 1108 to easily slide within the channel 1110 without sticking. For further stability within the channel 1112, a moulded pin 330 may be provided in the casing 20 which engages with a cam slot 331 provided on the body portion 1108, as shown in FIG. 46.

The spring 1104 is located at the end of the body portion 1108 and is arranged to bias the body portion 1108 up the channel 1110 towards the distal end of the casing 20. The spring 1104 can be of any suitable configuration, for example, the spring 1104 may be an arcuate or loop shape such as that shown in FIG. 11. The cam path 1106 is a moulded projection formed on the body portion 1108. The cam path 1106 comprises a first cam surface 1112, a notch 1114 and a second cam surface 1116 to form a "V" shaped moulding.

The latch 324 is formed of an arm 1118 extending from the bottom of the drive handle 22. The arm 1118 has a pin 1120 located at its end which is suitable for traversing the cam path 1106.

In use, the latch 324 enters the casing 20 via an opening 1102. The pin 1120 engages the latch moulding 326 such that the body portion 1108 is pulled down channel 1110 and the spring 1104 thereby being extended. As shown in FIGS. 26b-26c, the pin 1120 runs up the side of the first cam surface 1112 until it reaches the top of the "V". At this point, the drive handle 22 cannot be compressed any further, and the spring 1104 pulls the body portion 1108 back up the channel 1110 such that the pin 1110 slots into the notch 1114, thus retaining the drive handle 22 in the compressed position and the jaws 14 in the closed position, as shown in FIG. 26d.

Therefore, to latch the drive handle 22, all the user has to do is to actuate the drive handle into the fully compressed position, wait for the pin 1110 to click into the notch 114 and then release the drive handle 22. In this latched position, the user's hand is free for operating other functions of the instrument 1, such as operating the cutting mechanism using the trigger 24, rotating the jaws 14 using the rotation wheel 28 or operating the electrodes in the jaws 14 using the switch 6.

To release the latch 324 from the casing 20 and open the jaws 14, the user must squeeze drive handle 22 towards the casing 20 once more. This releases the pin 1120 from the notch 1114, as shown by FIG. 26*e*. As the pin 1120 exits the notch 1114, the force of the extended spring 1104 pulls the body portion 1108 back up the channel 1110, such that the pin 1120 runs down the side of the second cam surface 1116, as shown by FIGS. 26*e*-26*f*. As the pin 1120 reaches the bottom of the second cam surface 1116, it pushes the body portion 1108 further up the channel 1110 so that the pin 1120 can pass back out of the opening 1102. The body portion 1108 will then return back to its original position within the channel 1110.

Therefore, to release the drive handle 22, all the user has to do is squeeze the drive handle 22 towards the proximal end of the casing 20 and then allow the drive handle 22 to return to its original open position.

Additionally, the latch moulding 324 may include an override button 4600 integrally formed on the body portion 1108 as shown in FIG. 46, wherein the override button 4600 is engaged so as to alter the position of the cam path 1106 such that the pin 1120 automatically disengages with the notch 1114 and releases the drive handle 22. Consequently, if the latch mechanism was to hail for any reason, the user would be able to release the drive handle 22 to open the jaws 14.

The body portion 1108 may also be provided with an integrated lock-out bar 4602 to allow the user to disengage the latch mechanism altogether, wherein the lock-out bar 4602 is moveable between a first and second position to manually slide the body portion 1108 within the channel 1110. When the lock-out bar 4602 is in the first position, the body portion 1108 is in its normal position such that the latch mechanism operates as described above. The user may then move the lock-out bar 4602 to its second position, whereby the body portion 1108 is moved up the channel 1110 such that the pin 1120 can only traverse along the second cam surface 1116 and is thus prevented from engaging with the notch 1114.

It will be appreciated that such a latch mechanism may also be suitable for many end effector assemblies. For example, such a latch may be provided on the trigger 24 for the cutting mechanism so as to retain the cutting blade 340 in the actuated position.

On release of the latch 324, the drive handle 22 can be moved back to its original position. In doing this, the collar 304 releases the load exerted on the proximal flange 800 and pushes against the distal flange 802, thus pulling the collar moulding 310 back to its original axial position. Consequently, the spring 312, the inner moulding 314 and the drive shaft 316 are also pulled back axially, which in turn moves the jaws 14 back to the open configuration.

4. CUTTING MECHANISM ASSEMBLY AND OPERATION

Various further features and aspects relating to the structure and operation of the cutting mechanism will now be described. As described above, the proximal handle portion 10 of the electrosurgical instrument 1 includes a second mechanism for actuating a further aspect of a distal end effector assembly 14. For example, the end effector assembly 14 may be a set of opposed jaws 14 and a blade 340, wherein the distal end of the blade 340 is arranged to slide between the jaws 14 in order to cut tissue clamped between said jaws 14. The mechanism used to trigger movement of the blade 340, which is disposed within a central track 341 of the drive shaft 316, is the so called cutting mechanism. The cutting mechanism comprises a drive arm 2000, a blade drive moulding 346, a blade collar moulding 348, a blade moulding 352 and an extension spring 350, all of which are coupled together to form a three pivot slider-crank mechanism, as shown in FIGS. 20*a*-20*b* and FIGS. 31 and 32.

The drive arm 2000 is formed of a trigger 24 and the trigger moulding 344, wherein the trigger 24 is a finger gripping member for actuating the cutting mechanism and the trigger moulding 344 is a collar having a. "C" shaped side profile and an aperture 364 through which the drive shaft 316 is threaded. The point which the trigger 24 and trigger moulding 344 meet provides a pivot point A about which the drive arm 2000 is rotated. This first pivot point A is anchored to the casing 20, for example, by means of outward facing pins 358 that connect with corresponding mouldings 356 integral to the clamshell mouldings 300, 302.

The distal end of the drive arm 2000, that is, the end of the trigger moulding 344 is pivotally connected to the blade drive moulding 346 to form a second pivot point B. The blade drive moulding 346 is an "H" shaped frame having two parallel arms and a strut therebetween. As such, the parallel arms of the blade drive moulding 346 are pivotally connected at one end to the trigger moulding 344, for example, by means of outward facing pins 366 and mating connectors 368. At the opposite end, the parallel arms of the blade drive moulding 346 are also pivotally connected to the blade collar moulding 348 to form a third pivot point C, for example, by means of outward facing pins 372 and mating connectors 370.

As shown in FIGS. 21 to 23, the blade collar moulding 348 is a cylindrical or barrel shaped component having a chamber 2104 in which the blade moulding 352 sits, wherein the blade moulding 352 is a cylindrical or barrel shaped component having a body 362 that fits inside the chamber 2104 of the blade collar moulding 348. The blade moulding 352 further comprises a flange 360 having a diameter larger than that of the chamber 2104 such that the flange 360 abuts the distal lip 2200 of the blade collar moulding 348, as shown in FIG. 22. Consequently, the flange 360 ensures that the correct end of the blade moulding 352 is interested to the blade collar moulding 348.

The body 362 is provided with a small groove 2202 around its circumference so as to provide a shoulder with which the distal lip 2200 interlocks such that the blade moulding 352 and blade collar moulding 348 are coupled via a snap-fit connection. The distal lip 2200 mates with the groove 2202 so as to retain the blade moulding 352 within the blade collar moulding 348 whilst allowing the blade moulding 352 to freely rotate within the chamber 2104. As such, the blade moulding 352 and blade collar moulding 348 are free to rotate concentrically.

Once the blade collar moulding 348 and blade moulding 352 have been assembled together, the blade 340 can be connected as illustrated by FIGS. 24*a*-24*c*. In this respect, the blade moulding 352 comprises a "T" shaped aperture 2300 which extends throughout its length, shaped as such so as to receive both the blade 340 and the drive shaft 316, as shown by FIG. 23.

The proximal end of the blade 340 comprises a tab feature 2102 which extends beyond the general profile of rest of the blade 340, that is, it does not lie in the same axial plane. As shown in FIG. 24*c*, the body 362 further comprises a recess 2100 in which the tab 2100 is retained. To enable assembly, the proximal end of the blade 340 is cut away at a first point opposite the tab 2102 in order to provide a bevelled edge 2400, and is cut away a second point adjacent to the tab 2102 to provide a recessed portion 2402. As such, the proximal end of the blade 340 has an "L" shaped profile.

To assemble the blade 340 within the blade moulding 352 and blade collar moulding 348 assembly, the blade 340 is presented to the "T" shaped aperture 2300 at an angle to the longitudinal axis of the instrument 1 so that the tab 2102 and bevelled edge 2400 can be inserted to the internal cavity 2404 of the blade moulding 352, as shown in FIGS. 24a-24b. The blade 340 is then pulled down in line with the longitudinal axis so as to push the tab 2102 into the recess 2100, as shown by FIG. 24c. As such, the tab 2102 is effectively hooked on to the shoulder 2406 of the blade moulding 352, thereby retaining the proximal end of the blade 340 within the internal cavity 2404.

The drive shaft 316 may then be threaded through the "T" shaped aperture 2300, the blade 340 being received in the central track 342, as illustrated by FIGS. 22 and 23. As such, longitudinal movement of the blade collar moulding 348 and blade moulding 352 assembly along the drive shaft 316 drives the blade 340 along the track 342.

To complete the blade trigger assembly, an extension spring 350 extends between the blade collar moulding 348 and drive arm 2000, for example, by means of hooks 2002, 2004.

In use, the user pulls the trigger 24 back towards the easing 20, as shown by FIGS. 25b-25c, so as to pivot the drive arm 2000 around the first pivot point A. In doing this, the second pivot point B is pushed forwards in the distal direction which cause the drive moulding 346 to push the blade collar moulding 348 and blade moulding 352 assembly along the drive shaft. The load exerted on the trigger 24 is therefore transferred to the blade collar moulding 348 and blade moulding 352 via the trigger moulding 344 and drive moulding 346. As the proximal end of the blade 340 is retained inside the blade moulding 352 as described above, the blade 340 slides along the central track 342 with the blade collar moulding 348 and blade moulding 352 assembly. As the blade moulding 352 is rotationally isolated within blade collar moulding 348, the draft shaft 316 can also be rotated without interfering with the operation of the cutting mechanism.

Figure 27:
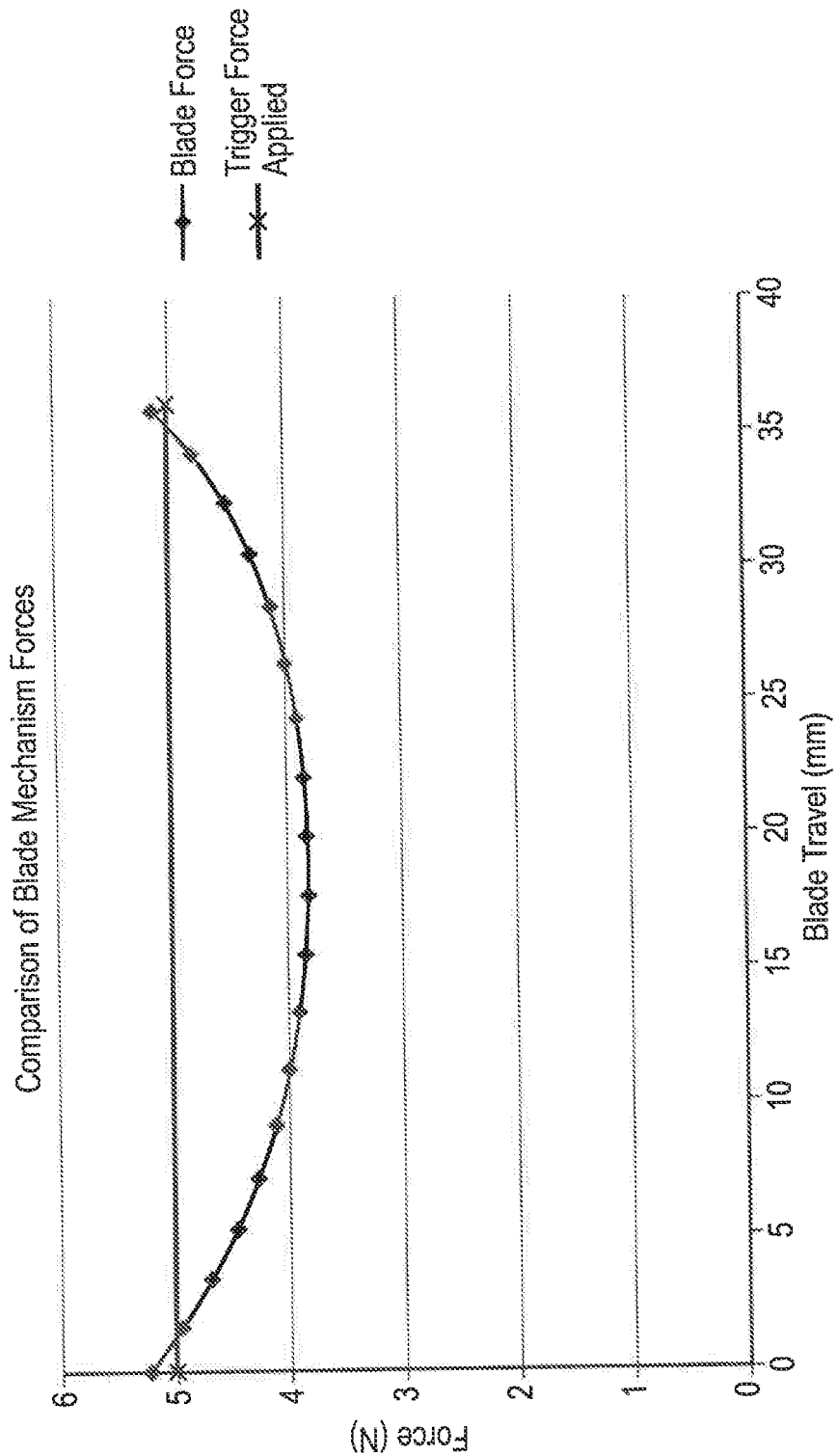
FIG. 27 is a graph illustrating the cutting mechanism of the electrosurgical instrument of FIG. 3.
Figure 28A:
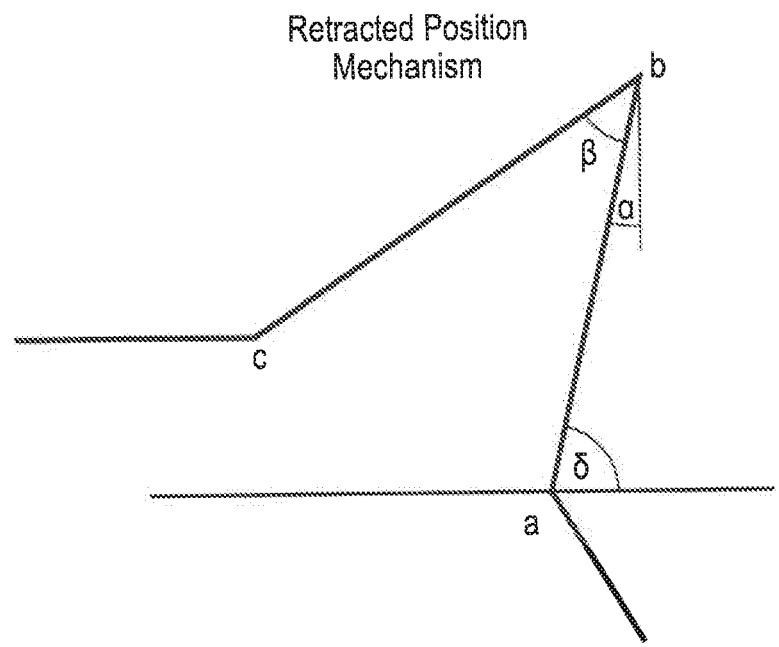
FIGS. 28a-28b are line drawings illustrating the cutting mechanism of the electrosurgical instrument of FIG. 3.
Figure 28B:
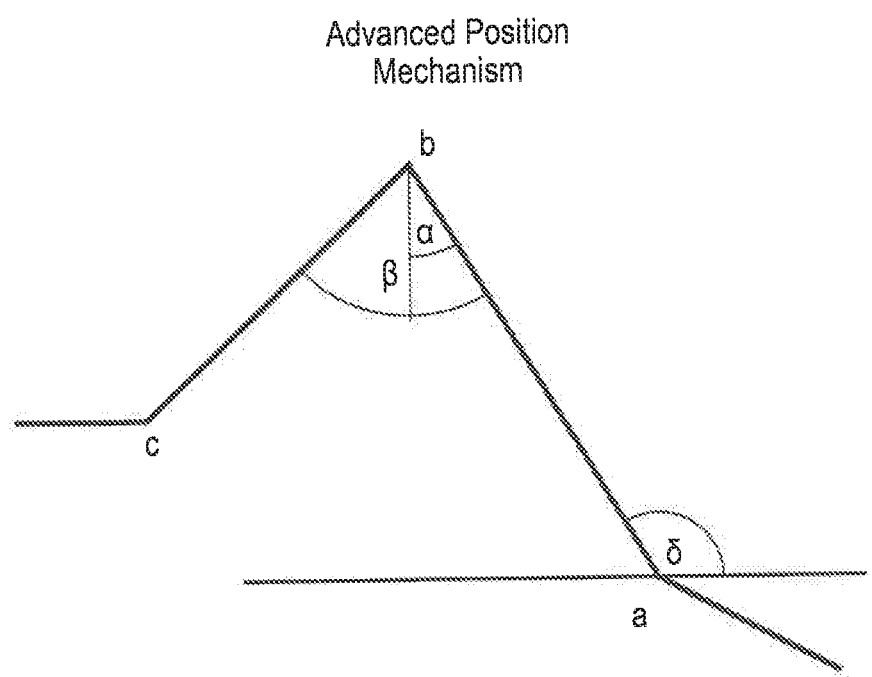
Figure 31:
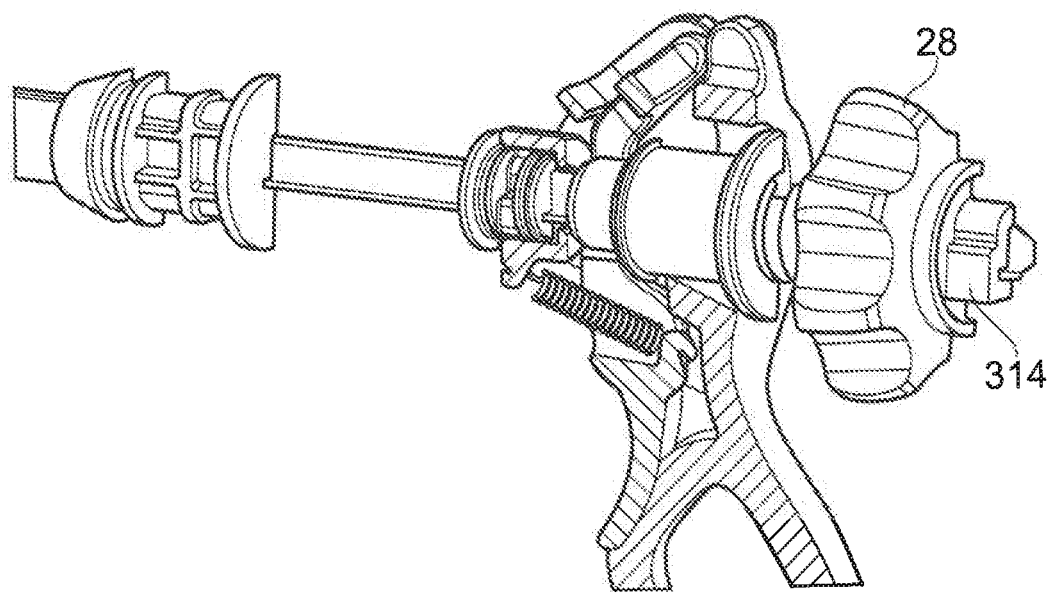
FIG. 31 is a partially section view of the cutting mechanism and clamping mechanism of the electrosurgical instrument of FIG. 3.
Figure 32:
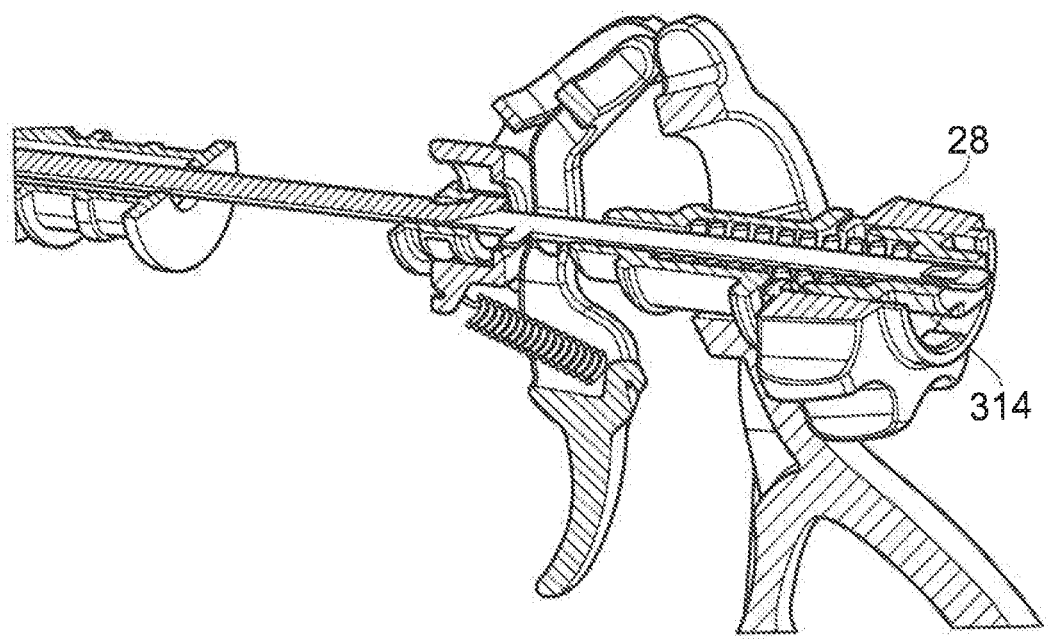
FIG. 32 is a partially section view of the cutting mechanism and clamping mechanism of the electrosurgical instrument of FIG. 3.
Figure 34:
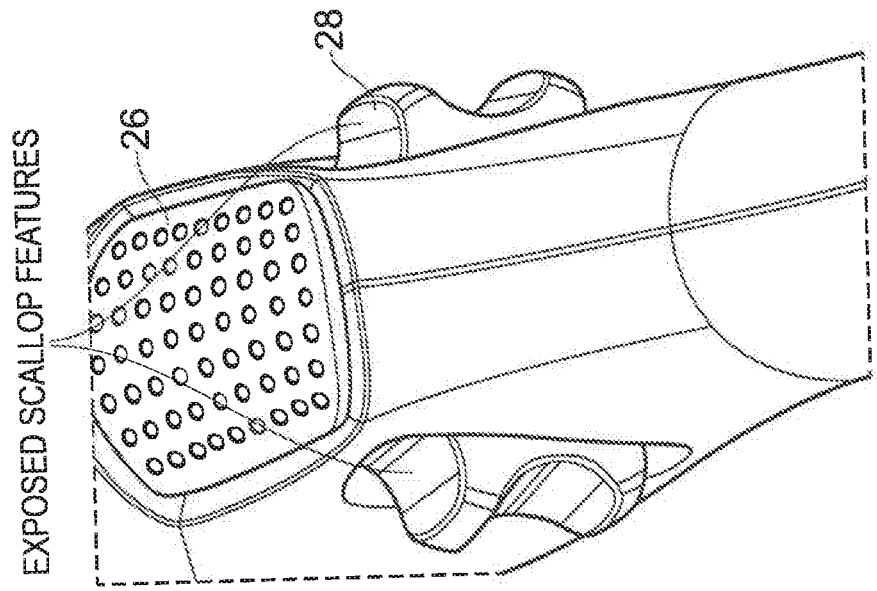
FIG. 34 shows the blade e control wheel part of the electrosurgical instrument of FIG. 3.

The functionality of the mechanism is optimised so as to provide good mechanical advantage at the beginning of the blade 340 travel, when the user's finger is extended and not as strong, and also at the end of the blade 340 travel, where there are more forces working against the blade 340 travel such as the force of the spring 350, friction within the track 342 and the force required to penetrate thick tissue. As can be seen from FIG. 27, a constant force is applied to the trigger 24 by the user. The mechanism converts this trigger force into a high initial blade 340 force, which decreases as the blade 340 is driven along the track 342, and increases again as the blade 340 reaches the jaws 14. Therefore, as the pivot point B moves from its retracted position to its protracted position as shown by FIGS. 28a-28b, such than β>90°, the speed at which the blade collar 348 and blade moulding 352 are driven along the drive shaft 316 accelerates, thus increasing the force of the blade 340. As such, the mechanism is able to drive the blade 340 with enough force to effectively cut the tissue clamped between the jaws 14 without the user needing to exert any additional force on the trigger 24.

Additionally, the cutting mechanism may be required to push the blade 340 around a curved set of jaws 14, adding to the frictional forces working against the blade 340 travel. The frictional force is a product of the frictional coefficient of the blade 340 within the track 342, and the force due to bending that the blade 340 exerts on the walls of the track 342.

To reduce this frictional force, the lateral flexibility of the blade's distal end may be graduated. Such graduated flexibility may be achieved, for example, by preferentially weakening the blade 340 such that it is able to bend along the track 342 whilst remaining rigid in the direction of the cutting force. Preferential weakening may be provided, for example, by the provision of one or more apertures or slots 354 in the distal end, as shown in FIG. 47a. Such apertures may be of constant or varying size of shape, depending on the degree of flexibility required. For example, in FIG. 47b, two contiguous apertures 4702, 4704 having different sizes are provided, wherein the larger aperture 4702 provides a greater degree of flexibility than the smaller aperture 4704. As another example, in FIG. 47c, three apertures 4706, 4708, 4710 of varying size and shape are provided, the largest aperture 4706 being the most distal so as to provide more flexibility in this region. Preferential weakening may also be achieved by graduating the thickness of the blade 340 such that the distal end of the blade 340 is bevelled 4700, as shown in FIG. 47d.

Alternatively, patterned laser cuts 4702 or chemical etches in the distal end may be used to control the bending stiffness over a length of the blade 340, as shown in FIG. 47e, whereby the spacing between such cuts may be constant or gradually increase from the distal to proximal end.

Preferably, the blade 340 is divided into at least three regions of varying flexibility. For example, a distal region, an intermediate region and a proximal region, wherein the distal region has a greater lateral flexibility than the intermediate region, and the intermediate region has greater flexibility than the proximal region. For example, the distal region may be formed of a bevelled end 4700 to give the greatest degree of flexibility, the intermediate region formed of an aperture 354 to provide a relatively lower amount of flexibility, and the proximal region formed of a solid bar to give even less flexibility, as illustrated by FIG. 47a. In a further example shown by FIG. 47b, the distal region includes a large aperture 4702 to give the greatest degree of flexibility, the intermediate region includes a smaller aperture 4704 to provide decreased flexibility and the proximal region is once again a solid bar having the lowest degree of flexibility. As such, the distal region, intermediate region and proximal region may be achieved using any suitable combination of the preferential weakening described above.

A further way of reducing the frictional force due to the curved track is to add a low friction coating to at least one side of the distal end of the blade 340. For example, the blade may be coated, for example using physical vapour deposition (PVD) or chemical vapour deposition (CVD) processes, with a low friction or non-stick material, such as a PTFE composite or other low friction polymer composite.

5. DRAINAGE APERTURES

Various further features and aspects relating to the structure of the drive shaft 316 will now be described. As described above, the drive shaft 316 is an elongate bar having a "T" shaped cross-section, as illustrated by FIG. 10a. The drive shaft 316 comprises a slot or track 342 along its length suitable for housing a further elongate member, such as the cutting blade 340 used in the cutting mechanism described above. In use, the cutting blade 340 is caused to slide along the length of the drive shaft 316 so as to drive the distal end of the cutting blade 340 between the jaws 14 in order to cut tissue clamped therebetween.

Over time, blood and tissue can start to build up within the distal end of the instrument 1, particularly down the length of the outer shaft 12 and drive shaft 316. This build-up of blood and tissue can cause the blade 340 to stick within the drive shaft 316, thus reducing the functionality of the instrument 1, in particular, that of the cutting mechanism. To combat this, portions of the distal end of the drive shaft 318 are cut out in order to reduce the area of contact between the drive shaft 316 and the blade 340 and thereby reduce the surface area to which blood and tissue can stick.

These cut out portions may be apertures such as the elongate windows 1000, 1002 shown in FIGS. 10b-10c, such that the distal end of the drive shaft 316 comprises a base support with bifurcated side walls. The cut out portions may also extend to the base of the drive shaft 316 such that the distal end comprises bifurcated side walls and an open bottom. In order to maximise the amount of drainage afforded by these apertures 1000, 1002, the apertures are preferably more than 50% of the depth of the drive shaft 316.

As such, these apertures 1000, 1002 provide drainage passages between the central track 342, and the exterior of the drive shaft 316.

6. ROTATION WHEEL AND SWITCH

Various further features and aspects relating to the operation of the thumbwheel (also referred to herein as a rotation wheel) 28 will now be described. The thumbwheel 28 is provided to allow the user to rotate the outer shaft 12 on which is mounted the end effector assembly 14. However, in order to reduce space, and hence produce a more compact instrument, the inner volume 1300 of the thumbwheel 28 is also utilised to provide movement space for the inner moulding 314, that forms part of the clamping mechanism described previously. With such an arrangement, a more compact mechanism can be obtained.

In more detail, the rotation wheel 28 (also referred to herein as a thumbwheel), comprises a plastic cog-like wheel, having a plurality of scallop portions 336 located around its external diameter. As such, the thumbwheel 28 takes the appearance of a cog, having the scalloped cut out portions arranged to receive a user's thumb, in an ergonomic fashion. In this respect, as shown in more detail in FIGS. 13a, 13b, and in particular in FIG. 14a, the scallop portions are angled to the plane of rotation of the thumbwheel when in use, such that generally the thumbwheel or rotation wheel 28 is slightly frusto-conical in shape, being wider at a distal end from the user than it is at the proximal end towards the user. The scallop portions 336 each extend from the distal edge of the thumbwheel to the proximal edge, and are curved or saddle like in shape to receive a user's thumb, when in use. As shown in detail in FIG. 14a, the angling of the scallop portions 336 to give the frusta-conical shape of the rotation wheel 28 generally matches the angle of the body of the instrument. In FIG. 14a the dot-dash lines illustrate the angling of the scalloping 336 around the edge of the wheel 28, which can be seen to be tangential to the angle of the outer walls of the instrument at the point around the wheel, and in particular of the portion of the outer walls of the instrument immediately in front of the wheel, in a distal direction. Such an arrangement where the angled scalloping of the outer rim of the rotation wheel matches the angling of the wall of the instrument around the wheel provides a comfortable and ergonomic design, which is easy to operate by the surgeon.

In terms of the number of scallop portions 336 around the outer diameter of the wheel 28, as shown in one embodiment eight scallop portions are evenly distributed around the outer diameter of the wheel. In other embodiments, fewer, or larger number of scallop portions may be used, for example as few as six or seven, or as many as nine or ten. If a larger wheel 28 was to be employed, then a greater number of scallop portions 336 may be included, and conversely if a smaller wheel is employed then the number of portions may be fewer in number. In this respect, the actual size of each scallop portion 336 should typically remain the same, as the scallop portions have been ergonomically chosen so as to be able to receive a user's thumb comfortably.

Regarding the positioning of the thumbwheel 28 within the instrument, as shown in FIG. 2, the rotation or thumbwheel 28 is positioned vertically oriented beneath the switch 26, and spaced from the thumbwheel in a direction orthogonal to a longitudinal axis defined for example by the longitudinal direction of drive shaft 316. In particular, the handswitch 26 lies directly on an axis orthogonal to such a longitudinal axis and which also passes through the thumbwheel 28. Moreover, as shown in FIGS. 14a and 14b, the switch 26 is relatively large in size, and extends from one side of the upper surface of the instrument to the other, above the thumbwheel. The switch 26 is curved in nature, generally to match the curved upper surface of the outer wall of the instrument, and has bumps, grooves, or other raised protrusions on the outer surface thereof, to aid with the user being able to grip the switch in order to be able to press it, with his or her thumb. The surface area of the switch 26 is relatively large, being in excess of 3 cm$^2$ or even 5 cm$^2$. This provides a large surface area, to allow for ergonomic activation thereof by the user. The vertical orientation of the switch 26 directly above the thumbwheel 28 also allows for ergonomic activation. As explained elsewhere, the switch 26 in use operates to cause an RF coagulation signal to be fed to the end effector, for coagulation of any tissue located therein.

Figure 35B:
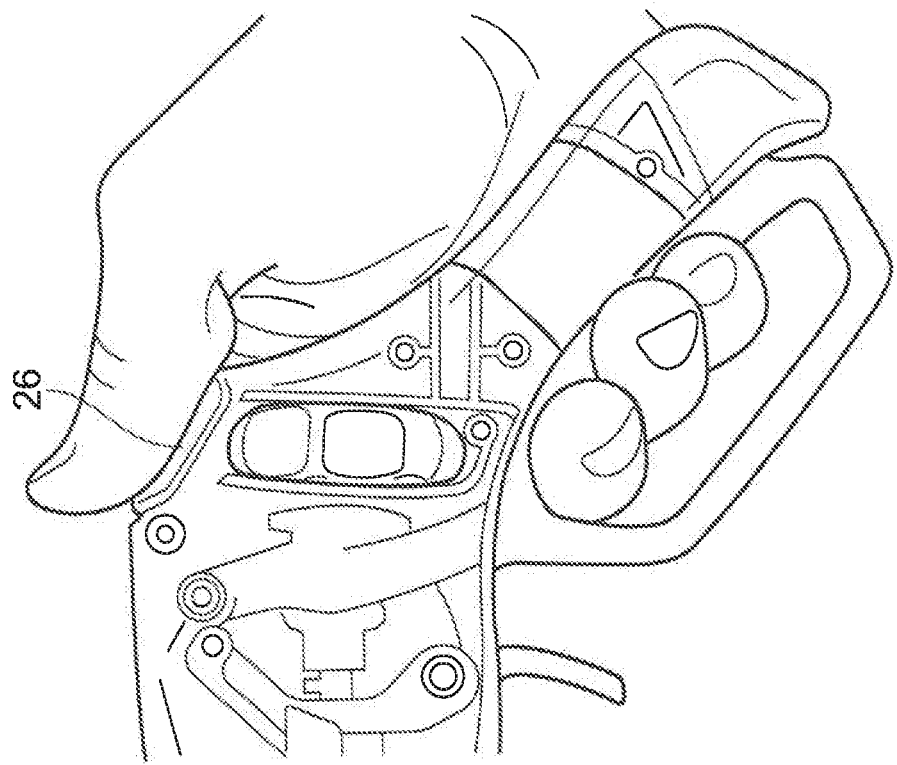
FIGS. 35a-35b illustrate the handle of the electrosurgical instrument of FIG. 3, held by users with different size hands.
Figure 35A:
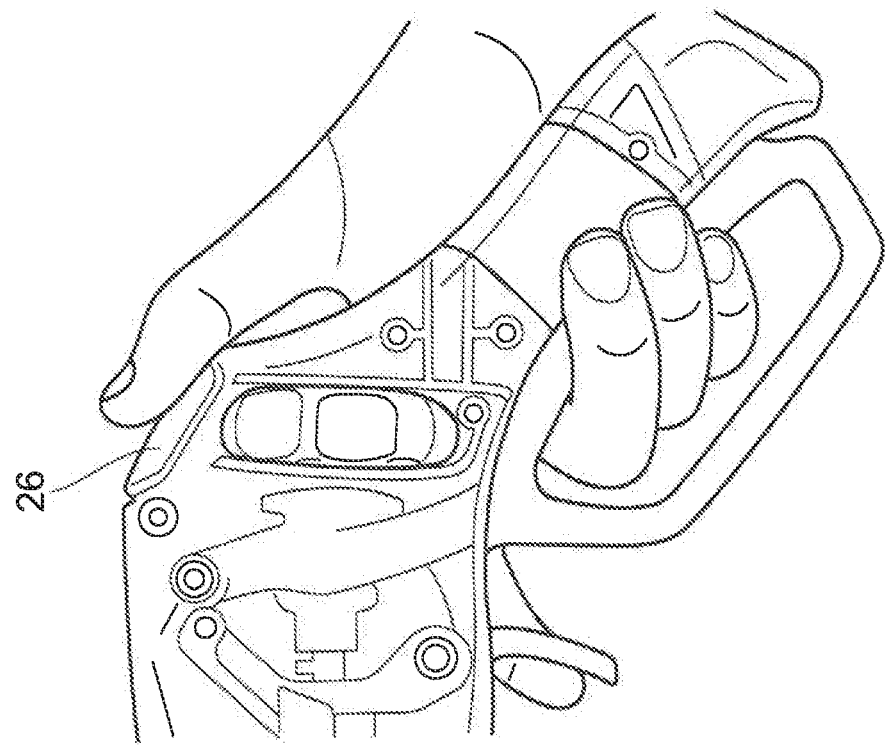

Concerning the ergonomics of the switch and thumbwheel, FIGS. 35a and 35b are two respective photographs of different users with different size hands. As demonstrated, the switch 26, being of a relatively large surface area is easy to operate by users with different hand sizes, at the same time as operating clamping handle 22 (and blade trigger 24, if desired).

Returning to FIG. 12, as described previously the thumbwheel 28 has an internal cavity 1300 within which is received in use the inner moulding 314. As described previously, the inner moulding 314 comprises an inner moulding chamber 610 and has a T-shaped cut through portion 1208 therein, into which the drive shaft 316 is received therethrough, and fastened therein, as described previously. The inner moulding 314 snap fits into the interior cavity of the wheel 28, and flanges 1206, as shown in FIG. 12 and FIGS. 29a and 29b are provided around the outer edge of the cylindrical interior cavity 1300 of the thumbwheel 28, to hold the inner moulding 314 in place within the cavity, once it has been inserted therein. The interior cavity 1300 of the thumbwheel 28 is also provided with interlocking members 1200, which interact with corresponding interlocking members 1202 provided around the outer circumference of the inner cylindrical moulding 314. The respective interlocking members 1200 and 1202 comprise respective raised step portions that fit together side by side circumferentially around the inner surface of the cavity 1300 when the thumbwheel 28 and the inner cylindrical moulding 314 are in the correct rotational alignment with respect to each other. The respective interlocking members 1200 and 1202 are provided so that in use the inner cylindrical moulding 314 may slide from side to side within the interior cavity of the wheel 28, but may not rotate within the wheel 28. Instead, the interacting interlocking members 1202 and 1200 act so that the inner moulding 314 rotates with the rotation wheel 28, as it is rotated. In this way, any rotational torque applied by the user 28 to the rotation wheel 28 is transferred to the inner moulding 314, and then to the drive shaft 316, in order to rotate the driveshaft, carrying the end effector. FIGS. 29a and 29b show the inner moulding 314 inserted into the interior cavity of the thumbwheel 28, and illustrate how the inner moulding 314 may slide axially within the inner cavity 1300 of the wheel 28.

FIGS. 13a and 13b also show in more detail how the inner moulding 314 is able to move within the inner cavity 1300 of the wheel 28. As described above, the drive shaft 316 passes through the T-shaped aperture 1208 in the inner moulding 314, and is secured therein via snap fit protruding catch or latch members 602, provided on the end of the drive shaft. That is, latch or catch members 602 are in the form of sprung metal tabs that are able to pass through the T-shaped aperture 1208 within the inner moulding 314, and are then received in an inner moulding second channel part 606 forming a cavity which allows the spring tabs to spring apart, thus securing the drive shaft within the inner moulding. The inner moulding 314 is then pushed into the inner cavity of the thumbwheel 1208, and is held in place by the snap fit tabs 1206, as described above. The inner moulding may move axially within the inner cavity 1300 so as to abut against the inner surface of the distal wall of the wheel 28, as shown in FIG. 13a, or, at its opposite end of travel, to abut against the tabs 1206 at the distal edge of the wheel. Thus, the inner moulding 314 is provided with a degree of axial sliding movement within the cavity of the thumbwheel 28, which is required as part of the mechanism to control the force applied by the user to material contained within the jaws, as described above.

Figure 33:
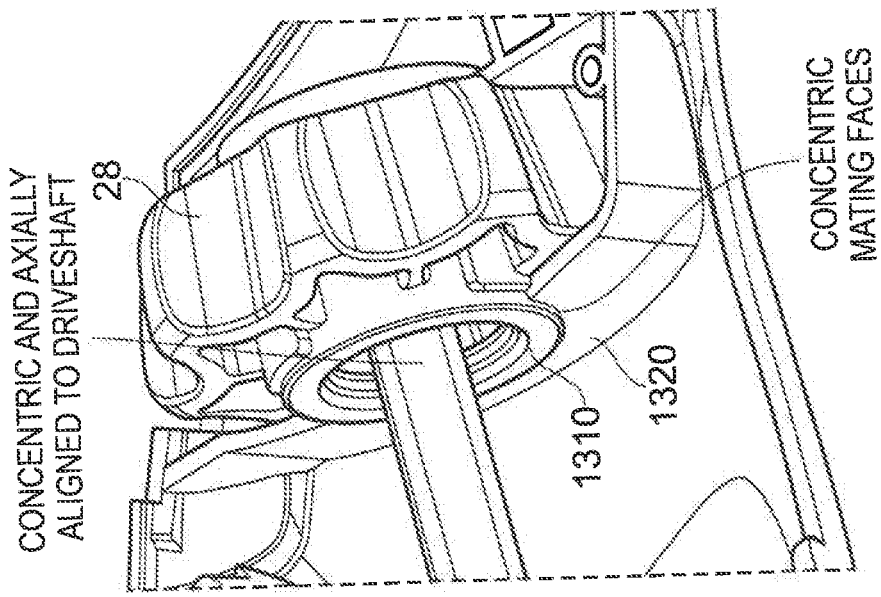
FIG. 33 shows the blade angle control wheel part and the electrode control switch of the electrosurgical instrument of FIG. 3.

The snap fit nature of the inner moulding 314 into the inner cavity of the thumbwheel 28 hugely improves the assembly of the device, and makes the device significantly easier, and hence cheaper to assemble. Likewise, in order to position the thumbwheel within the casing, as shown in FIG. 33, the outer distal wall 1310 of the thumbwheel 28 is concentric with and aligned to an internal supporting wall 1320, provided as a projection from the casing of the device. This also allows for easy and accurate assembly and positioning of the wheel 28 within the casing.

7. ROTATIONAL CONTROL OF DRIVE SHAFT

As explained above, shaft 12 having end effector 14 thereon is rotatable to allow the end effector to be moved into desired rotational positions for the cutting and coagulation of tissue. However, in order that the wiring connections to the end effector are not placed under excess strain from the shaft being rotated in one direction too far such that the wiring becomes wound up, twisted, or placed under excessive strain, a mechanism to control the rotation of the shaft 12 is required, in particular to limit the amount of rotation, and thereby prevent excess strain on the wiring. In addition, providing positive control of the rotation of the shaft 12 improves the ergonomic experience of the instrument when in use, and enhances the user perception of quality.

In order to provide rotational control of the shaft in one embodiment an arrangement as shown in FIGS. 15a and 15b, and FIGS. 16a to 16d is employed. With reference to FIG. 15, here thumbwheel 28 having scallop portions 36 is provided on its proximal surface (i.e. rearward face, facing the user) with a ring 1506 that projects slightly from the proximal surface arranged concentric with the axis of the wheel 28. The ring 1506 rests in use on guide stop features 1502 and 1504, being projections from the inner surface of the outer casing, that project up to make contact with the outer circumference of the ring 1506. Stop feature 1502 is smaller than stop feature 1504 due to their positioning on the casing with respect to the axis of the ring, but both stop features 1502 and 1504 have angled upper guide faces 1510 and 1512 (see FIG. 15a) respectively, that contact with the outer circumferential surface of ring 1506 forming part of the thumbwheel, and help to support and guide the thumbwheel in its rotation.

In addition, to providing a guiding function, stop features 1502 and 1504 also act as stop members to prevent the rotation of the thumbwheel past the angular position of the stop features. In this respect, the ring 1506 is provided with a rectangular stop projection 1500 radially extending therefrom. As the thumbwheel 28 is rotated the stop projection 1500 abuts against respective stop faces 1514 and 1516 of the stop features 1502 and 1504. The stop faces are angled to be parallel to the rectangular stop projection 1500 when the stop position is angularly positioned so as to be abutted thereagainst.

The stop features 1502 and 1504 arranged as described above are positioned, and are of such a length so as to provide a known amount of rotation of the wheel 28 from stop feature 1500 to stop feature 1502. In the presently described arrangement shown in FIG. 15a and FIG. 15h the stop features 1502 and 1504 are positioned on the casing with a spacing therebetween so as to allow the thumbwheel to rotate 270° from stop to stop. The amount of rotation can be varied slightly by increasing or decreasing the distance between the stop features, with the stop features being adapted in length and angle of the guide and stop faces accordingly so as to still meet the wheel and the stop features substantially normally, respectively. For example, the stop features may be positioned and shaped to provide angular rotation of the wheel of between 250° and 300°.

The above describes the rotational control that is applied to the thumbwheel (and then to the shaft via the thumbwheel). FIGS. 16a to 16d show a further rotational control mechanism that is applied to the shaft at the opposite end of the shaft, using shaft moulding 320. Here, shaft moulding 320 is provided with rectangular stop member 1600 projecting therefrom. The inner surface of the outer casing is further provided with respective moulded stop features 1602, and 1604, shown in the form of stepped feature providing respective stop surfaces that present to the rectangular stop member 1600 respective parallel stop surfaces at respective angular positions of the shaft moulding 320. In the example shown, the moulded stop features are positioned on the casing and present respective stop surfaces to the stop member 1600 to permit a rotation of 270° of the shaft 12 carrying the end effector from stop to stop. In other embodiments, the moulded stop features 1602 and 1604 may be positioned to present stop surfaces to the stop member 1600 at other rotational angular positions of the moulding 320, to provide a greater or lesser amount of rotation, for example from 180° to 360°, or more preferably from 250° to 300°, or most preferably 270°.

The respective rotation control mechanisms provided in the thumbwheel 28 and the shaft moulding 320 may be provided independently from each other i.e. they need not both be provided in any particular embodiment, but only one or the other may be provided to provide for rotational control of the shaft. However, it is advantageous in terms of operation and the perception of quality of the device for both the rotation control mechanisms to be provided in the same device, and to be aligned such that they provide for stopping of rotation at the same respective points, in either rotational direction. Such an arrangement means that the rotation of the shaft is stopped independently at both ends of the handle portion 10, and it becomes very difficult for a user to force further undesirable rotation of the shaft past the allowed limits represented by the stops.

Figure 36A:
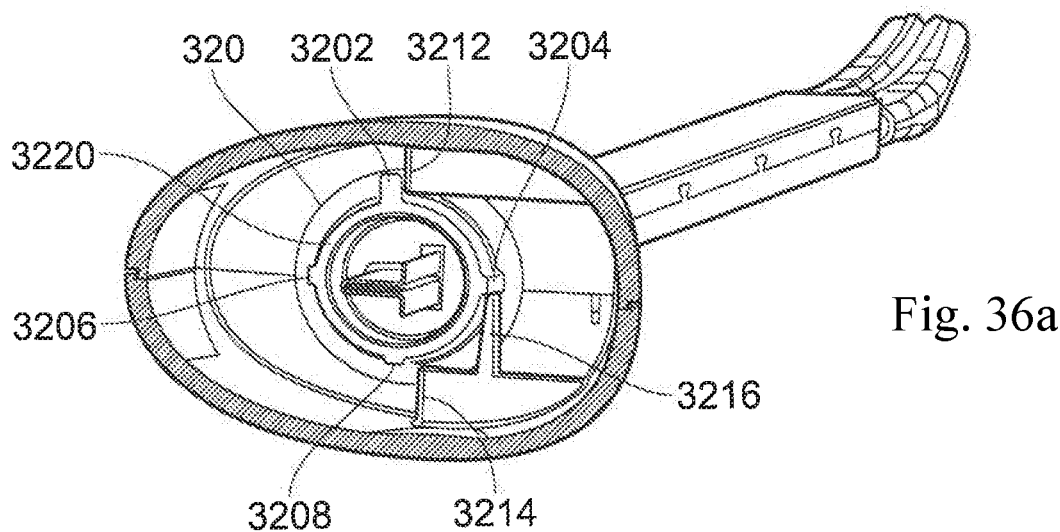
FIGS. 36a-c illustrate the rotational movement of the end effector of the electrosurgical instrument of FIG. 3.
Figure 36B:
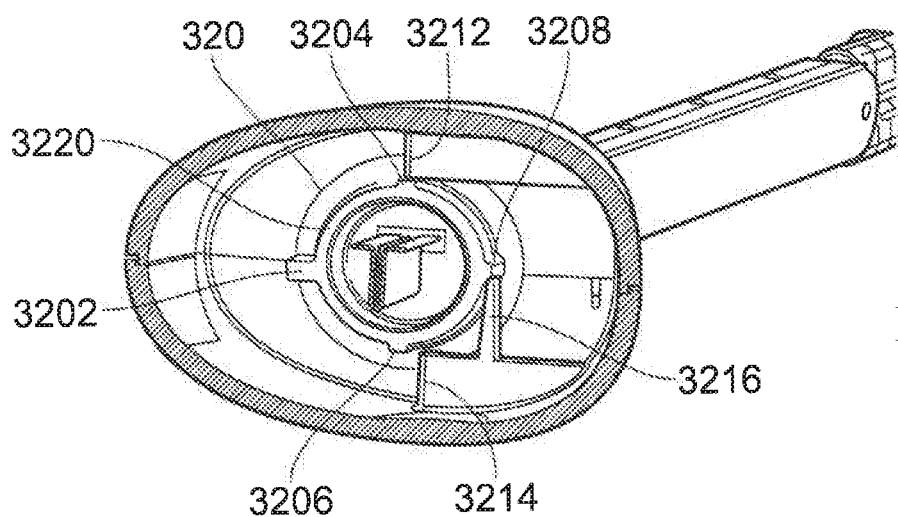
Figure 36C:
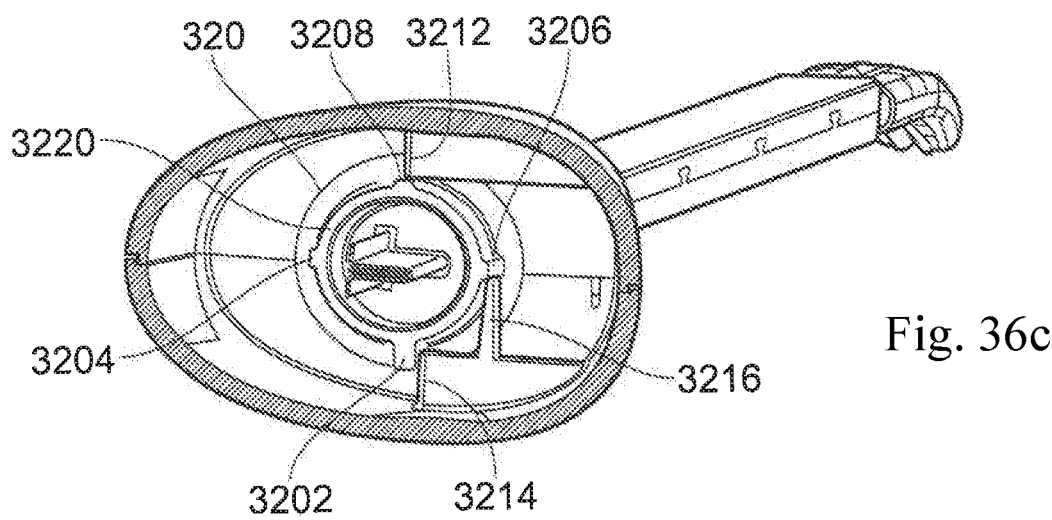
Figure 37:
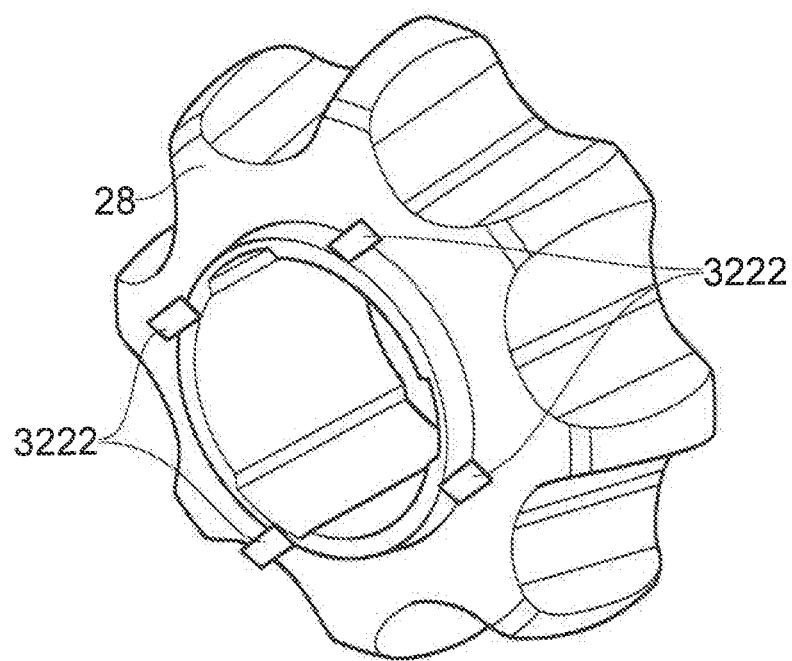
FIG. 37 illustrates the rotational movement of the blade angle control wheel of the electrosurgical instrument of FIG. 3.

An alternative rotational control mechanism is shown in FIGS. 36 and 37. FIG. 36 illustrates again the shaft moulding 320, but here the moulding is provided with ring 3220 on which is mounted a primary rectangular stop member 3202 projecting radially therefrom, and secondary position marker members 3204, 3206, and 3208, positioned around the ring substantially equiangularly, preferably at orthogonal positions. The secondary position marker members 3204, 3206, and 3208 constitute small raised projections that are not large enough to about against stop faces 3212 and 3214.

Stop faces 3212 and 3214 are provided as integral mouldings with the outer casing, and are positioned here so as to permit the shaft moulding 320 to be rotated by 180°. In this respect, the stop member 320 abuts against the stop faces 3212 and 3214 at the ends of the rotation range, to prevent further rotation of the shaft moulding. Hence, as shown in FIGS. 36a-36c, the shaft moulding 320 carrying the shaft 12 may rotate through 180°, to allow the end effector to be positioned rotationally as desired.

Also provided is a sprung projection 3216, comprising a plastic projection of substantially triangular cross-section that projects upwardly from the moulding forming stop face 3214, such that its tip contacts the outer circumferential surface of ring 3220. The secondary position markers in the form of the small raised projections press against the tip of the sprung projection as the shaft moulding 320 rotates, causing the tip of the sprung projection to move out of its rest position to allow the respective projection to move past the tip. The effect of this operation is to provide some user feedback in that the user must apply more force to rotate the mechanism past the rotational positions where the raised projections contact the tip of the sprung projection, because sufficient force must be provided to cause the tip of the sprung projection to deflect, to allow the projection to move past the tip. The result of this is that the user feels an increase of force required to rotate the shaft past the rotational positions of the raised projections, and hence intuitively the user is provided with an indication of the rotational position of the shaft, and hence the end effector. Such a haptic feedback mechanism thus allows for user friendly and easy operation of the device.

FIG. 37 illustrates the corresponding thumbwheel 28 for the mechanism of FIGS. 36a-36c. Here, the thumbwheel is also provided with respective small stops 3222, arranged orthogonally at 90° intervals around the thumbwheel. A similar mechanism to the sprung projection 3216 may be provided, projecting from the casing, to provide similar haptic feedback as in the case of the shaft moulding 320. In such an arrangement, haptic feedback as to the rotational position of the shaft is provided from both ends of the handle, and hence the user perception of the device is improved.

8. WIRING

Various further features and aspects relating to the wiring within the handle 2 will now be described. As described above, the switch button 26 is provided for activating and de-activating the RF signal for operating the electrodes in the end effector assembly 14 via some appropriate circuitry, for example, two ingress-protected switches on a small printed circuit board (PCB) 338. As shown in FIG. 17, the PCB 338 is connected to a connection cord 1700 for receiving the RF output from a generator (not shown) and electrical wiring 1702, 1704 for supplying the RF current to the electrodes in the jaws 14, for example, one wire for the active electrode and one for the return electrode.

In assembly, the wiring 1702, 1704 from the electrodes is fed down the outer shaft 12 alongside the drive shaft 316 and up to the shaft moulding 320, as illustrated by FIG. 17. As shown in FIG. 9b, the shaft moulding 320 is a cylindrical or barrel shaped component having an opening 912 at the distal end to receive the outer shaft 12. The outer shaft 12 is attached to the shaft moulding 320, for example, by snap-fit tabs 900 that cooperate with corresponding notches 902 within the shaft moulding 320. Consequently, if the shaft moulding 320 rotates, the outer shaft 12 rotates with it. The shaft moulding 320 further comprises a further aperture 914 at the proximal end, the aperture 914 having a "T" shape so as to receive the drive shaft 316, wherein the drive shaft 316 extends through the internal cavity 1802 of the shaft moulding 320 and down the length of the outer shaft 12. As such, the drive shaft 316 is able to slide within the shaft moulding 320 and outer shaft 12, but any rotational movement of the drive shaft 316 is transferred to the shaft moulding 320 and subsequently the outer shaft 12.

As shown in FIG. 18a, the electrode wires 1702, 1704 are fed out of the internal cavity 1802 through an opening 1800 in the wall of the shaft moulding 320 before being wrapped over and around the body 1804 of the shaft moulding 320. Wrapping the wires 1702, 1704 around the shaft moulding 320 in this way keeps the wires 1702, 1704 in a compact arrangement so as prevent the wires 1702, 1704 from getting in the way when assembling the rest of the instrument 1. Furthermore, wrapping the wires 1702, 1704 around the shaft moulding 320 means that as the shaft moulding 320 rotates with the drive shaft 316, the wires 1702, 1704 un-wind and re-wind with said rotation without pulling on the wires 1702, 1704 and causing them to short. Specifically, wrapping the wires 1702, 1704 in this particular way allows for up to 270° of rotation, as described with reference to FIGS. 15a-15h and 16a-16d.

The electrical wiring 1702, 1704 is then passed along the top of the casing 20. In this respect, one of the clamshell mouldings 300 is provided with two pockets 1900, 1902 located in series for housing the wire contacts 1904, 1906 that connect the active and return wires 1702, 1704 to the wiring 1908, 1910 of the ingress-protected switches 338. Consequently, all of the electrical wires 1702, 1704, 1908, 1910 are routed in and around the pockets 1900, 1902 so that only one contact 1904, 1906 is housed in each pocket 1900, 1902. The routing of the wires may be aided by guide portions 1912, 1914, 1916 which direct one set of the wires 1702, 1910 around the outside of the pockets 1900, 1902. Within each pocket the respective active wire 1702 is longitudinally aligned with wire 1908, and return wire 1704 is longitudinally aligned with wire 1910.

As a result, the two wire contacts 1904, 1906 are longitudinally separated such that only one contact can pass through each pocket 1900, 1902, thereby providing a physical barrier between each contact 1904, 1906 and any wiring. This prevents the risk of insulation damage to any of the wiring caused by the contacts 1904, 1906 themselves.

The wires 1702, 1704, 1908, 1708 all enter their respective pockets 1900, 1902 through small openings 1918, 1920, 1922, 1924 in the walls of the pockets. Preferably, the dimensions of the apertures 1918, 1920, 1922, 1924 are such that only one electrical wire can fit through. The opposite clamshell moulding 302 also comprise corresponding rib features (not shown) to retain the contacts 1904, 1906 within the pockets 1900, 1902, so as to form a substantially sealed housing. This is important for minimising the permeability of the pockets 1900, 19200 in order to protect the contacts 1904, 1906 from any fluid that may make its way down the outer shaft 12 and into the casing 20, thus causing the contacts 1904, 1906 to short circuit.

9. END-EFFECTOR ASSEMBLIES

Example end-effector assemblies that may be used with the apparatus will now be described. The examples to be described are given for completeness only, and it should be understood that other designs of end-effector may also be used with the instrument, provided they are able to be driven by drive shaft 316. That is, embodiments of the invention are not limited to the specific end-effectors described herein, and other designs of end-effector may also be used.

Figure 38:
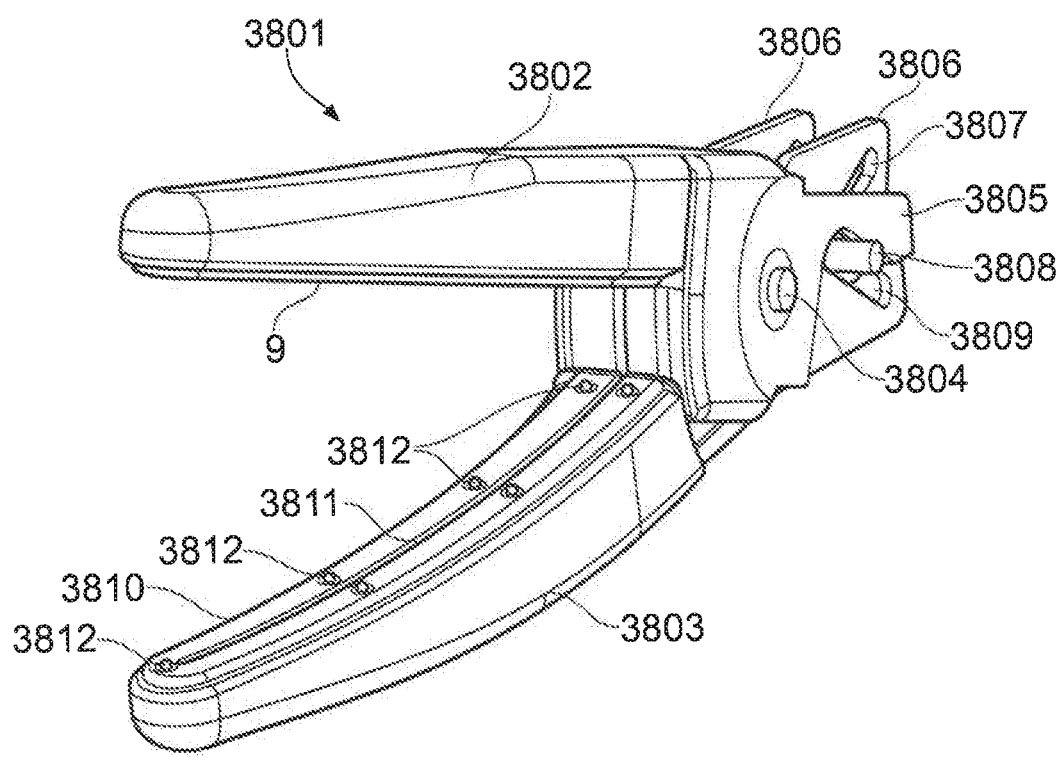
FIG. 38 is a schematic perspective view of an example end effector.
Figure 39:
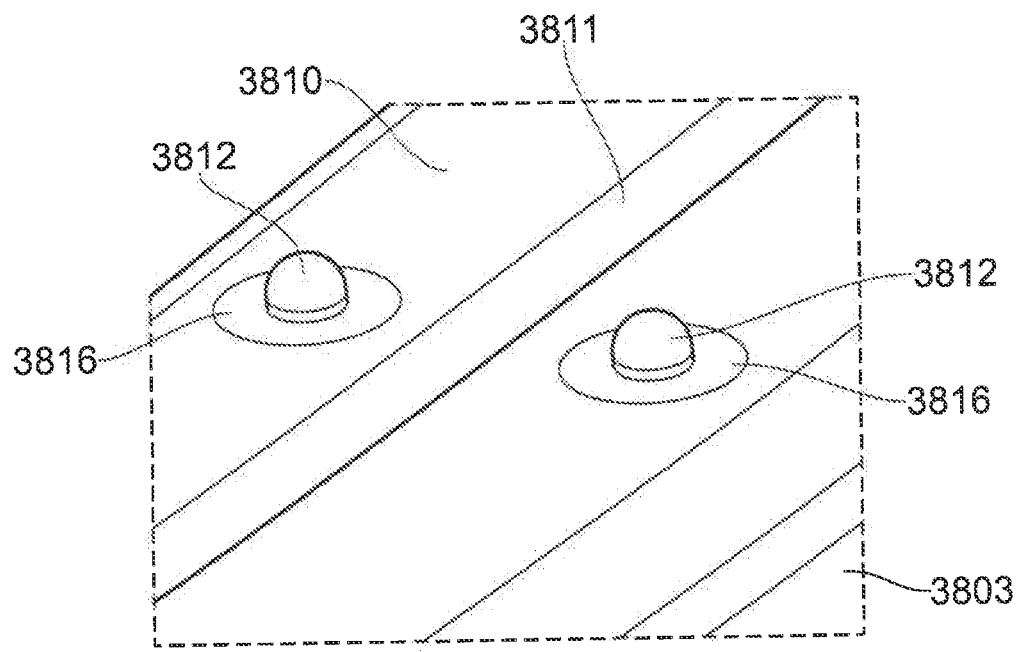
FIG. 39 is an enlarged perspective view of a part of the end effector of FIG. 38.

FIGS. 38 to 44 show example instruments where the electrically conductive stop members are disposed on one or both of the sealing electrodes. Referring to FIG. 38, an end effector shown generally at 3801 comprises an upper jaw 3802 pivotably connected to a lower jaw 3803 about a pivot 3804. Flanges 3805 are present at the proximal end of upper jaw 3802, while flanges 3806 are present at the proximal end of lower jaw 3803. The flanges 3805 & 3806 each have slots 3807 through which a drive pin 8 extends, such that proximal and distal movement of the drive pin 3808 (by means of a drive mechanism (not shown) causes the jaws 3802 & 3803 to pivot between open and closed positions.

A metallic shim 3809 is present on the inward face of upper jaw 3802, while a metallic shim 3810 is present on the inward face of lower jaw 3803. When the jaws 3802 & 3803 pivot into their closed position, the metallic shims 3809 & 3810 come into close proximity one with the other, in order to grasp tissue (not shown) therebetween.

The upper shim 3809 has a generally planar surface, with the exception of a longitudinal groove (not visible in FIG. 38) running the length thereof. The lower shim 3810 has a corresponding groove 3811, the grooves in the shims 3809 & 3810 accommodating the longitudinal movement of a cutting blade (not shown). The lower shim 3810 is also provided with a plurality of metallic stop members 3812, disposed along the length of the shim and situated on either side of the groove 3811. The stop members 3812 will now be described in more detail, with reference to FIGS. 39 & 40.

Each metallic stop member 3812 is constituted by the upper dome of a stop element 3813, which is enclosed in an insulating member 3814 such that it encapsulates the stop element isolating it from the remainder of the shim 3810. Each insulating member 3814 and stop element 3813 is positioned in a corresponding aperture 3815 present within the shim 3810, such that the upper portion of the insulating member forms an insulating ring 3816 around each stop member 3812.

Figure 40:
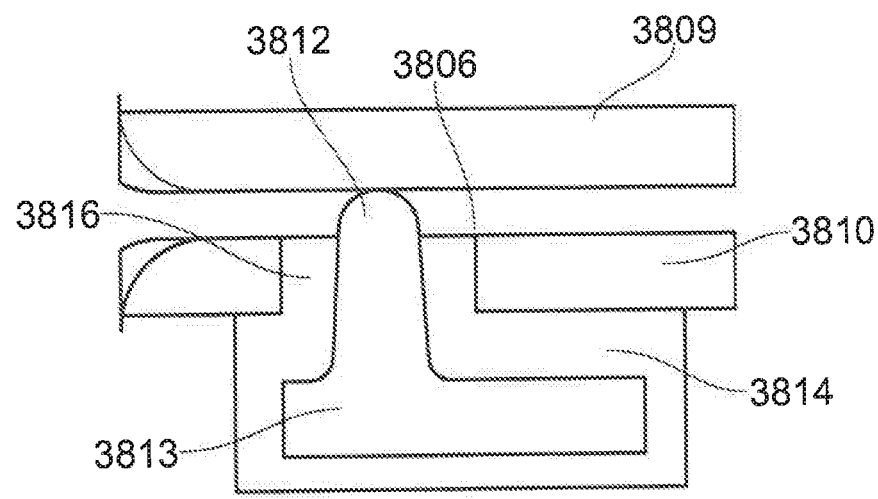
FIG. 40 is a schematic sectional view of a part of the end effector of FIG. 38.

When the jaws 3802 & 3803 are moved to their closed position (as shown in FIG. 40), the stop members 3812 contact the upper shim 3809 maintaining a separation between the upper and lower shims of between 20 μm and about 350 μm (0.00079 inches to about 0.014 inches). In use, a coagulating electrosurgical voltage is supplied between the shims 3809 & 3810, and the separation of the shims ensures effective sealing of tissue grasped between the jaw members 3802 & 3803. In the meantime, electrical shorting between the shims is prevented, as the stop members 3812 are electrically isolated such they do not carry the same electric potential as the remainder of the shim 3810. The metallic stop members 3812 are rigid, allowing for a consistent separation of the shim surfaces, while it is feasible that the electric potential of the stop elements 3813 can be monitored in order to detect when they contact the upper shim 3809 to give an indication of the closure of the jaws.

Figure 41:
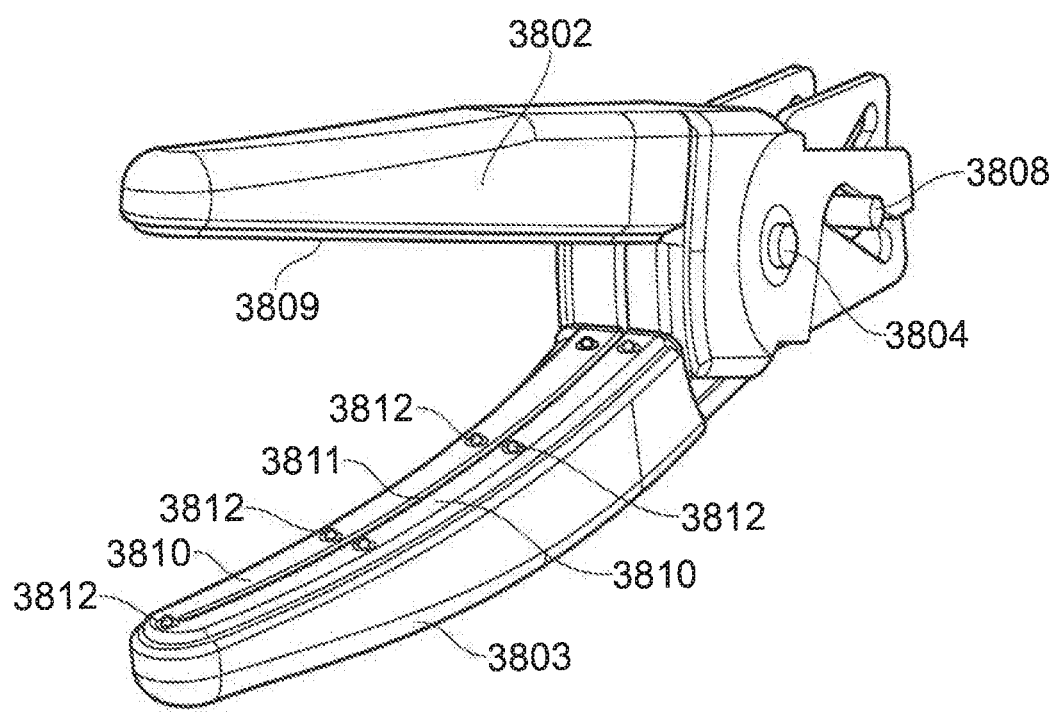
FIG. 41 is a schematic perspective view of an alternative end effector.
Figure 42:
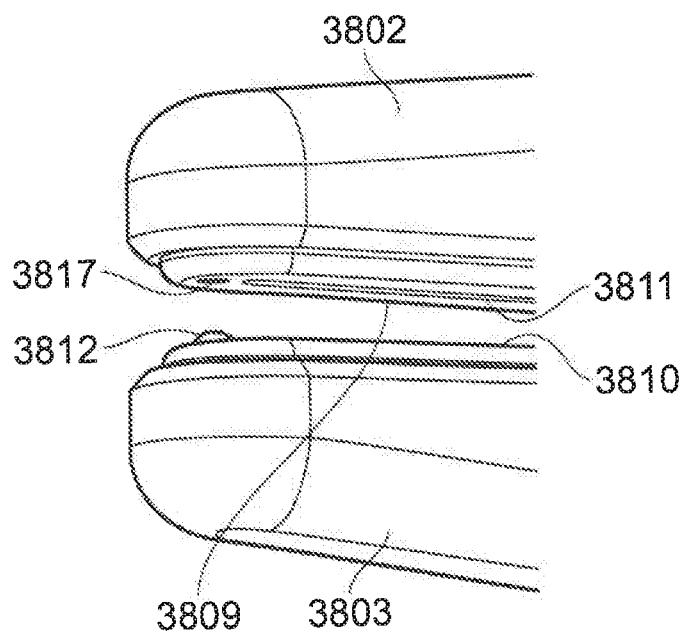
FIG. 42 is an enlarged perspective view of a part of the end effector of FIG. 41.
Figure 43:
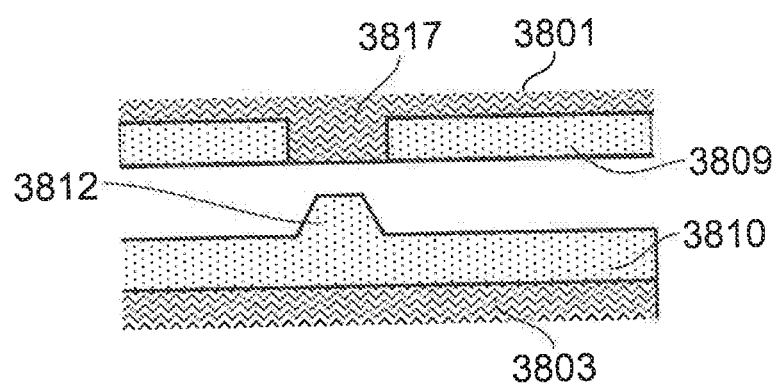
FIG. 43 is a schematic sectional view of a part of the end effector of FIG. 41.

FIGS. 41 to 43 show an alternative arrangement in which the metallic stop members 3812 are mounted directly on the lower shim 3810, without the provision of the insulating members surrounding the stop members. In this arrangement, insulating members 3817 are provided on the upper shim 3809, in corresponding relationship to each of the stop members. In this way, when the jaws 3802 & 3803 are closed, the insulating members 3817 ensure that there is no electrical shorting between the upper shim 3809 and the lower shim 3810. The metallic stop members 3812 ensure that the appropriate separation of the jaw members is maintained during the application of electrosurgical energy in order to seal tissue grasped between the jaws.

Figure 44:
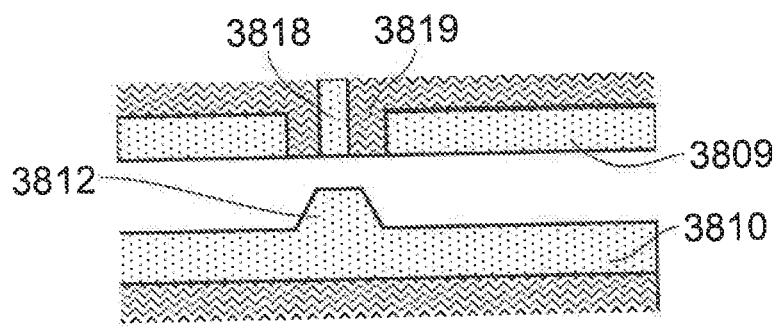
FIG. 44 is a schematic sectional view of a part of a further alternative end effector.

Finally, FIG. 44 shows a further alternative, in which the metallic stop members 3812 are once again mounted directly on the lower shim 3810. In this arrangement, a metallic anvil 3818 is located opposite each of the stop members, each metallic anvil 3818 being surrounded by an insulating member 3819 in order to isolate it from the remainder of the upper shim 3809. When the jaws are closed, metal-to-metal contact takes place between the stop members 3812 and the metallic anvils 3818, with the isolation of the anvils ensuring that electrical shorting between the shims 3809 & 3810 is once again avoided. Once again, the electric potential of each of the metallic anvils can be monitored in order to detect when they assume the potential of the lower shim, indicating closure of the jaws.

10. ELECTRO-SURGICAL SYSTEM

Figure 45:
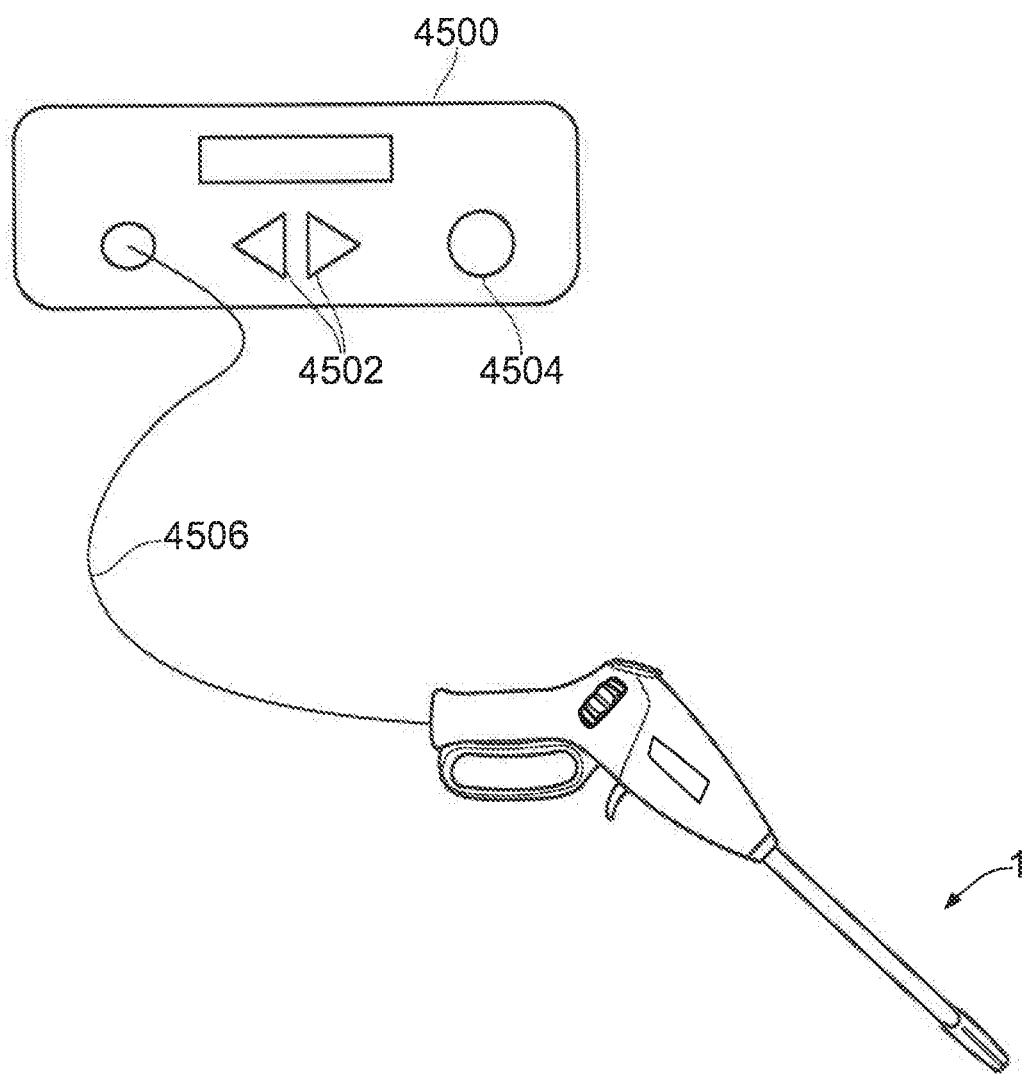
FIG. 45 is a representation of an electro-surgical system including a generator and an instrument in accordance with embodiments of the invention.

Referring now to FIG. 45, the instrument 1 in use is intended for connection to an electrosurgical generator 4500 having a controllable radiofrequency (RF) source therein (not shown) that in use produces an RF coagulation signal that coagulates or seals tissue when applied thereto via the electrodes of the end-effector of the instrument 1. Electrosurgical generator 4500 includes control input switches 4504 and 4502, to respectively allow the generator to be turned on and off, and to allow the power of the RF coagulation signal fed to the instrument 1 to be controlled. In these respects, the electrosurgical generator 4500 is conventional.

The instrument 1 is connected in use to generator 4500 by control and power line 4506, which contains separate electrical lines to allow an RF signal to be fed to the end-effector of the instrument 1 via the internal wiring described previously, and also to allow a control signal to be received from the switch 26 of the instrument 1, to command the electrosurgical generator to output an RF coagulation signal to the instrument 1. In use the surgeon activates the generator via on-off switch 4504, and selects the coagulation or sealing signal strength to be generated by the internal RF source using buttons 4502. During a surgical procedure with the instrument when a sealing or coagulation RF signal is required at the end-effector, the surgeon controls the generator to produce such a signal by pressing the switch 26 on the instrument, the generated RF signal then being passed via the electrical lines 4506 to the end-effector. That is, pressing of the switch 26 in use causes an RF coagulation or sealing signal to be supplied to the appropriate electrodes contained within the end-effector.

11. SUMMARY

In view of all of the above, therefore, embodiments of the invention provide an advanced electrosurgical forceps instrument which allows for easy and ergonomic one-handed operation by the user, provides rotational flexibility of the end-effector, controls the three that is applied by the end-effector to the tissue being grasped so as to prevent excessive force being applied, and allows for a convenient mechanical cut of the grasped tissue whilst at the same time providing for electrosurgical coagulation or sealing of the tissue. Moreover, the instrument has been further designed so as to be simple and low-cost to construct, whilst providing a compact instrument through efficient use of the space available within the respective internal activation mechanisms.

Various further modifications to the above described embodiments, whether by way of addition, deletion or substitution, will be apparent to the skilled person to provide additional embodiments, any and all of which are intended to be encompassed by the appended claims.

The invention claimed is:

1. A surgical instrument comprising:
   a handle, having a longitudinal axis defining a generally forward and a rearward direction, the handle including:
      a forward section extending generally along the longitudinal axis, and a rearward section extending at an angle to the longitudinal axis, and
      an external casing having one or more apertures,
   an elongate shaft extending from the forward section of the handle,
   an end effector positioned at a distal end of the elongate shaft,
   a rotatable thumb-wheel positioned at a rearward end of the forward section of the handle with no external actuator disposed between the thumb-wheel and a rearward-most end of the forward section, the thumb-wheel protruding through the one or more apertures in the external casing, rotation of the thumb-wheel being configured to cause a corresponding rotation of the elongate shaft, and a switch for electrosurgical energy supply positioned on the forward section of the handle, wherein:
   the thumb-wheel has a rearward end and a forward end, and a generally tapered external surface such that at least part of the external surface of the thumb-wheel slopes from a relatively narrow diameter at the rearward end of the thumb-wheel, to a relatively broader diameter towards the forward end of the thumb-wheel so as to extend in the forward direction at a first angle to the longitudinal axis,
   a lateral wall of the external casing in a region of the thumb-wheel extends in the forward direction from the rearward end of the thumb-wheel to a position forward of the forward end of the thumb-wheel so as to slope away from the longitudinal axis at a second angle to the longitudinal axis,
   the first angle and the second angle are substantially equal, and
   a dimension of the external casing extending in a protruding direction of the thumb-wheel through at least one of the one or more apertures decreases in the rearward direction from the position forward of the forward end of the thumb-wheel to the rearward end of the thumb-wheel.

2. A surgical instrument according to claim 1, wherein the external surface of the thumb-wheel is provided with a scalloped surface including a plurality of indents adapted to receive the fingers and thumb of a user operating the thumb-wheel.

3. A surgical instrument according to claim 2, wherein the plurality of indents are tapered such that they form a relatively narrow diameter at the rearward end of the thumb-wheel, and a relatively broader diameter towards the forward end of the thumb-wheel.

4. A surgical instrument according to claim 3, wherein the plurality of indents taper at an angle of between 5 and 35 degrees.

5. A surgical instrument according to claim 4, wherein the plurality of indents taper at an angle of between 10 and 25 degrees.

6. A surgical instrument according to claim 2, wherein the thumb-wheel includes between 6 and 10 indents.

7. A surgical instrument according to claim 6, wherein the thumb-wheel includes 8 indents.

8. A surgical instrument according to claim 2, wherein the indents are narrower at the rearward end of the thumb-wheel and wider at the forward end of the thumb-wheel.

9. A surgical instrument according to claim 2, wherein the sloping part of the external surface of the thumb-wheel is constituted by a centre line of each of the indents.

10. A surgical instrument according to claim 1, wherein the one or more apertures in the external casing include two apertures, opposite one another on each side of the handle.

11. A surgical instrument according to claim 1, wherein the one or more apertures are trapezoidal in shape.

12. A surgical instrument according to claim 11, wherein the one or more trapezoidal apertures have parallel sides orthogonal to the longitudinal axis of the handle.

13. A surgical instrument according to claim 12, wherein one of the parallel sides is longer than the other, the longer side being at a forward end of the aperture and the shorter side being at a rearward end of the aperture.

14. A surgical instrument according to claim 1, further comprising an actuating mechanism movable between a first position and a second position, movement of the actuating mechanism from its first position to its second position being configured to cause the end effector to move from a first condition to a second condition.

15. A surgical instrument according to claim 1, further comprising an actuating mechanism movable between a first position and a second position, wherein:
   the end effector comprises a pair of opposing first and second jaw members, and movement of the actuating mechanism from its first position to its second position is configured to cause at least one of the jaw members to move relative to the other from a first open position in which the jaw members are disposed in a spaced relation relative to one another, to a second closed position in which the jaw members cooperate to grasp tissue therebetween.

16. A surgical instrument according to claim 1, wherein the end effector includes one or more electrodes, and the instrument includes electrical connections capable of connecting the instrument to an electrosurgical generator.

17. A surgical instrument according to claim 1, further comprising: an actuating mechanism movable between a first position and a second position, wherein: the switch is for activating or deactivating a radio frequency supply to the end effector and is disposed on the forward section of the handle at a position at least partially overlapping the thumb-wheel in a direction orthogonal to the longitudinal axis of the handle, and the actuating mechanism protrudes from the external casing of the handle on an opposite side of the thumb-wheel than the switch.

18. A surgical instrument comprising:
a handle, having a longitudinal axis defining a generally forward and a rearward direction, the handle including:
  a forward section extending generally along the longitudinal axis, and a rearward section extending at an angle to the longitudinal axis, and
  an external casing having one or more apertures,
an elongate shaft extending from the forward section of the handle,
an end effector positioned at a distal end of the elongate shaft,
a rotatable thumb-wheel positioned in an immediate vicinity of a rearward end of the forward section of the handle with no external actuator disposed between the thumb-wheel and a rearward-most end of the forward section, the thumb-wheel protruding through the one or more apertures in the external casing, rotation of the thumb-wheel being configured to cause a corresponding rotation of the elongate shaft, and a switch for electrosurgical energy supply positioned on the forward section of the handle,
wherein:
the thumb-wheel has a rearward end and a forward end, and a generally tapered external surface such that at least part of the external surface of the thumb-wheel slopes from a relatively narrow diameter at the rearward end of the thumb-wheel, to a relatively broader diameter towards the forward end of the thumb-wheel so as to extend in the forward direction at a first angle to the longitudinal axis,
a lateral wall of the external casing in a region of the thumb-wheel extends in the forward direction so as to slope away from the longitudinal axis at a second angle to the longitudinal axis, and
the first angle and the second angle are substantially equal.

19. A surgical instrument according to claim 18, wherein the thumb-wheel is positioned closer to the rearward end of the forward section of the handle than a forward end of the forward section of the handle.

* * * * *